United States Patent
Charrier et al.

(10) Patent No.: US 8,779,127 B2
(45) Date of Patent: Jul. 15, 2014

(54) PROCESSES FOR PREPARING SUBSTITUTED PYRIMIDINES

(75) Inventors: Jean-Damien Charrier, Grove Wantage (GB); Francesca Mazzei, Benson (GB); David Kay, Purton (GB); Andrew Miller, Upton Didcot (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/585,861

(22) Filed: Aug. 15, 2012

(65) Prior Publication Data

US 2013/0066069 A1 Mar. 14, 2013

Related U.S. Application Data

(63) Continuation of application No. 12/436,407, filed on May 6, 2009, now Pat. No. 8,268,829, which is a continuation of application No. 11/500,981, filed on Aug. 9, 2006, now Pat. No. 7,557,106, which is a continuation of application No. 10/464,430, filed on Jun. 18, 2003, now abandoned.

(60) Provisional application No. 60/411,609, filed on Sep. 18, 2002, provisional application No. 60/390,658, filed on Jun. 20, 2002.

(51) Int. Cl.
*C07D 403/14* (2006.01)
*C07D 403/12* (2006.01)
*C07D 417/14* (2006.01)

(52) U.S. Cl.
USPC ........... 540/575; 544/122; 544/295; 544/317; 544/318

(58) Field of Classification Search
USPC .................. 540/575; 544/122, 295, 317, 318
See application file for complete search history.

(56) References Cited

U.S. PATENT DOCUMENTS

| | | | |
|---|---|---|---|
| 3,133,081 A | 5/1964 | Lafferty et al. | |
| 3,755,322 A | 8/1973 | Winter et al. | |
| 3,930,970 A | 1/1976 | Barton et al. | |
| 3,998,951 A | 12/1976 | Harnish et al. | |
| 4,051,252 A | 9/1977 | Mayer et al. | |
| 4,493,726 A | 1/1985 | Burdeska et al. | |
| 4,540,698 A | 9/1985 | Ishikawa et al. | |
| 4,711,951 A | 12/1987 | Axen et al. | |
| 5,124,441 A | 6/1992 | Carlsson et al. | |
| 5,710,158 A | 1/1998 | Myers et al. | |
| 5,916,908 A | 6/1999 | Giese et al. | |
| 5,972,946 A | 10/1999 | Murata et al. | |
| 6,093,716 A | 7/2000 | Davis et al. | |
| 6,184,226 B1 | 2/2001 | Chakravarty et al. | |
| 6,200,977 B1 | 3/2001 | Cushing et al. | |
| 6,277,989 B1 | 8/2001 | Chakravarty et al. | |
| 6,495,582 B1 | 12/2002 | Hale et al. | |
| 6,528,509 B1 | 3/2003 | Hale et al. | |
| 6,528,513 B2 | 3/2003 | Cushing et al. | |
| 6,558,657 B1 | 5/2003 | Mandeville, III et al. | |
| 6,562,971 B2 | 5/2003 | Frauenkron et al. | |
| 6,569,499 B2 | 5/2003 | Grammatica et al. | |
| 6,579,983 B1 | 6/2003 | Batchelor et al. | |
| 6,589,958 B1 | 7/2003 | Frietz | |
| 6,593,326 B1 | 7/2003 | Bradbury et al. | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,641,579 B1 | 11/2003 | Bernardi et al. | |
| 6,642,227 B2 | 11/2003 | Cao et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,689,778 B2 | 2/2004 | Bemis et al. | |
| 6,696,452 B2 | 2/2004 | Davies et al. | |
| 6,716,851 B2 | 4/2004 | Cai et al. | |
| 6,727,251 B2 | 4/2004 | Bebbington et al. | |
| 6,743,791 B2 | 6/2004 | Cao et al. | |
| 6,825,190 B2 | 11/2004 | Moon et al. | |
| 6,838,464 B2 | 1/2005 | Pease et al. | |
| 6,841,579 B1 | 1/2005 | Plowman et al. | |
| 6,846,928 B2 | 1/2005 | Bebbington et al. | |
| 6,884,804 B2 | 4/2005 | Choon-Moon | |
| 6,919,338 B2 | 7/2005 | Mortlock et al. | |
| 6,949,544 B2 | 9/2005 | Bethiel et al. | |
| 6,989,385 B2 | 1/2006 | Bebbington et al. | |
| 7,008,948 B2 | 3/2006 | Bebbington et al. | |

(Continued)

FOREIGN PATENT DOCUMENTS

| EP | 00198811 | 12/1980 |
|---|---|---|
| EP | 0136976 | 4/1985 |

(Continued)

OTHER PUBLICATIONS

Rouse, J. et al., "A Novel Kinase Cascade Triggered by Stress and Heat Shock That Stimulates MAPKAP Kinase-2 and Phosphorylation of the Small Heat Shock Proteins," Cell, 78, 1027-1037 (1994).
Rueeger, H. et al, "Design, synthesis and SAR of a series of 2-substituted 4-amino-quinazolineneuropeptide Y Y5 receptor antagonists," Bioor. Med. Chem. lett., 10(11), 1175-1180 (2000).
Shikhaliev, K.S. et al., "Heterocyclization of quinazol-2-ylguanidines. 1. Reaction with amino acids", Chem. Heterocycl. Compd. 35 (7), 818-820 (1999).
Simone, J.V., "Oncology Introduction" in Cecil Textbook in Medicine, 20th ed. vol. 1, 1004-1010 (1996).
Singh, S.P. et al., "Synthesis & Mass Spectra of Some Substituted 2-(2'-Benzazolylamino)pyrimidines", Indian J. Chem. Sect. B, 22(1): 37-42 (1983).

(Continued)

*Primary Examiner* — Deepak Rao
(74) *Attorney, Agent, or Firm* — Rory C. Stewart

(57) ABSTRACT

The present invention provides a facile process for the preparation of tri- and tetra—substituted pyrimidines. The process is useful for preparing inhibitors of protein kinases, especially Aurora kinase. These inhibitors are useful for treating or lessening the severity of Aurora—mediated diseases or conditions.

28 Claims, No Drawings

(56) References Cited

U.S. PATENT DOCUMENTS

| | | |
|---|---|---|
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington et al. |
| 7,115,739 B2 | 10/2006 | Bebbington et al. |
| 7,179,826 B2 | 2/2007 | Bebbington et al. |
| 7,253,187 B2 | 8/2007 | Cao et al. |
| 7,304,061 B2 | 12/2007 | Hale et al. |
| 7,557,106 B2 | 7/2009 | Charrier |
| 2002/0052386 A1 | 5/2002 | Armistead et al. |
| 2002/0065270 A1 | 5/2002 | Moriarty et al. |
| 2003/0064982 A1 | 4/2003 | Davies et al. |
| 2003/0069248 A1 | 4/2003 | Chakravarty et al. |
| 2003/0096813 A1 | 5/2003 | Cao et al. |
| 2003/0105090 A1 | 6/2003 | Bebbington et al. |
| 2003/0199526 A1 | 10/2003 | Choquette et al. |
| 2003/0207873 A1 | 11/2003 | Harrington |
| 2004/0009981 A1 | 1/2004 | Bebbington et al. |
| 2004/0097531 A1 | 5/2004 | Ledeboer et al. |
| 2004/0157893 A1 | 8/2004 | Bebbington et al. |
| 2004/0167141 A1 | 8/2004 | Bebbington et al. |
| 2004/0214814 A1 | 10/2004 | Bebbington et al. |
| 2005/0038023 A1 | 2/2005 | Bebbington et al. |
| 2005/0234059 A1 | 10/2005 | Hale et al. |
| 2006/0270660 A1 | 11/2006 | Charrier et al. |

FOREIGN PATENT DOCUMENTS

| | | |
|---|---|---|
| EP | 0302312 | 2/1989 |
| GB | 2052487 | 1/1981 |
| JP | 06065237 | 3/1994 |
| JP | 10130150 | 5/1998 |
| JP | 2000026421 | 1/2000 |
| WO | 9322681 | 11/1993 |
| WO | 9509851 | 4/1995 |
| WO | 9515758 | 6/1995 |
| WO | 9614843 | 5/1996 |
| WO | 9709325 | 3/1997 |
| WO | 9719065 | 5/1997 |
| WO | 9802434 | 1/1998 |
| WO | 9811095 | 3/1998 |
| WO | 9814450 | 4/1998 |
| WO | 9816502 | 4/1998 |
| WO | 9838171 | 9/1998 |
| WO | 9918781 | 4/1999 |
| WO | 9941253 | 8/1999 |
| WO | 9947154 | 9/1999 |
| WO | 9962518 | 12/1999 |
| WO | 9965897 | 12/1999 |
| WO | 0012497 | 3/2000 |
| WO | 0021955 | 4/2000 |
| WO | 0038675 | 7/2000 |
| WO | 0039101 | 7/2000 |
| WO | 0042029 | 7/2000 |
| WO | 0059509 | 10/2000 |
| WO | 0078757 | 12/2000 |
| WO | 0112621 | 2/2001 |
| WO | 0125220 | 4/2001 |
| WO | 0144242 | 5/2001 |
| WO | 0139777 | 6/2001 |
| WO | 0140215 | 6/2001 |
| WO | 0147879 | 7/2001 |
| WO | 0147897 | 7/2001 |
| WO | 0160816 | 8/2001 |
| WO | 0164655 | 9/2001 |
| WO | 0174768 | 10/2001 |
| WO | 0179198 | 10/2001 |
| WO | 0208244 | 1/2002 |
| WO | 0218346 | 3/2002 |
| WO | 0222601 | 3/2002 |
| WO | 0222602 | 3/2002 |
| WO | 0222603 | 3/2002 |
| WO | 0222604 | 3/2002 |
| WO | 0222605 | 3/2002 |
| WO | 0222606 | 3/2002 |
| WO | 0222607 | 3/2002 |
| WO | 0222608 | 3/2002 |
| WO | 0224667 | 3/2002 |
| WO | 0247690 | 6/2002 |
| WO | 0250065 | 6/2002 |
| WO | 0250066 | 6/2002 |
| WO | 02057259 | 7/2002 |
| WO | 02059111 | 8/2002 |
| WO | 02059112 | 8/2002 |
| WO | 02062789 | 8/2002 |
| WO | 02066461 | 8/2002 |
| WO | 02068415 | 9/2002 |
| WO | 02079197 | 10/2002 |
| WO | 03026664 | 4/2003 |
| WO | 04000833 | 12/2003 |
| WO | 2004013140 | 2/2004 |
| WO | 2007041358 | 4/2007 |
| WO | WO2008077086 | 6/2008 |

OTHER PUBLICATIONS

Singhal, N. et al., "Synthesis and Antimalarial Activity of Some New Quinazoline Derivatives", Indian Chem. Soc. 61, 690-693 (1984).

Sivaraman, V.S. et al., "Hyperexpression of Mitogen-activated Protein Kinase in Human Breast Cancer", J. Clin. Invest., 99(7), 1478-1483 (1997).

Soriano, P. et al., ed Disruption of the C-SRC Proto-Ocogene Leads to Osteopetrosis in Mice, Cell, 64: 693-702 (1991).

Staley, C.A. et al., "Decreased Tumorigenicity of a Human Colon Adenocarcinoma Cell Line by an Antisense Expression Vector Specific for c-Src," Cell Growth Diff., 8 269-274 (1997).

Suzuki, S. et al., "Application of electrogenerated triphenylmethyl anion as a base for alkylation of arylacetic esters and arylacetonitrites and isomerization of allylbenzenes," Can. J. Chem., 72(2): 357-361 (1994).

Takashima, K. et al., "Tau Protein Kinase I is Essential for Amyloid β-Protein-Induced Neurotoxicity," PNAS 90, 7789-7793 (1993).

Takayanagi, H. et al., "Suppression of arthritic bone destruction by adenovirus-mediated csk gene transfer to synoviocytes and osteoclasts," J. Clin. Invest., 104, 137-146(1999).

Talamonti, M.S. et al., "Increase in activity and level of pp60c-src in progressive stages of human colorectal cancer," J. Clin Invest., 91(1): 53-60 (1993).

Tanaka, T.U. et al., PubMed Abstract, "Evidence that the Ipl1-Sli15 (Aurora Kinase-INCENP) Complex Promotes Chromosome Bi-orientation by Altering Kinetochore-Spindle Pole Connections," Cell. Feb. 8, 2002, 108 (3), 317-329 (2002).

Tanji, K. et al., "Purines. X. Reactivities of Methyl Groups on 9-Phenylpurines: Condensation with an Aldehyde or an Ester, and Oxidation with Selenium Dioxide," Chem. Phar. Bull., 40 (1), 227-229 (1992).

The Condensed Chemical Dictionary, Sixth Edition h Rose, 38 by Arthur and Elizabeth Rose, 38 (1961).

Ti, J. et al., "Anticandidal activity of pyrimidine-peptide conjugates," J. Med. Chem., 23(8), 913-918 (1980).

Toriyabe, Keiji et al., "Preparation of sulfur-containing arylthiazoles and insecticides," Chemica Abstracts, 132(8): 93314 (2000).

Traxier P. et al., "Use of a pharmacophonre model for the design of EGF-R Tyrosine Kinase Inhibitors: 4-(Phenylamino)Pyrazolo[3,4-d]pyrimidines," Journal of Medicinal Chemistry, 40(22): 3601-3616 (1997).

Venugopalan, B. et al., "Synthesis and antimalarial activity of pyrido 3,2-f)quinozalines and their N-oxides," Indian J. Chem. Sect. B, 34, 9, 779-790 (1995).

Wagman, A.S. et al., "Discovery and Development of GSK3 Inhibitors for the Treatment of Type 2 Diabetes," Current Pharmaceutical Design, 10, 1105-1137 (2004).

Warner, S.L. et al., "Targeting Aurora-2 Kinase in Cancer," Mol. Cancer Thera., 2, 589-585, 2003.

Whelchel, A. et al., "Inhibition of ERK Activation Attenuates Endothelin-stimulated Airway Smooth Muscle Cell Proliferation," Am. J. Respir. Cell Mol. Biol., 16, 589-596 (1997).

(56) References Cited

OTHER PUBLICATIONS

Wiener, J.R., "Decreased Src Tyrosine Kinase Activity Inhibits Malignant Human Ovarian Cancer Tumor Growth in a Nude Mouse Model," Clin. Cancer Res., 5, 2164-2170 (1999).
Wolft, Manfred E., "Burger's Medicinal Chemistry, 1" 5th ed., Part 1" John Wiley & Sons, 1995, pp. 975-977.
Yuan, Z.Q. et al., "Frequent activation of AKT2 and induction of apoptosis by inhibition of phosphoinositide-3-OH kinase/Akt pathway in human ovarian cancer," Oncogene, 19, 2324-2330 (2000).
Zhang, Z. et al., "Destabilization of β-catenin by mutations in presenilin-1 potentiates neuronal apoptosis," Nature, 395, 698-702 (1998).
Office Action from U.S. Appl. No. 10/026,992, mailed May 22, 2008.
Agarwal, N. et al., "Suitably Functionalized Pyrimidines as Potential Antimycotic Agents", Bioorg. Med. Chem. Ltt., 10, 8, 703-706 (2000).
Ali, N.m. et al., "Palladium-Catalyzed Cross Coupling Reactions of Arylboronic Acids with Pi-Deficient Heteroaryl Chlorides" Tetrahedron, 48 (37), 8117-8126 (1992).
Alonso, M. et al., "GSK-3 Inhibitors: Discoveries and Developments", Current Medicinal Chemistry, 11, 755-763 (2004).
Anderson, Neil G. "Requirement for integration of signals from two distinct phosphorylation pathways for activation of MAP kinase." Nature, 343, 651-653 (1990).
Anonymous, "Vertex Inhibitors of Aurora-2, glycogen synthase kinase-3 and Src Kinase", Expert Opin. Ther. Patents 14(3): 439-443 (2004).
Bai, G.U. et al., "Triazines and Related Products. Part 28' Conversion of 3-Aryl-I-(2-cyanophenyl) triazenes into 3-Arlquinazolin-4(3H)-ones with Formamide" J. Chem. Soc. Perkin Trans. I, 2765-2766 (1984).
Baig, Ghouse Unissa et al. "Triazines and related products. Part 27. Thermolysis of 4-anilino-1,2,3-benzotriazines," J. Chem., Soc., Perkin Trans. 1(5): 999-1003 (1984).
Banker, G.S. et al., "Modern Pharmaceutics", 34d ed., Marcel Dekker, New York 1996, pp. 451& 596.
Biagi, G. et al., Synthesis of 4,6-Distributed and 4,5,6-Trisubstituted-2-Phyl-pyrimidines and their Affinity Towards A1 Adenosine Receptors, IL Farmaco., 52(1), 61-65 (1997).
Biscardi, J.S. et al., "c-Src, Receptor Tyrosine Kinases, and Human Cancer", Adv. Cancer Res., 76, 61 (1999).
Bischoff, J.R. et al., "A homologue of *Drosophila* aurora kinase is oncogenic and amplified in human colorectal cancers", The EMBO Journal, 17(11): 3052-3065 (1998).
Bischoff, J.R., et al., "The Aurora/IpI1p kinase family: regulators of chromosome segregation and cytokinesis", Cell Biology, 9, 454-459 (1999).
Bjorbaek, c. et al., "Divergent Functional Roles for p90rsk Kinase Domains", J. Biol. Chem., 270(32, 19948-19552 (1995).
Bokemeyer, D. et al., "Multiple intracellular MAP kinase signaling cascades", Kidney Int., 49, 1187-1198 (1996).
Bolen, J.B. et al., "Activation of pp60c-src protein kinase activity in human colon carcinoma", PNAS, 84, 2251-2255 (1987).
Boschelli et al., "Small molecule inhibitors of Src family kinases", Drugs of the Future, 25(7):717-736 (2000).
Brownlees J. et al., "Tau phosphorylation in transgenic mice expressing glycogen synthase kinase-3beta transgenes", Neuroreport., 8(15), 3251-5 (1997).
Brunswick, D.J. et al., "Cyclic Amidines. Part XXII. Novel Isomerism of Disubstituted Tricycioquinazolines and Molecular Orientations in Carcinogenesis", J. Chem. SOC. (3), 2641-2647 (1970).
Campbell, S.F. et al., "2,4-Diamino-6,7-dimethoxyquinazolines. 3.2(4-Heterocyclylpiperazin-I-yl) Derivatives as α1-Adrenoceptor Antagonists and Antihypertensive Agents," J. Med Chem., 30, 1794-1798 (1987).
CAPLUS listing Accession No. 1994:292136, Nakajima, Y. et al., "Pyrazoles agricultural and horticultural bactericides," JP 06065237 (1994).

Casanova, B. et al., "revision critica de la patogenia actual de la esclerosis multiple y futuras direcciones posibles," Rev. Neurol., 28 (9): 909-915 (1999).
Chalmers, D.T., et al., "Corticotrophin-releasing factor receptors: from molecular biology to drug design," TiPS, 17, 769-776 (2001).
Charpiot, B. et al., "Quinazolines: Combined type 3 and 4 phosphodiesterase inhibitors", Bioorg. Med. Chem. Lett., 8 (20), 2891-2896 (1988).
Chen, R.H. et al., "Phosphorylation of the c-Fos transrepression domain by mitogent-activated protein kinase and 90-kDa ribosomal S6 kinase", Proc. Natl. Acad. Sci. USA, 90, 10952-10956 (1993).
Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).
Coghlan, M.P. et al., "Selective small molecule inhibitors of glycogen synthase kinase-3 modulate glycogen metabolism and gene transcription", Chemistry & Biology, 7, 793-803 (2000).
Cohen, P. et al., "The renaissance of GSK3," Nat. Rev. Mol. Cell Biol., 2, 769-776 (2001).
Cohen, P., "Dissection of the Protein Phosphorylation Cascades Involved in Insulin and Growth Factor Action", Biochem. Soc. Trans., 21-555-567 (1993).
Coleman, R.A., "The Biological Evaluation of New Compounds" in Medicinal Chemistry: Principles and Practice, king, Frank D. ed, Royal Society of Chemistry, 53-66 (1994).
Crespo, M.I., et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).
Crews, C.M. et al., "The Primary Structure of MEK, a Protein Kinase That Phosphorylates the ERK Gene Product", Science, 258, 478-480 (1992).
Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).
Curd, F.H.S. et al., "Synthetic antimalarials. Part XVII. Some aminoalkylaminoquinoline derivatives", J. Chem. Soc. 899-909 (1947).
D'Atri, G. et al., "Novel pyrimidine and 1,3,5-triazine hypolipemic agents", J. Med. Chem. 27(12), 1621-1629 (1984).
Damasio, A.R., "Alzheimer's Disease and Related Dementias," in Cecil Textbook of Medicine, 20th ed., 2:1992-1996 (1996).
Douglas, et al., "Introduction to Viral Disease" in Cecil Textbook of Medicine, 20th Ed., vol. 2, 1739-1749 (1996).
Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).
Fedorynski, M. et al., "Synthesis of 1-Arycyclopropanecarbonitriles under Phase-transfer Cataylist Conditions", Org. Prep. Proced. Int., 27(3), 355-359 (1995).
Fischer, P.M. et al., "inhibitors of Cyclin-Dpendent Kinases as Anti-Cancer Therapeutics", Current Med. Chem., 7, 1213-1245 (2000).
Fischer A., "Therapeutic Strategies in Alzheimer's Disease: M1 Muscarinic Agonists," Jpn. J. Pharmacol., 84(2):101-12 (2000).
Fox T. et al. "A single amino acid substitution makes ERK2 susceptible to pyridinyl imidazole inhibitors of p38 MAP kinase", Protein Sci., 7:2249-2255 (1998).
Frame, M.C., "Src in cancer: deregulation and consequences for cell behaviour," Biochimica et Biophysica Acta, 1602, 114-130 (2002).
Frampton, J.E. et al., "Pentoxifyline (Oxpentifylline)—A Review of its Therapeutic Efficacy in the Management of Peripheral Vascular and Cerebrovascular Disorder," Drugs & Aging, 7(6): 480-503 (1995).
Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).

(56) References Cited

OTHER PUBLICATIONS

Fry, d.W. et al., "Inhibitors of cyclin-dependent kinases as therapeutic agents for the treatment of cancer", Current Opin. Oncol. Endoc. & Metab. Investig., 2-40-59 (2000).
Ganellin, C.R., "Past Approaches to Discovering New Drugs as Medicines" in Medicinal Chemistry, Principles and Practices. King, Frank D. ed, Royal Society of Chemistry, 189-205 (1994).
Garigipati, R.S., "An efficient conversion of nitriles to amidines", Tetrahedron Lett., 31(14)., 1969-1972 (1990).
Gerschon, H. et al., "Pyrimidines 7. A Study of the Chlorination of Pyrimidines with Phosphorous Oxychloride in the Presence of N,N-Dimethylaniline", J. Heterocyclic Chem., 21, 1161-1167 (1984).
Glossary of Class Names of Organic Compounds and Reactive Intermediates Based on Structure found from http://www.chem.qmul.ac.uk/iupac/class/index.html (last visited on Nov. 18, 2007).
Gnecco, D. et al., "An Improved Preparation of 1-Methyl-4-Cyano-4-phenylpiperidine", Org. Prep. Proced. Int., 18 (4), 478-480 (1996).
Hamdane, M. et al., "Pin 1—A Therapeutic Target in Alzheimer Neurodegeneration," J. Mol. Neurosci., 19(3): 275:87 (2002).
Haq. S. et al., "Glycogen Synthase Kinase-3β Is a Negative Regulator of Cardiomyocyte Hypertrophy", J. Cell Biol., 151(1), 177-129 (2000).
Hardt, S.E., et al., "Glycogen Synthase Kinase-3β—A Novel Regulator of Cardiac Hypertrophy and Development," Circulation Research, 90: 1055-1063 (2002).
Harrington, E.A. et al., "VX-680, a potent and selective small-molecule inhibitor of the Aurora kinases, suppresses tumor growth in vivo," Nat. Med., 10(3): 262-267 (2004).
Haworth, R.D. et al., "Synthetic antimalarials. Part XXVII. Some derivatives of phthalazine, quinoxaline, and isoquinoline", J. Chem. Soc., 777-782 (1948).
Heaney, F., et al., "Pyrimidine annelated heterocycles-synthesis and cycoaddition of the first pyrimido[1,4]diazepine N-oxides," J. Chem. Soc., Perkin Trans., 1:622-632 (2001).
Henriksen, E.J. et al., "Modulation of muscle insulin resistance by selective inhibition of GSK-3 in Zucker diabetic fatty rats," Am. J. Physiol. Endocrinol. Metab., 284: E892-E900 (2003).
Heutink, P., "Untangling tau-related dementia", Hum. Mol. Genet., 9(6): 979-986 (2000).
Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).
IUPAC Compendium of Chemical Terminology on a definition of "aliphatic compounds" found from http://www.chemsoc.org/chembytes/goldbook/index.htm (last visited on Nov. 18, 2007).
Ivashchenko A.V. et al., "Synthesis and Study of Heteroaromatic Ligands Containing a Pyrimidine Ring", Khim. Geterotsikl. Soedin., (12), 1673-7, (1980).
Jambhekar, S.S., "Biopharmaceutical Properties of Drug Substances" in Principles of Medicinal Chemistry, 4th ed., 12-24 (1995).
Jeffrey, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).
Katzung, Bertram G., Basic and Clinical Pharmacology, 7th Edition, 1998, pp. 881-884.
Kelarev, V.I. et al., "Synthesis of amino derivatives of 1,3,5-triazine containing 1,3-4-thiadiazole fragments," Izvestiya Vysshikh Uchebnkh Zavedenii, Khimiya I Khimicheskaya Tekhnologiya, 40(5):27-32 (1997).
Kim, L. et al., "GSK3, a master switch regulating cell-fate specification and tumorigenesis" Current Opinion in Genetics & Development, 10:508-514 (2000).
Kim, Y.Z. et al., "Synthesis and Antimicrobial Activity of Novel [)3-Aminopyrimidiniumyl)thio]methyl Cephalosporins", J. Med. Chem., 37(22); 3828-3833 (1994).
Kimura M. et al., "Cell Cycle-dependent Expression and Centrosome Localization of a Third Human Aurora/Ipl1-related Protein Kinase, AIK3", J. Biol. Chem., 274(11); 7334-7340 (1999).

Klein, P.S. et al., "A molecular mechanism for the effect of lithium on development", PNAS, 93:8455-8459 (1996).
Layzer, R.B., "Section Five—Degenerative Diseases of the Nervous System" in Cecil Textbook of Medicine, 20th ed., 2: 2050-2057 (1996).
Lee, S.j. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med. Chem., 38 (18):3547-3557 (1995).
Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).
Lübbers, T. et al., "Design synthesis, and structure-activity relationship studies of ATP analogues as DNA gyrase inhibitors", Bioorg. Med. Chem. Lett., 10, 8, 821-826 (2000).
Lutz, M.L. et al., "Overexpression and Activation of the Tyrosine Kinase Src in Human Pancreatic Carcimona", Biochem. Biophys. Res. 243, 503-508 (1998).
Lynch, S.A. et al., "Increased Expression of the src Proto-Oncogene in Hairy Cell Leukemia and a Subgroup of B-Cell Lymphomas", Leukemia, 7(9), 1416-1422 (1993).
Lyrer, P., Schweiz. "Neue Ansätze in der Akutbehandlung des zerebrovaskulären Insultes." Med. Woohen Schr., 124 (45); 2005-2012 (1994).
Mani, S. et al., "Cyclin-dependent kinase: novel anticancer agents", Exp. Opin. Invest. Drugs, 8, 1849-1870 (2000).
Masaki, T. et al., "pp60c-src Activation in Hepatocellular Carcinoma of Humans and LEC Rats", Hapatology, 27, 1257 (1998).
Massillon, D. et al., "Identification of the glycogenic compound 5-iodotubercidin as a general protein kinase inhibitor", Biochem J., 299: 123-128 (1994).
Medwid, Jeffrey B. et al., "Preparation of triazolo'1, 5-cipyrimidines as potential antiasthma agents," J. Med. Chem., 33 (4): 1230-1241 (1990).
Molina, T.J. et al., "Profound block in thymocyte development in mice lacking p56lck", Nature, 357, 161-164 (1992).
Moodie, S.A. et al., "Complexes of Ras-GTP with Raf-1 and Mitogen-Activated Protein Kinase", Science, 260 (5114), 1658-1661 (1993).
Moss, R.A. et al., "Conversion of 'Obstinate' Nitriles to Amidines by Garigipati's Reaction", Tetrahedron Lett., 36(48), 8761-8764 (1995).
Myers, M. R. et al., "The synthesis and SAR of new 4-(N-alkyl-N-phenyl)amino-6,7-dimethoxyquinazolines and 4-(N-alkyl-N-Phenyl)aminopyrazolo[3,4-d]pyrimidines, inhibitors of CSF-1R tyrosine kinase activity", Bioorg. Med. Chem. Lett., 7, 4, 421-424 (1997).
Nair, M.D., et al., "3-Chloroisocarbostyril & Its Chlorination Products", Indian J. Chem., vol. 5, 467-470 (1967).
Namikawa, Kazuhiko et al., "Akt/Protein Kinase B Prevents Injury-Induced Motoneuron Death and Accelerates Axonal Regeneration," The Journal of Neuroscience, 20(8), 2875-2886 (2000).
Nezu, Y. et al., "Dimethoxypyrimidines as Novel Herbicides, part 1. Synthesis and Herbicidal Activity of Dimethoxyphanoxyphenoxypyrimidines and Analogues," Pestic. Sci., 47(2): 103-113 (1996).
Nezu, Y., et al., "Dimethoxypyrimidines as Novel Herbicides, part 2. Synthesis and Herbicidal Activity of O-Pyrimidinylasalicylates and Analogues," Pestic. Sci., 47(2): 115-124 (1996).
Nigg, E.A., "Mitotic Kinases as Regulators of Cell Division and its Checkpoints," Nat. Rev. Mol. Cell Biol., 2: 21-32 (2001).
Noell, C.W. et al., "Potential purine Antagonists. XX. The Preparation and Reactions of Some Methylthiopurines", J. Am. Chem. Soc., 81(22), 5997-6007 (1959).
Nomenclature found from http://www.cem.msu.edu/~reusch/VirtualText/nomen1.htm (last visited on Nov. 18, 2007).
Norman, M.H. et al., "Structure-Activity Relationships of a Series of Pyrrolo[3,2-d]pyrimidine Derivatives and Related Compounds as Neuropeptide Y5 receptor Antagonists," J. Med. Chem., 43(22), 4288-4312 (2000).
Nugent, R.A. et al., "Pyrimidine Thiotheters: A Novel Class of HIV-1 Reverse Transcriptase Inhibitors with Activity Against BHAP-Resistant HIV", J. Med. Chem., 41, 3793-3803 (1998).

(56) References Cited

OTHER PUBLICATIONS

Okafor, Charles O., "Studies in the Heterocyclic Series. 1,3,9-Triazaphenothiazine Ring System, A New Phenothiazine Ring," J. Org. Chem., 40(19):2753-2755 (1975).

Parnell, E.W., "2-Cyano-4-nitrophenylhydrazine and 3-Amino-5-nitroindazole", J. Chem. Soc., 2363-2365 (1959).

Pei, J. et al., "Distribution, Levels and Activity of Glycogen Synthase Kinase-3 in the Alzheimer Disease Brain", J. Neuropathol. Exp. Neurology, 56, 70-78 (1997).

Prasad, G. et al., "18-Crown-6 as a catalyst in the dialkylation of o-nitrophenacyl derivatives," J. Org. Chem., 25, 7188-7190 (1991).

Raingeaud, J. et al., "MMK3- and MMK6-Regulated Gene Expression Is Mediated by p38 Mitogen-Activated Protein Kinase Signal Transduction Pathway," Mol. Cell. Biol. 16, 1247-1255 (1996).

Rogers., et al., PubMed Abstract, "The aurora kinase AIR-2 functions in the release of chromosome cohesion in *Caenorhabditis elegans* meiosis," J. Cell Biol., 157(2): 219-229 (2002).

Rosen, N. et al., "Analysis of pp60src Protein Kinase Activity in Human Tumor Cell Lines and Tissues," J. Biol. Chem., 261, 13754-13759 (1986).

PROCESSES FOR PREPARING SUBSTITUTED PYRIMIDINES

CROSS REFERENCE TO RELATED APPLICATIONS

This application is a continuation application of U.S. application Ser. No. 12/436,407, filed May 6, 2009, which is a continuation application of U.S. application Ser. No. 11/500,981, filed Aug. 9, 2006, which claims priority to U.S. Provisional Patent Application 60/390,658 filed Jun. 20, 2002 and U.S. Provisional Patent Application 60/411,609 filed Sep. 18, 2002, the contents of which are incorporated herein by reference.

FIELD OF THE INVENTION

The present invention provides a facile process for the preparation of substituted pyrimidines. The process is useful for preparing inhibitors of protein kinases, especially of FLT-3 and the Aurora-family kinases, serine/threonine protein kinases. The present invention also relates to inhibitors of FLT-3, Aurora-1, Aurora-2, and Aurora-3 protein kinases, and compositions thereof.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor alpha (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

The Aurora family of serine/threonine kinases is essential for cell proliferation [Bischoff, J. R. & Plowman, G. D. (The Aurora/Ipl1p kinase family: regulators of chromosome segregation and cytokinesis) *Trends in Cell Biology* 9, 454-459 (1999); Giet, R. and Prigent, C. (Aurora/Ipl1p-related kinases, a new oncogenic family of mitotic serine-threonine kinases) *Journal of Cell Science* 112, 3591-3601 (1999); Nigg, E. A. (Mitotic kinases as regulators of cell division and its checkpoints) Nat. Rev. *Mol. Cell. Biol.* 2, 21-32 (2001); Adams, R. R, Carmena, M., and Earnshaw, W. C. (Chromosomal passengers and the (aurora) ABCs of mitosis) *Trends in Cell Biology* 11, 49-54 (2001)]. Inhibitors of the Aurora kinase family therefore have the potential to block growth of all tumour types.

The three known mammalian family members, Aurora-A ("1"), B ("2") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. In mammalian cells proposed substrates for Aurora include histone H3, a protein involved in chromosome condensation, and CENP-A, myosin II regulatory light chain, protein phosphatase 1, TPX2, all of which are required for cell division.

Since its discovery in 1997 the mammalian Aurora kinase family has been closely linked to tumorigenesis. The most compelling evidence for this is that over-expression of Aurora-A transforms rodent fibroblasts (Bischoff, J. R., et al. A homologue of *Drosophila aurora* kinase is oncogenic and amplified in human colorectal cancers. *EMBO J.* 17, 3052-3065 (1998)). Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the aurora-A locus and chromosomal instability in mammary and gastric tumours has been observed. (Miyoshi, Y., Iwao, K., Egawa, C., and Noguchi, S. Association of centrosomal kinase STK15/BTAK mRNA expression with chromosomal instability in human breast cancers. Int. J. Cancer 92, 370-373 (2001). (Sakakura, C. et al. Tumor-amplified kinase BTAK is amplified and overexpressed in gastric cancers with possible involvement in aneuploid formation. *British Journal of Cancer* 84, 824-831 (2001)). The Aurora kinases have been reported to be over-expressed in a wide range of human tumours. Elevated expression of Aurora-A has been detected in over 50% of colorectal (Bischoff, J. R., et al. A homologue of *Drosophila aurora* kinase is oncogenic and amplified in human colorectal cancers. *EMBO J.* 17, 3052-3065 (1998)) (Takahashi, T., et al. Centrosomal kinases, HsAIRk1 and HsAIRK3, are overexpressed in primary colorectal cancers. *Jpn. J. Cancer Res.* 91, 1007-1014 (2000)). ovarian (Gritsko, T. M. et al. Activation and overexpression of centrosome kinase BTAK/Aurora-A in human ovarian cancer. *Clinical Cancer Research* 9, 1420-1426 (2003)), and gastric tumors (Sakakura, C. et al. Tumor-amplified kinase BTAK is amplified and overexpressed in gastric cancers with possible involvement in aneuploid formation. *British Journal of Cancer* 84, 824-831 (2001)), and in 94% of invasive duct adenocarcinomas of the breast (Tanaka, T., et al. Centrosomal kinase AIK1 is overexpressed in invasive ductal carcinoma of the breast. *Cancer Research.* 59, 2041-2044 (1999)). High levels of Aurora-A have also been reported in renal, cervical, neuroblastoma, melanoma, lymphoma, pancreatic and prostate tumour cell lines. (Bischoff, J. R., et al. A homologue of *Drosophila aurora* kinase is oncogenic and amplified in human colorectal cancers. *EMBO J.* 17, 3052-3065 (1998) (Kimura, M., Matsuda, Y., Yoshioka, T., and Okano, Y. Cell cycle-dependent expression and centrosomal localization of a third human Aurora/Ipl1-related protein kinase, AIK3. *Journal of Biological Chemistry* 274, 7334-7340 (1999))(Zhou et al. Tumour amplifiec kinase STK15/BTAK induces centrosome amplification, aneuploidy and transformation *Nature Genetics* 20: 189-193 (1998))(Li et al. Overexpression of oncogenic STK15/BTAK/Aurora-A kinase in human pancreatic cancer *Clin Cancer Res.* 9(3):991-7 (2003)).

Amplification/overexpression of Aurora-A is observed in human bladder cancers and amplification of Aurora-A is associated with aneuploidy and aggressive clinical behaviour (Sen S. et al Amplification/overexpression of a mitotic kinase gene in human bladder cancer *J Natl Cancer Inst.* 94(17): 1320-9 (2002)). Moreover, amplification of the aurora-A locus (20q13) correlates with poor prognosis for patients with node-negative breast cancer (Isola, J. J., et al. Genetic aberrations detected by comparative genomic hybridization predict outcome in node-negative breast cancer. *American Journal of Pathology* 147, 905-911 (1995)). Aurora-B is highly expressed in multiple human tumour cell lines, including leukemic cells (Katayama et al. Human AIM-1: cDNA cloning and reduced expression during endomitosis in megakaryocyte-lineage cells. *Gene* 244:1-7)). Levels of this enzyme increase as a function of Duke's stage in primary colorectal cancers (Katayama, H. et al. Mitotic kinase expression and colorectal cancer progression. *Journal of the National Cancer Institute* 91, 1160-1162 (1999)). Aurora-C, which is normally only found in germ cells, is also overexpressed in a high percentage of primary colorectal cancers and in a variety of tumour cell lines including cervical adenocarinoma and breast carcinoma cells (Kimura, M., Matsuda, Y., Yoshioka, T., and Okano, Y. Cell cycle-dependent expression and centrosomal localization of a third human Aurora/Ipl1-related protein kinase, AIK3. *Journal of Biological Chemistry* 274, 7334-7340 (1999). (Takahashi, T., et al. Centrosomal kinases, HsAIRk1 and HsAIRK3, are overexpressed in primary colorectal cancers. *Jpn. J. Cancer Res.* 91, 1007-1014 (2000)).

Based on the known function of the Aurora kinases, inhibition of their activity should disrupt mitosis leading to cell cycle arrest. In vivo, an Aurora inhibitor therefore slows tumor growth and induces regression.

Elevated levels of all Aurora family members are observed in a wide variety of tumour cell lines. Aurora kinases are over-expressed in many human tumors and this is reported to be associated with chromosomal instability in mammary tumors (Miyoshi et al 2001 92, 370-373).

Aurora-2 is highly expressed in multiple human tumor cell lines and levels increase as a function of Duke's stage in primary colorectal cancers [Katayama, H. et al. (Mitotic kinase expression and colorectal cancer progression) *Journal of the National Cancer Institute* 91, 1160-1162 (1999)]. Aurora-2 plays a role in controlling the accurate segregation of chromosomes during mitosis. Misregulation of the cell cycle can lead to cellular proliferation and other abnormalities. In human colon cancer tissue, the Aurora-2 protein has been found to be overexpressed [Bischoff et al., *EMBO J.*, 17, 3052-3065 (1998); Schumacher et al., *J. Cell Biol.*, 143, 1635-1646 (1998); Kimura et al., *J. Biol. Chem.*, 272, 13766-13771 (1997)]. Aurora-2 is over-expressed in the majority of transformed cells. Bischoff et at found high levels of Aurora-2 in 96% of cell lines derived from lung, colon, renal, melanoma and breast tumors (Bischoff et al EMBO J. 1998 17, 3052-3065). Two extensive studies show elevated Aurora-2 in 54% and 68% (Bishoff et al EMBO J. 1998 17, 3052-3065) (Takahashi et al 2000 Jpn J Cancer Res. 91, 1007-1014) of colorectal tumours and in 94% of invasive duct adenocarcinomas of the breast (Tanaka et al 1999 59, 2041-2044).

Aurora-1 expression is elevated in cell lines derived from tumors of the colon, breast, lung, melanoma, kidney, ovary, pancreas, CNS, gastric tract and leukemias (Tatsuka et al 1998 58, 4811-4816).

High levels of Aurora-3 have been detected in several tumour cell lines, although it is restricted to testis in normal tissues (Kimura et al 1999 274, 7334-7340). Over-expression of Aurora-3 in a high percentage (c. 50%) of colorectal cancers has also been documented (Takahashi et al 2000 Jpn J Cancer Res. 91, 1007-1014). In contrast, the Aurora family is expressed at a low level in the majority of normal tissues, the exceptions being tissues with a high proportion of dividing cells such as the thymus and testis (Bischoff et al EMBO J. 1998 17, 3052-3065).

For further review of the role Aurora kinases play in proliferative disorders, see Bischoff, J. R. & Plowman, G. D. (The Aurora/Ipl1p kinase family: regulators of chromosome segregation and cytokinesis) *Trends in Cell Biology* 9, 454-459 (1999); Giet, R. and Prigent, C. (Aurora/Ipl1p-related kinases, a new oncogenic family of mitotic serine-threonine kinases) *Journal of Cell Science* 112, 3591-3601 (1999); Nigg, E. A. (Mitotic kinases as regulators of cell division and its checkpoints) Nat. Rev. *Mol. Cell. Biol.* 2, 21-32 (2001); Adams, R. R, Carmena, M., and Earnshaw, W. C. (Chromosomal passengers and the (aurora) ABCs of mitosis) *Trends in Cell Biology* 11, 49-54 (2001); and Dutertre, S., Descamps, S., & Prigent, P. (On the role of aurora-A in centrosome function) *Oncogene* 21, 6175-6183 (2002).

The type III receptor tyrosine kinase, Flt3, plays an important role in the maintenance, growth and development of hematopoietic and non-hematopoietic cells. [Scheijen, B, Griffin J D, *Oncogene,* 2002, 21, 3314-3333 and Reilly, J T, *British Journal of Haematology,* 2002, 116, 744-757]. FLT-3 regulates maintenance of stem cell/early progenitor pools as well the development of mature lymphoid and myeloid cells [Lyman, S, Jacobsen, S, *Blood,* 1998, 91, 1101-1134]. FLT-3 contains an intrinsic kinase domain that is activated upon ligand-mediated dimerization of the receptors. Upon activation, the kinase domain induces autophosphorylation of the receptor as well as the phosphorylation of various cytoplasmic proteins that help propagate the activation signal leading to growth, differentiation and survival. Some of the downstream regulators of FLT-3 receptor signaling include, PLCγ, PI3-kinase, Grb-2, SHIP and Src related kinases [Scheijen, B, Griffin J D, *Oncogene,* 2002, 21, 3314-3333]. FLT-3 kinase plays a role in a variety of hematopoietic and non-hematopoietic malignancies. Mutations that induce ligand independent activation of FLT-3 have been implicated in acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 contributes to the malignant phenotype [Scheijen, B, Griffin J D, *Oncogene,* 2002, 21, 3314-3333]. See also Sawyer, C. l. (Finding the next Gleevec: FLT3 targeted kinase inhibitor therapy for acute myeloid leukaemia) *Cancer Cell*. 1, 413-415 (2002).

Tri- or tetra-substituted pyrimidine derivatives useful as kinase inhibitors are known in the art. Typically, these pyrimidine derivatives are 2,4,6- or 2,4,5,6-substituted, as shown below:

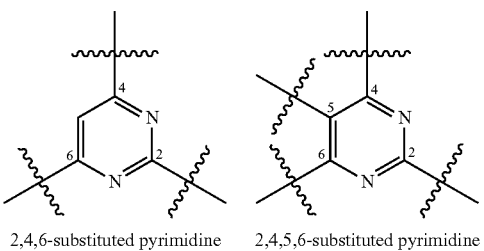 [SMILES: *c1cc(*)nc(*)n1 ; *c1nc(*)c(*)c(*)n1]

2,4,6-substituted pyrimidine      2,4,5,6-substituted pyrimidine

Known methods for preparing such pyrimidine derivatives have many synthetic drawbacks such as lacking the ability to regioselectively introduce substituents at the 2-, 4-, or 6-position in high yields. See M. Botta, Nucleosides Nucleotides, 13, 8, 1994, 1769-78; M. Ban, Bioorg. Med. Chem., 6, 7, 1998, 1057-68; Y. Fellahi, Eur. J. Med. Chem. Chim. Ther., 31, 1, 1996, 77-82; T. J. Delia, J. Het. Chem., 35, 2, 1998, 269-74; H. Uchel, Tetraheron Lett., 36, 52, 1995, 9457-60; and Y. Nezu, Pestic. Sci., 47, 2, 1996, 115-24.

There is a need for a synthetic process that can be readily used to prepare the tri- or tetra-substituted pyrimidine derivatives on a large scale. There is also a need for a process that employs minimal steps and utilizes readily available starting materials and simple reaction media. Ideally, such a process will be easy to scale up, if need be, and will be inexpensive. There is also a need for a process that does not lead to regioisomeric intermediate mixtures that must be separated by, e.g., chromatographic methods. Such separations reduce the overall yields.

It would be desirable to have a synthetic process to produce tri- or tetra-substituted pyrimidine derivatives that possesses the above advantages and thereby improves upon the currently available processes.

SUMMARY OF THE INVENTION

The present invention provides a process for preparing a compound of formula I:

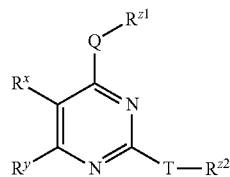

I wherein:
Q and T are each independently selected from oxygen, sulfur or N(R);
each R is independently selected from hydrogen or an optionally substituted $C_{1-6}$ aliphatic group, wherein:
   two R bound to the same nitrogen atom are optionally taken together with the nitrogen to form an optionally substituted 3-7 membered monocyclic or 8-10 membered bicyclic saturated, partially unsaturated, or fully unsaturated ring having 0-3 heteroatoms, in addition to the nitrogen bound thereto, independently selected from nitrogen, oxygen, or sulfur;
$R^x$ is U—$R^5$;
$R^5$ is selected from halogen, $NO_2$, CN, R, or Ar;
each U is independently selected from a valence bond or a $C_{1-4}$ alkylidene chain, wherein:
   up to two methylene units of U are optionally and independently replaced by —O—, —S—, —SO—, —$SO_2$—, —N(R)$SO_2$—, —$SO_2$N(R)—, —N(R)—, —C(O)—, —$CO_2$—, —N(R)C(O)—, —N(R)C(O)O—, —N(R)CON(R)—, —N(R)$SO_2$N(R)—, —N(R)N(R)—, —C(O)N(R)—, —OC(O)N(R)—, —C(R)=NN(R)—, or —C(R)=N—O—;
each Ar is independently selected from an optionally substituted ring selected from a 3-7 membered monocyclic or an 8-10 membered bicyclic saturated, partially unsaturated, or fully unsaturated ring having 0-4 heteroatoms independently selected from nitrogen, oxygen, or sulfur;

$R^y$ is —N($R^1$)$_2$, —OR % or —SR %
each $R^1$ is independently selected from R or a 3-8 membered monocyclic, an 8-10 membered bicyclic, or a 10-12 membered tricyclic saturated, partially unsaturated, or fully unsaturated ring having 0-4 heteroatoms independently selected from nitrogen, oxygen, or sulfur, and wherein:
   each $R^1$ is optionally and independently substituted by up to four substituents independently selected from $R^2$;
each $R^2$ is independently selected from —$R^3$, —$OR^3$, —$SR^3$, —CN, —$NO_2$, oxo, halogen, —N($R^3$)$_2$, —C(O)$R^3$, —OC(O)$R^3$, —$CO_2R^3$, —$SO_2R^3$, —$SO_2$N($R^3$)$_2$, —N($R^3$)$SO_2R^3$, —C(O)NR($R^3$), —C(O)N($R^3$)$_2$, —OC(O)NR ($R^3$), —OC(O)N($R^3$)$_2$, —$NR^3$C(O)$R^3$, —$NR^3$C(O)N($R^3$)$_2$, or —$NR^3CO_2(R^3)$;
each $R^3$ is independently selected from R or Ar;
$R^{z1}$ is selected from a $C_{1-6}$ aliphatic group or a 3-8 membered monocyclic, an 8-10 membered bicyclic, or a 10-12 membered tricyclic saturated, partially unsaturated, or fully unsaturated ring having 0-4 heteroatoms independently selected from oxygen, nitrogen or sulfur, wherein:
   $R^{z1}$ is substituted with 0-4 independently selected $R^2$ groups;
$R^{z2}$ is $C_{1-6}$ aliphatic group or a 3-8 membered monocyclic or an 8-10 membered bicyclic saturated, partially unsaturated, or fully unsaturated ring having 0-4 heteroatoms independently selected from nitrogen, oxygen or sulfur, wherein:
   $R^{z2}$ is substituted by 0-4 substituents independently selected from oxo or U—$R^5$;
said process comprising the step of combining a compound of formula II and a compound of formula $R^y$—H in a suitable medium:

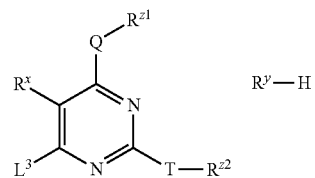

II wherein:
said suitable medium comprises:
   i) a suitable solvent; and
   ii) optionally, a suitable base; and
$L^3$ is a suitable leaving group.

DESCRIPTION OF THE INVENTION

The present invention provides a process for preparing a compound of formula I:

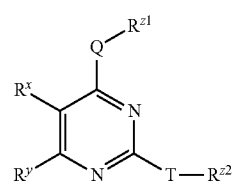

II wherein:

Q and T are each independently selected from oxygen, sulfur or N(R);

each R is independently selected from hydrogen or an optionally substituted $C_{1-6}$ aliphatic group, wherein:

two R bound to the same nitrogen atom are optionally taken together with the nitrogen to form an optionally substituted 3-7 membered monocyclic or 8-10 membered bicyclic saturated, partially unsaturated, or fully unsaturated ring having 0-3 heteroatoms, in addition to the nitrogen bound thereto, independently selected from nitrogen, oxygen, or sulfur;

$R^x$ is U—$R^5$;

$R^5$ is selected from halogen, $NO_2$, CN, R, or Ar;

each U is independently selected from a valence bond or a $C_{1-4}$ alkylidene chain, wherein:

up to two methylene units of U are optionally and independently replaced by —O—, —S—, —SO—, —$SO_2$—, —N(R)$SO_2$—, —$SO_2$N(R)—, —N(R)—, —C(O)—, —$CO_2$—, —N(R)C(O)—, —N(R)C(O)O—, —N(R)CON(R)—, —N(R)$SO_2$N(R)—, —N(R)N(R)—, —C(O)N(R)—, —OC(O)N(R)—, —C(R)=NN(R)—, or —C(R)=N—O—;

each Ar is independently selected from an optionally substituted ring selected from a 3-7 membered monocyclic or an 8-10 membered bicyclic saturated, partially unsaturated, or fully unsaturated ring having 0-4 heteroatoms independently selected from nitrogen, oxygen, or sulfur;

$R^y$ is —N($R^1$)$_2$, —$OR^1$, or —$SR^1$;

each $R^1$ is independently selected from R or a 3-8 membered monocyclic, an 8-10 membered bicyclic, or a 10-12 membered tricyclic saturated, partially unsaturated, or fully unsaturated ring having 0-4 heteroatoms independently selected from nitrogen, oxygen, or sulfur, and wherein:

each $R^1$ is optionally and independently substituted by up to four substituents independently selected from $R^2$;

each $R^2$ is independently selected from —$R^3$, —$OR^3$, —$SR^3$, —CN, —$NO_2$, oxo, halogen, —N($R^3$)$_2$, —C(O)$R^3$, —OC(O)$R^3$, —$CO_2R^3$, —$SO_2R^3$, —$SO_2$N($R^3$)$_2$, —N($R^3$)$SO_2R^3$, —C(O)NR($R^3$), —C(O)N($R^3$)$_2$, —OC(O)NR($R^3$), —OC(O)N($R^3$)$_2$, —$NR^3$C(O)$R^3$, —$NR^3$C(O)N($R^3$)$_2$, or —$NR^3$CO$_2$($R^3$);

each $R^3$ is independently selected from R or Ar;

$R^{z1}$ is selected from a $C_{1-6}$ aliphatic group or a 3-8 membered monocyclic, an 8-10 membered bicyclic, or a 10-12 membered tricyclic saturated, partially unsaturated, or fully unsaturated ring having 0-4 heteroatoms independently selected from oxygen, nitrogen or sulfur, wherein:

$R^{z1}$ is substituted with 0-4 independently selected $R^2$ groups;

$R^{z2}$ is $C_{1-6}$ aliphatic group or a 3-8 membered monocyclic or an 8-10 membered bicyclic saturated, partially unsaturated, or fully unsaturated ring having 0-4 heteroatoms independently selected from nitrogen, oxygen or sulfur, wherein:

$R^{z2}$ is substituted by 0-4 substituents independently selected from oxo or U—$R^5$;

said process comprising the step of combining a compound of formula II and a compound of formula $R^y$—H in a suitable medium:

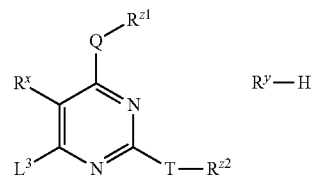

wherein:
said suitable medium comprises:
  i) a suitable solvent; and
  ii) optionally, a suitable base; and
$L^3$ is a suitable leaving group.

According to another embodiment, a compound of formula II is prepared by combining a compound of formula III with a compound of formula $R^{z1}$-Q-H in a suitable medium:

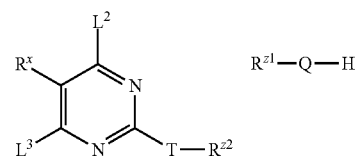

wherein:
said suitable medium comprises:
  i) a suitable solvent; and
  ii) optionally, a suitable base; and
$L^2$ is a suitable leaving group.

According to yet another embodiment, a compound of formula III is prepared by combining a compound of formula IV with a compound of formula $R^{z2}$-T-H in a suitable medium:

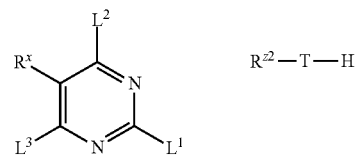

wherein:
said suitable medium comprises:
  i) a suitable solvent; and
  ii) optionally, a suitable base; and
$L^1$ is a suitable leaving group.

A suitable solvent is a solvent or a solvent mixture that, in combination with the combined compounds, may facilitate the progress of the reaction therebetween. The suitable solvent may solubilize one or more of the reaction components, or, alternatively, the suitable solvent may facilitate the agitation of a suspension of one or more of the reaction components. Examples of suitable solvents useful in the present invention are a protic solvent, a halogenated hydrocarbon, an ether, an aromatic hydrocarbon, a polar or a non-polar aprotic solvent, or any mixtures thereof. These and other such suitable solvents are well known in the art, e.g., see, "Advanced Organic Chemistry", Jerry March, 4$^{th}$ edition, John Wiley and Sons, N.Y. (1992).

Preferably the suitable solvent is a $C_{1-7}$ straight or branched alkyl alcohol, ether, or a polar or non-polar aprotic solvent.

For the reaction between a compound of formula II and a compound $R^y$—H, a more preferred suitable solvent is selected from ethanol, isopropanol, t-butanol, n-butanol or tetrahydrofuran.

For the reaction between a compound of formula III and a compound $R^{z1}$-Q-H, a more preferred suitable solvent is selected from ethanol, isopropanol, t-butanol, n-butanol, N,N-dimethylformamide, dimethylsulfoxide, or tetrahydrofuran.

For the reaction between a compound of formula IV and a compound $R^{z2}$-T-H, a more preferred suitable solvent is selected from N,N-dimethylformamide, dimethylsulfoxide, or tetrahydrofuran.

According to an alternate embodiment, the suitable solvent is $R^y$—H. Thus, in such an embodiment, the reagent $R^y$—H acts, in part, as a suitable solvent in combination with a compound of formula II, and also acts, in part, as a reagent and reacts with the compound of formula II to produce compound of formula I.

According to another alternative embodiment, the suitable solvent is $R^{z1}$-Q-H. Thus, in such an embodiment, the reagent $R^{z1}$-Q-H acts, in part, as a suitable solvent in combination with a compound of formula III, and also acts, in part, as a reagent and reacts with the compound of formula III to produce compound of formula II.

According to another alternative embodiment, the suitable solvent is $R^{z2}$-T-H. Thus, in such an embodiment, the reagent $R^{z2}$-T-H acts, in part, as a suitable solvent in combination with a compound of formula IV, and also acts, in part, as a reagent and reacts with the compound of formula IV to produce compound of formula III.

A suitable base is a chemical entity that has the ability to be a proton acceptor. Examples include organic amines, alkaline earth metal carbonates, alkaline earth metal hydrides, and alkaline earth metal hydroxides. These and other such suitable bases are well known in the art, e.g., see, "Advanced Organic Chemistry," Jerry March, $4^{th}$ Ed., pp. 248-253, John Wiley and Sons, N.Y. (1992). Preferred suitable bases include trialkyl amines, sodium carbonate, potassium carbonate, sodium hydride, potassium hydride, sodium hydroxide, or potassium hydroxide. More preferably, the suitable base is diisopropylethylamine or triethylamine.

A suitable leaving group is a chemical group that is readily displaced by a desired incoming chemical moiety. Thus, the choice of the specific suitable leaving group is predicated upon its ability to be readily displaced by the incoming chemical moiety $R^y$ in $R^y$—H, $R^{z1}$-Q in $R^{z1}$-Q-H, or $R^{z2}$-T in $R^{z2}$-T-H. Suitable leaving groups are well known in the art, e.g., see, "Advanced Organic Chemistry," Jerry March, $4^{th}$ Ed., pp. 351-357, John Wiley and Sons, N.Y. (1992). Such leaving groups include, but are not limited to, halogen, alkoxy, sulphonyloxy, optionally substituted alkylsulphonyl, optionally substituted alkenylsulfonyl, optionally substituted arylsulfonyl, and diazonium moieties. Examples of suitable leaving groups include chloro, iodo, bromo, fluoro, methanesulfonyl (mesyl), tosyl, triflate, nitro-phenylsulfonyl (nosyl), and bromo-phenylsulfonyl (brosyl).

For example, in the process of preparing a compound of formula I, $L^3$ is displaced by incoming moiety $R^y$ of $R^y$—H. Thus, if $R^y$—H is e.g., a piperazine, then $L^3$ is a leaving group that is readily displaced by the —NH— moiety in piperazine.

Preferred $L^3$ leaving groups are selected from halogen, optionally substituted arylsulfonyl, or optionally substituted alkylsulphonyl. More preferably, $L^3$ is chloro, iodo, or methanesulfonyl. Most preferably, $L^3$ is chloro.

For example, in the process of preparing a compound of formula II, $L^2$ is displaced by incoming moiety $R^{z1}$-Q of $R^{z1}$-Q-H. Thus, if $R^{z1}$-Q-His, e.g., 3-aminopyrazole, then $L^2$ is a leaving group that is readily displaced by the 3-aminopyrazole.

Preferred $L^2$ leaving groups are selected from halogen, optionally substituted arylsulfonyl, or optionally substituted alkylsulphonyl. More preferably, $L^3$ is chloro, iodo, or fluoro. Most preferably, $L^3$ is chloro.

For example, in the process of preparing a compound of formula III, $L^1$ is displaced by incoming moiety $R^{z2}$-T of $R^{z2}$-T-H. Thus, if $R^{z2}$-T is e.g., an optionally substituted arylthiol, then $L^1$ is a leaving group that is readily displaced by the thio group in the optionally substituted arylthiol.

Preferred $L^1$ leaving groups are selected from halogen, optionally substituted arylsulfonyl, or optionally substituted alkylsulphonyl. More preferably, $L^3$ is chloro, iodo, or methanesulfonyl. Most preferably, $L^3$ is methanesulfonyl.

According to an alternate embodiment, the suitable leaving group may be generated in situ within the reaction medium. For example, $L^3$ in a compound of formula II may be generated in situ from a precursor of that compound of formula II wherein said precursor contains a group readily replaced by $L^3$ in situ. In a specific illustration of such a replacement, said precursor of a compound of formula II contains a group (for example, a chloro group or hydroxyl group) which is replaced in situ by $L^3$, such as an iodo group. The source of the iodo group may be, e.g., sodium iodide. Accordingly, $L^2$ and $L^1$ may also be formed in situ in an analogous manner. Such an in situ generation of a suitable leaving group is well known in the art, e.g., see, "Advanced Organic Chemistry," Jerry March, pp. 430-431, $4^{th}$ Ed., John Wiley and Sons, N.Y. (1992).

According to yet another alternative embodiment, an anion of any of $R^y$ in $R^y$—H, $R^{z1}$-Q in $R^{z1}$-Q-H, or $R^{z2}$-T in $R^{z2}$-T-H may be formed prior to addition to the reaction medium. The preparation of said anion is well known to one of skill in the art. For example, when T is oxygen, the anion of $R^{z2}$-T-H is readily formed by treating $R^{z2}$-T-H with a base, such as sodium hydride. This oxygen anion may then be combined with the compound of formula IV to form a compound of formula III.

According to another embodiment, the reactions described herein are performed at a temperature less than or equal to the reflux temperature of the reaction medium. According to another embodiment, said reaction medium has a temperature less than the boiling point of said suitable solvent or at a temperature attained by refluxing said suitable solvent in said reaction medium. In another embodiment, said reaction medium has a temperature between about 0° C. and about 190° C. According to yet another embodiment, said reaction medium has a temperature between about 40° C. and about 120° C. According to another aspect of the present invention, said reaction medium has a temperature between about 70° C. and about 115° C.

As used herein, the following definitions shall apply unless otherwise indicated.

The term "Aurora" refers to any isoform of the Aurora family of protein kinases, including Aurora-1, Aurora-2, and Aurora-3. The term "Aurora" also refers to isoforms of the Aurora family of protein kinases known as Aurora-A, Aurora-B, and Aurora-C.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$-$C_8$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" or "aryl ring" refers to a monocyclic, bicyclic, or tricyclic ring systems having a total of five to fourteen ring carbon atoms, wherein at least one ring is aromatic and wherein each ring in the system contains three to seven ring members. The term "aryl" may be used interchangeably with the term "aryl ring." Examples include phenyl, indanyl, 1-naphthyl, 2-naphthyl, 1-anthracyl, 2-anthracyl and bicyclo [2.2.2]oct-3-yl.

More preferred ring sizes for aryl rings are as set forth below for the various preferred embodiments of compounds of formula I.

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —$R^o$, —$OR^o$, —$SR^o$, 1,2-methylenedioxy, 1,2-ethylenedioxy, phenyl (Ph) optionally substituted with $R^o$, —O(Ph) optionally substituted with $R^o$, —$CH_2$(Ph) optionally substituted with $R^o$, —$CH_2CH_2$(Ph), optionally substituted with $R^o$, —$NO_2$, —CN, —N($R^o$)$_2$, —$NR^oC(O)$ $R^o$, —$NR^oC(O)N(R^o)_2$, —$NR^oCO_2R^o$, —$NR^oNR^oC(O)R^o$, —$NR^oNR^oC(O)N(R^o)_2$, —$NR^oNR^oCO_2R^o$, —C(O)C(O) $R^o$, —C(O)$CH_2$C(O)$R^o$, —$CO_2R^o$, —C(O)$R^o$, —C(O)N ($R^o$)$_2$), —OC(O)N($R^o$)$_2$, —S(O)$_2R^o$, —$SO_2N(R^o)_2$, —S(O) $R^o$, —$NR^oSO_2N(R^o)_2$, —$NR^oSO_2R^o$, —C(=S)N($R^o$)$_2$, —C(=NH)—N($R^o$)$_2$, or —$(CH_2)_y$NHC(O)$R^o$, wherein each $R^o$ is independently selected from hydrogen, optionally substituted $C_{1-6}$ aliphatic, an unsubstituted 5-6 membered heteroaryl or heterocyclic ring, phenyl, —O(Ph), or —$CH_2$(Ph). Optional substituents on the aliphatic group of $R^o$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$ ($C_{1-4}$ aliphatic), O(halo $C_{1-4}$ aliphatic), or halo $C_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo($C_{1-4}$ aliphatic).

Optional substituents on the nitrogen of a non-aromatic heterocyclic ring are selected from —$R^+$, —N($R^+$)$_2$, —C(O) $R^+$, —$CO_2R^+$, —C(O)C(O)$R^+$, —C(O)$CH_2$C(O)$R^+$, —$SO_2R^+$, —$SO_2N(R)_2$, —C(=S)N(R)$_2$, —C(=NH)—N (R)$_2$, or —$NR^+SO_2R$; wherein $R^+$ is hydrogen, an optionally substituted $C_{1-6}$ aliphatic, optionally substituted phenyl, optionally substituted —O(Ph), optionally substituted —$CH_2$ (Ph), optionally substituted —$CH_2CH_2$(Ph), or an unsubstituted 5-6 membered heteroaryl or heterocyclic ring. Optional substituents on the aliphatic group or the phenyl ring of $R^+$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo ($C_{1-4}$ aliphatic).

The term "alkylidene chain" refers to a straight or branched carbon chain that may be fully saturated or have one or more units of unsaturation and has two points of attachment to the rest of the molecule.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

According to another embodiment, Q of formula I is NH, oxygen, or sulfur.

According to a preferred embodiment, Q of formula I is NR. More preferably, Q of formula I is NH.

According to another preferred embodiment, T of formula I is oxygen or sulfur. More preferably, T of formula I is sulfur.

According to another embodiment, T of formula I is oxygen and the anion of $R^{z2}$-T-H is formed prior to combing with a compound of formula IV to form a compound of formula III.

According to another embodiment, $R^x$ of formula I is U—$R^5$, wherein U is a valence bond, —O—, or —NR—, and $R^5$ is R or Ar.

According to another preferred embodiment $R^x$ of formula I is selected from R, Ar, or —N(R)$_2$. More preferably, $R^x$ of formula I is hydrogen.

According to another preferred embodiment $R^y$ of formula I is selected from —OR$^1$ or —N(R$^1$)$_2$.

According to another embodiment, $R^y$ of formula I is selected from N(R$^1$)$_2$ wherein each R$^1$ is independently selected from R or a 3-7 membered monocyclic or an 8-10 membered bicyclic saturated, partially unsaturated, or fully unsaturated ring having 0-4 heteroatoms independently selected from nitrogen, oxygen, or sulfur. Preferred substituents R$^1$ are selected from —OR$^3$, —SR$^3$, —CN, —NO$_2$, oxo, halogen, —N(R$^3$)$_2$, —C(O)R$^3$, or a 3-6 membered aromatic or non-aromatic ring having zero to two heteroatoms independently selected from nitrogen, oxygen, or sulfur. More preferred substituents on R$^1$ are 5-6 membered non-aromatic rings having 1-2 heteroatoms independently selected from nitrogen, oxygen, or sulfur. Most preferred substituents on the R$^1$C$_{1-4}$ aliphatic group are NH(CH$_3$), NH$_2$, OH, OCH$_3$, morpholinyl, piperidinyl, piperazinyl, pyrrolidinyl, and thiomorpholinyl.

According to another preferred embodiment, R$^y$ of formula I is selected from N(R$^1$)$_2$ wherein each R$^1$ is R such that the two R groups are taken together to form an optionally substituted 4-7 membered non-aromatic ring having up to two additional heteroatoms independently selected from nitrogen, oxygen, or sulfur. Preferred substituents on said ring are selected from —R$^3$, —OR$^3$, —SR$^3$, —CN, —NO$_2$, oxo, halogen, —N(R$^3$)$_2$, —C(O)R$^3$, —CO$_2$R$^3$, —SO$_2$R$^3$, or a 3-6 membered aromatic or non-aromatic ring having zero to two heteroatoms independently selected from nitrogen, oxygen, or sulfur. More preferred substituents said ring are selected from optionally substituted C$_{1-4}$ aliphatic, NH$_2$, NH(C$_{1-4}$ aliphatic), N(C$_{1-4}$ aliphatic)$_2$, optionally substituted phenyl, CO$_2$(C$_{1-4}$ aliphatic), or SO$_2$(C$_{1-4}$ aliphatic). Most preferred substituents on said ring are selected from methyl, ethyl, methylsulfonyl, (CH$_2$)$_2$SO$_2$CH$_3$, cyclopropyl, CH$_2$cyclopropyl, (CH$_2$)$_2$OH, CO$_2$t-butyl, CH$_2$-phenyl, phenyl, NH$_2$, NH(CH$_3$), N(CH$_3$)$_2$, (CH$_2$)$_2$NH$_2$, (CH$_2$)$_2$morpholin-4-yl, (CH$_2$)$_2$N(CH$_3$)$_2$, isopropyl, propyl, t-butyl, (CH$_2$)$_2$CN, or (CH$_2$)$_2$C(O)morpholin-4-yl.

Most preferably, R$^y$ of formula I is pyrrolidin-1-yl, piperidin1-yl, morpholin-4-yl, thiomorpholin-4-yl, piperazin-1-yl, diazepanyl, or tetrahydroisoquinolinyl, wherein each ring is optionally substituted with one or two groups independently selected from methyl, ethyl, methylsulfonyl, (CH$_2$)$_2$SO$_2$CH$_3$, cyclopropyl, CH$_2$cyclopropyl, (CH$_2$)$_2$OH, CO$_2$t-butyl, CH$_2$phenyl, phenyl, NH$_2$, NH(CH$_3$), N(CH$_3$)$_2$, (CH$_2$)$_2$NH$_2$, (CH$_2$)$_2$morpholin-4-yl, (CH$_2$)$_2$N(CH$_3$)$_2$, isopropyl, propyl, t-butyl, (CH$_2$)$_2$CN, or (CH$_2$)$_2$C(O)morpholin-4-yl.

According to another embodiment R$^{z1}$ of formula I is a 3-7 membered monocyclic or an 8-10 membered bicyclic saturated, partially unsaturated, or fully unsaturated ring having 0-4 heteroatoms independently selected from oxygen, nitrogen or sulfur, wherein said ring is optionally and independently substituted by up to three substituents selected from —R$^3$, —OR$^3$, —SR$^3$, —CN, —NO$_2$, oxo, halogen, —N(R$^3$)$_2$, —C(O)R$^3$, —OC(O)R$^3$, —CO$_2$R$^3$, —SO$_2$R$^3$, —SO$_2$N(R$^3$)$_2$, —N(R$^3$)SO$_2$R$^3$, —C(O)NR(R$^3$), —C(O)N(R$^3$)$_2$, —OC(O)NR(R$^3$), —OC(O)N(R$^3$)$_2$, —NR$^3$C(O)R$^3$, —NR$^3$C(O)N(R$^3$)$_2$, or —NR$^3$CO$_2$R$^3$.

According to another embodiment, R$^{z1}$ of formula I is a 5-6 membered monocyclic or an 8-10 membered bicyclic saturated, partially unsaturated, or fully unsaturated ring having 1-4 heteroatoms independently selected from oxygen, nitrogen or sulfur, wherein said ring is optionally and independently substituted by up to three substituents selected from —R$^3$, —OR$^3$, —SR$^3$, —CN, —NO$_2$, oxo, halogen, —N(R$^3$)$_2$, —C(O)R$^3$, —OC(O)R$^3$, —CO$_2$R$^3$, —SO$_2$R$^3$, —SO$_2$N(R$^3$)$_2$, —N(R$^3$)SO$_2$R$^3$, —C(O)NR(R$^3$), —C(O)N(R$^3$)$_2$,—OC(O)NR(R$^3$), —OC(O)N(R$^3$)$_2$, —NR$^3$C(O)R$^3$, —NR$^3$C(O)N(R$^3$)$_2$, or —NR$^3$CO$_2$R$^3$.

According to a more preferred embodiment, R$^{z1}$ of formula I is a five or six membered fully unsaturated ring having 1-3 heteroatoms independently selected from nitrogen, oxygen, or sulfur, wherein said ring is optionally and independently substituted by up to three substituents selected from —R$^3$, —OR$^3$, —SR$^3$, —CN, —NO$_2$, oxo, halogen, —N(R$^3$)$_2$, —C(O)R$^3$, —OC(O)R$^3$, —CO$_2$R$^3$, —SO$_2$R$^3$, —SO$_2$N(R$^3$)$_2$, —N(R$^3$)SO$_2$R$^3$, —C(O)NR(R$^3$), —C(O)N(R$^3$)$_2$, —OC(O)NR(R$^3$), —OC(O)N(R$^3$)$_2$, —NR$^3$C(O)R$^3$, —NR$^3$C(O)N(R$^3$)$_2$, or —NR$^3$CO$_2$R$^3$.

Preferred R$^{z1}$ rings of formula I are optionally substituted rings selected from pyrazole or any one of the following 5-6 membered rings:

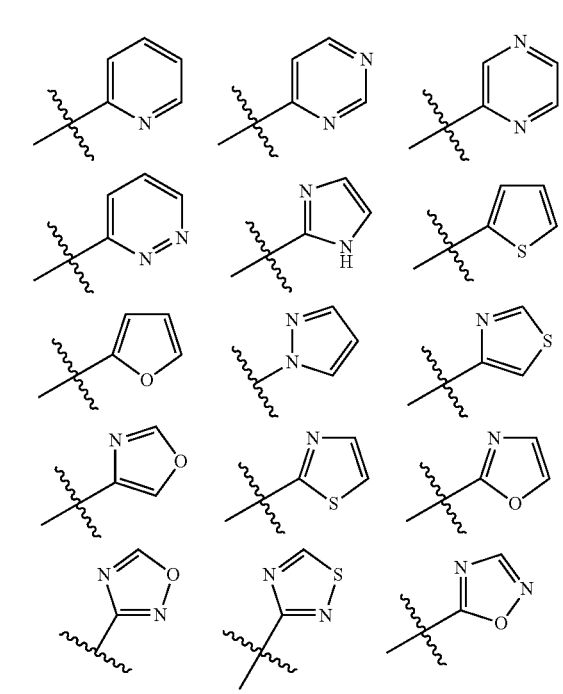

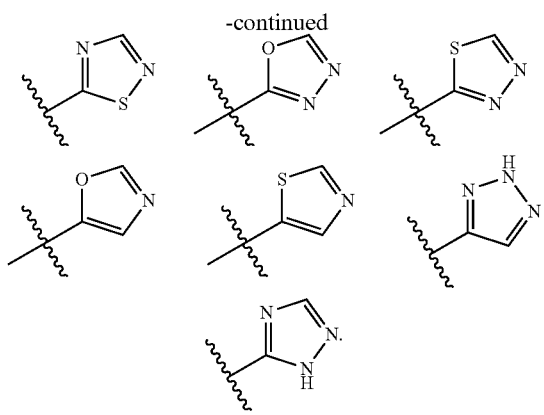

Most preferably, $R^{z1}$ of formula I is a pyrazole ring having up to three substituents as defined above.

According to another preferred embodiment $R^{z1}$ of formula I has up to two substituents, wherein said substituents are as set forth above. More preferably, $R^{z1}$ of formula I has one substituent, wherein said substituent is as set forth above.

Preferred substituents on the $R^{z1}$ moiety of formula I are —$N(R^3)_2$, —$OR^3$, Ar, or an optionally substituted $C_1$-$C_4$ aliphatic group, wherein Ar is an optionally substituted 5-6 membered saturated, partially unsaturated, or fully unsaturated ring having 0-4 heteroatoms independently selected from nitrogen, oxygen, or sulfur. An even more preferred substituents on the $R^{z1}$ moiety of formula I is a $C_1$-$C_4$ aliphatic group. Most preferred substituents on the $R^{z1}$ moiety of formula I are selected from methyl, ethyl, propyl, isopropyl, t-butyl, cyclopropyl, or phenyl.

According to another embodiment $R^{z1}$ of formula I is a $C_{1-6}$ aliphatic group substituted with 0-4 $R^2$ groups. Preferably, $R^{z1}$ is substituted with 0-3 $R^2$ groups, wherein each $R^2$ is independently selected from $R^3$, oxo, halogen, $N(R^3)_2$, CN, or $CO_2R^3$.

According to a preferred embodiment, $R^{z2}$ of formula I is a 5-6 membered monocyclic or an 8-10 membered bicyclic saturated, partially unsaturated, or fully unsaturated ring having 0-4 heteroatoms independently selected from nitrogen, oxygen or sulfur, wherein said ring is optionally substituted by up to three substituents independently selected from —$R^3$, —$OR^3$, —$SR^3$, —CN, —$NO_2$, oxo, halogen, —$N(R^3)_2$, —$C(O)R^3$, —$OC(O)R^3$, —$CO_2R^3$, —$SO_2R^3$, —$SO_2N(R^3)_2$, —$N(R^3)SO_2R^3$, —$C(O)NR(R^3)$, —$C(O)N(R^3)_2$, —$OC(O)NR(R^3)$, —$OC(O)N(R^3)_2$, —$NR^3C(O)R^3$, —$NR^3C(O)N(R^3)_2$, or —$NR^3CO_2R^3$.

More preferably, $R^{z2}$ of formula I is selected from an optionally substituted ring selected from a 5-6 membered monocyclic or an 9-10 membered bicyclic saturated, partially unsaturated, or fully unsaturated ring having 0-4 heteroatoms independently selected from nitrogen, oxygen or sulfur; wherein said ring is optionally substituted by up to three substituents independently selected as set forth above. Most preferably, $R^{z2}$ of formula I is selected from phenyl, imidazolyl, pyrazolyl, pyridyl, pyridazinyl, pyrazinyl, naphthyl, tetrahydronaphthyl, benzimidazolyl, benzthiazolyl, quinolinyl, quinazolinyl, benzodioxinyl, isobenzofuran, indanyl, indolyl, indolinyl, indazolyl, or isoquinolinyl, wherein the $R^{z2}$ moiety of formula I is optionally and independently substituted with up to three substituents as set forth above.

Preferred substituents on $R^{z2}$ of formula I, when present, are independently selected from halogen, —CN, —$NO_2$, —$C(O)R^3$, —$CO_2R^3$, —$C(O)NR(R^3)$, —$NR^3C(O)R^3$, —$N(R^3)_2$, —$N(R^3)SO_2R^3$, —$NR^3C(O)N(R^3)_2$, or —$NR^3CO_2R^3$. More preferred substituents on the $R^{z2}$ moiety of formula I are independently selected from —Cl, —Br, —F, —CN, —$CF_3$, —COOH, —CONHMe, —CONHEt, —$NH_2$, —NHAc, —$NHSO_2Me$, —$NHSO_2Et$, —$NHSO_2$(n-propyl), —$NHSO_2$(isopropyl), —NHCOEt, —$NHCOCH_2NHCH_3$, —$NHCOCH_2N(CO_2$-t-Bu$)CH_3$, —$NHCOCH_2N(CH_3)_2$, —$NHCOCH_2CH_2N(CH_3)_2$, —$NHCOCH_2CH_2CH_2N(CH_3)_2$, —NHCO(cyclopropyl), —NHCO(isopropyl), —NHCO(isobutyl), —$NHCOCH_2$(morpholin-4-yl), —$NHCOCH_2CH_2$(morpholin-4-yl), —$NHCOCH_2CH_2CH_2$(morpholin-4-yl), —$NHCO_2$(t-butyl), —NH(cyclohexyl), —NHMe, —$NMe_2$, —OH, —OMe, methyl, ethyl, cyclopropyl, isopropyl, or t-butyl.

According to another preferred embodiment $R^{z2}$ of formula I has up to two substituents, wherein said substituents are as set forth above. More preferably, $R^{z2}$ of formula I has one substituent, wherein said substituent is as set forth above. Most preferably, $R^{z2}$ of formula I has one substituent selected from —$NR^3C(O)R^3$, wherein each $R^3$ is independently selected from R or Ar and wherein R is hydrogen or an optionally substituted $C_{1-4}$ aliphatic group.

According to another embodiment, $R^{z2}$ of formula I is $C_{1-6}$ aliphatic group substituted with 0-3 groups independently selected from halogen, oxo, —CN, —$NO_2$, —$C(O)R^3$, —$CO_2R^3$, —$C(O)NR(R^3)$, —$NR^3C(O)R^3$, —$N(R^3)_2$, —$N(R^3)SO_2R^3$, —$NR^3C(O)N(R^3)_2$, or —$NR^3CO_2R^3$. More preferably, $R^{z2}$ of formula I is a $C_{1-4}$ aliphatic group substituted with 0-3 groups independently selected from halogen, —CN, —$NO_2$, —$C(O)R^3$, —$CO_2R^3$, —$N(R^3)_2$, or —$NR^3CO_2R^3$.

Preferred embodiments of $R^x$, T, Q, $R^{z1}$, and $R^{z2}$ in formula II are as set forth for these moieties in formula I.

Preferred embodiments of the $R^y$ moiety of $R^y$—H are as set forth for the $R^y$ group in formula I.

Preferred embodiments of $R^x$, $L^3$, T, and $R^{z2}$ in formula III are as set forth for these moieties in formula I.

Preferred embodiments of the Q and $R^{z1}$ moieties of $R^{z1}$-Q-H are as set forth for these moieties in formula I.

Preferred embodiments $R^x$, $L^3$, $L^2$ and Q in formula IV are as set forth for these moieties in formula I.

Preferred embodiments of $R^{z2}$ and T in $R^{z2}$-T-H are as set forth for these moieties in formula I.

Preferably $R^x$ in the processes of the present invention is other than a suitable leaving group.

Preferred compounds of formula I, prepared using the processes of the present invention, have formula I':

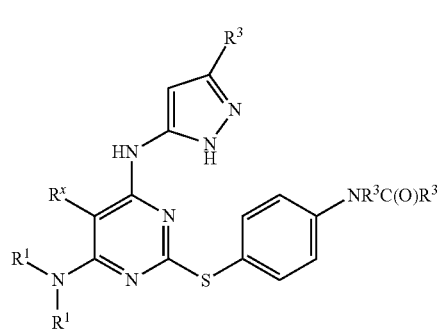

or a pharmaceutically acceptable derivative or salt thereof, wherein $R^1$ and $R^3$ are as defined above.

Preferred $R^1$ groups of formula I' are independently selected from R, wherein R is hydrogen or an optionally substituted $C_{1-4}$ aliphatic group. Preferred substituents on the $C_{1-4}$ aliphatic group of the $R^1$ moiety of formula I' are selected from $—OR^3$, $—SR^3$, —CN, $—NO_2$, oxo, halogen, $—N(R^3)_2$, $—C(O)R^3$, or a 3-6 membered aromatic or non-aromatic ring having zero to two heteroatoms independently selected from nitrogen, oxygen, or sulfur.

More preferred substituents on the $C_{1-4}$ aliphatic group of the $R^1$ moiety of formula I' are 5-6 membered non-aromatic rings having 1-2 heteroatoms independently selected from nitrogen, oxygen, or sulfur. Most preferred substituents on the $R^1 C_{1-4}$ aliphatic group of the $R^1$ moiety of formula I' are $NH(CH_3)$, $NH_2$, OH, $OCH_3$, morpholinyl, piperidinyl, piperazinyl, pyrrolidinyl, and thiomorpholinyl.

According to another preferred embodiment, each $R^1$ of formula I' is R such that the two R groups are taken together to form an optionally substituted 4-7 membered non-aromatic ring having up to two additional heteroatoms independently selected from nitrogen, oxygen, or sulfur. Preferred substituents on said ring are selected from $—R^3$, $—OR^3$, $—SR^3$, —CN, $—NO_2$, oxo, halogen, $—N(R^3)_2$, $—C(O)R^3$, $—CO_2R^3$, $—SO_2R^3$, or a 3-6 membered aromatic or non-aromatic ring having zero to two heteroatoms independently selected from nitrogen, oxygen, or sulfur. More preferred substituents said ring are selected from optionally substituted $C_{1-4}$ aliphatic, $NH_2$, $NH(C_{1-4}$ aliphatic), $N(C_{1-4}$ aliphatic$)_2$, optionally substituted phenyl, $CO_2(C_{1-4}$ aliphatic), or $SO_2$ ($C_{1-4}$ aliphatic). Most preferred substituents on said ring are selected from methyl, ethyl, methylsulfonyl, $(CH_2)_2SO_2CH_3$, cyclopropyl, $CH_2$cyclopropyl, $(CH_2)_2OH$, $CO_2$t-butyl, $CH_2$phenyl, phenyl, $NH_2$, $NH(CH_3)$, $N(CH_3)_2$, $(CH_2)_2NH_2$, $(CH_2)_2$morpholin-4-yl, $(CH_2)_2N(CH_3)_2$, isopropyl, propyl, t-butyl, $(CH_2)_2CN$, or $(CH_2)_2C(O)$morpholin-4-yl.

More preferably, the ring formed by $N(R^1)_2$ of formula I' is pyrrolidinyl, piperidinyl, morpholin-4-yl, thiomorpholin-4-yl, piperazin-1-yl, diazepanyl, or tetrahydroisoquinolinyl, wherein each ring is optionally substituted with one or two groups independently selected from methyl, ethyl, methylsulfonyl, $(CH_2)_2SO_2CH_3$, cyclopropyl, $CH_2$cyclopropyl, $(CH_2)_2OH$, $CO_2$t-butyl, $CH_2$phenyl, phenyl, $NH_2$, $NH(CH_3)$, $N(CH_3)_2$, $(CH_2)_2NH_2$, $(CH_2)_2$morpholin-4-yl, $(CH_2)_2N$ $(CH_3)_2$, isopropyl, propyl, t-butyl, $(CH_2)_2CN$, or $(CH_2)_2C(O)$morpholin-4-yl.

More preferred compounds within compounds of formula I prepared using the processes of the present invention have formula V:

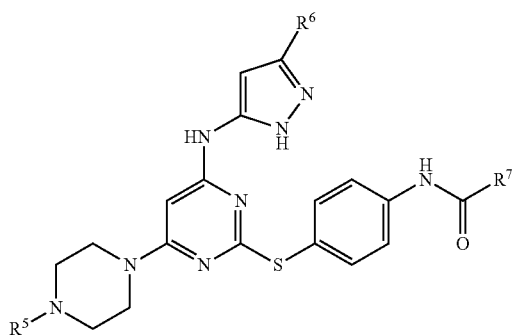

or a pharmaceutically acceptable derivative or salt thereof, wherein:

$R^5$ is selected from hydrogen or $C_{1-4}$ aliphatic;

$R^6$ is selected from $C_{1-3}$ aliphatic; and $R^7$ is selected from $C_{1-4}$ aliphatic.

Preferred $R^5$ groups of formula V are selected from hydrogen, methyl, ethyl, t-butyl, propyl, cyclopropyl, cyclopropylmethyl, or isopropyl. More preferred $R^5$ groups of formula V are selected from hydrogen or methyl. Most preferably $R^5$ of formula V is methyl.

Preferred $R^6$ groups of formula V are selected from methyl, ethyl, or cyclopropyl. More preferred $R^6$ groups of formula V are methyl of cyclopropyl. Most preferably, $R^6$ of formula V is methyl.

Preferred $R^7$ groups of formula V are selected from methyl, ethyl, t-butyl, or cyclopropyl. More preferred $R^7$ groups of formula V are selected from ethyl or cyclopropyl. Most preferably, $R^7$ of formula V is cyclopropyl.

According to another embodiment, the present invention relates to a compound of formula V:

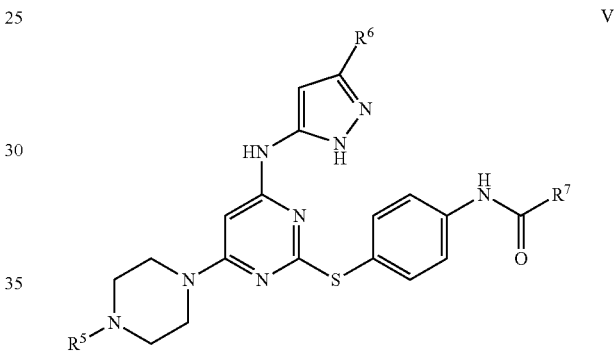

or a pharmaceutically acceptable derivative or salt thereof, wherein:

$R^5$ is selected from hydrogen or $C_{1-4}$ aliphatic;

$R^6$ is selected from $C_{1-3}$ aliphatic; and $R^7$ is selected from $C_{1-4}$ aliphatic; provided that said compound is other than N-{4-[4-(4-methyl-piperazin-1-yl)-6-(5-methyl-2H-pyrazol-3-ylamino)-pyrimidin-2-ylsulfanyl]-phenyl}-propionamide.

Preferred $R^5$ groups of formula V are selected from hydrogen, methyl, ethyl, t-butyl, or isopropyl. More preferred $R^5$ groups of formula V are selected from hydrogen or methyl. Most preferably $R^5$ of formula V is methyl.

Preferred $R^6$ groups of formula V are selected from methyl, ethyl, or cyclopropyl. More preferred $R^6$ groups of formula V are methyl of cyclopropyl. Most preferably, $R^6$ of formula V is methyl.

Preferred $R^7$ groups of formula V are selected from methyl, ethyl, t-butyl, or cyclopropyl. More preferred $R^7$ groups of formula V are selected from ethyl or cyclopropyl. Most preferably, $R^7$ of formula V is cyclopropyl.

Compounds of formula V fall within the genus of compounds described in PCT publication WO 02/057259. However, applicants have discovered that the present compounds have surprising and unexpectedly increased potency as inhibitors of Aurora protein kinase and/or FLT-3 protein kinase.

Exemplary structures of formula V are set forth in Table 1 below.
TABLE 1
| No. V- | Structure |
|---|---|
| 1 | 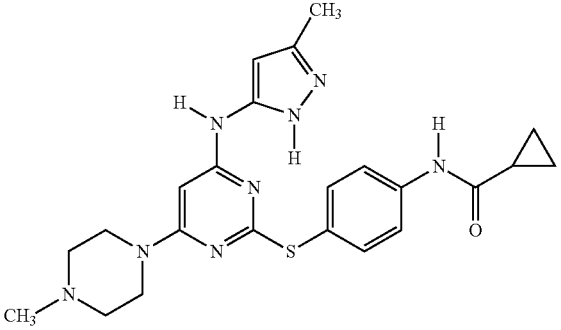 [SMILES: Cc1cc(Nc2cc(N3CCN(C)CC3)nc(Sc3ccc(NC(=O)C4CC4)cc3)n2)[nH]n1] |
| 2 | 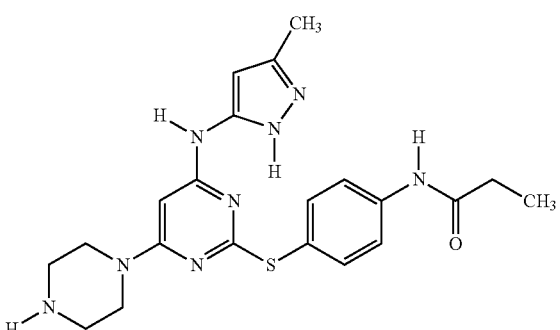 |
| 3 | 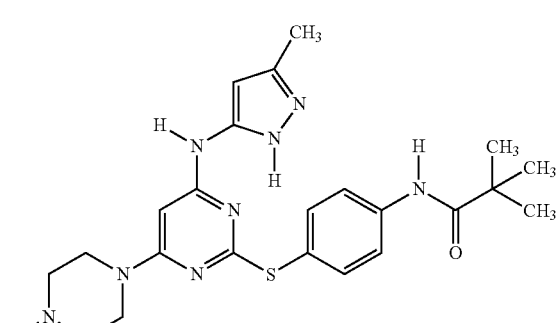 |
| 4 | 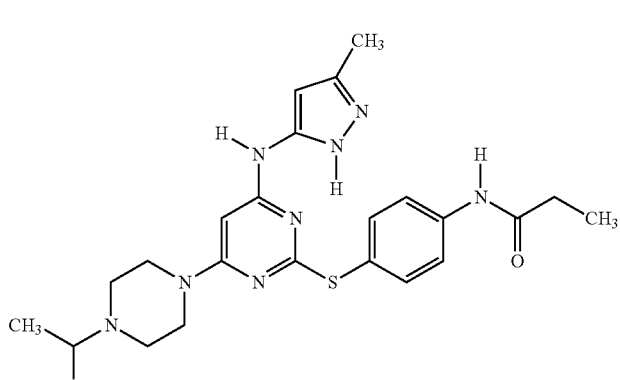 |

TABLE 1-continued
| No. V- | Structure |
|---|---|
| 5 | 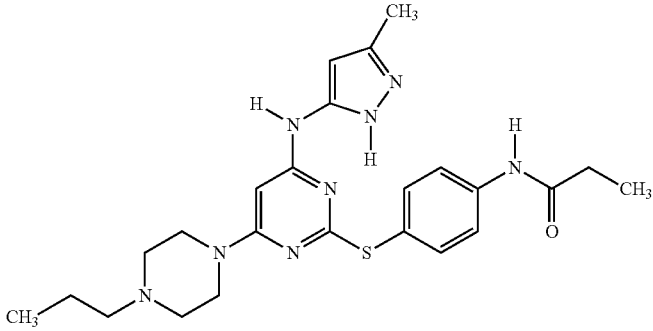 [SMILES: CCCN1CCN(c2cc(Nc3cc(C)n[nH]3)nc(Sc3ccc(NC(=O)CC)cc3)n2)CC1] |
| 6 | 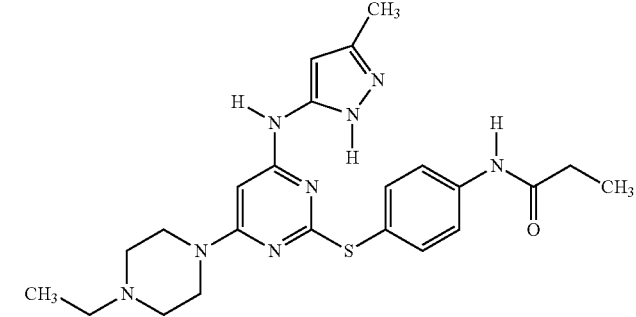 [SMILES: CCC(=O)Nc1ccc(Sc2nc(Nc3cc(C)n[nH]3)cc(N3CCN(CC)CC3)n2)cc1] |
| 7 | 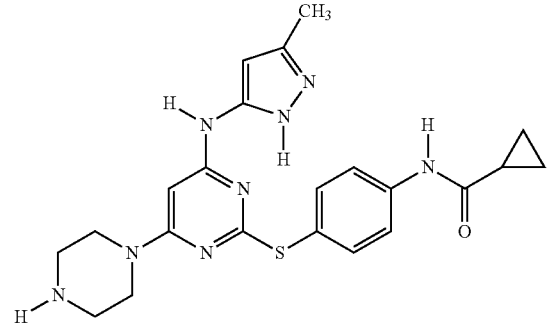 [SMILES: Cc1cc(Nc2cc(N3CCNCC3)nc(Sc3ccc(NC(=O)C4CC4)cc3)n2)[nH]n1] |
| 8 | 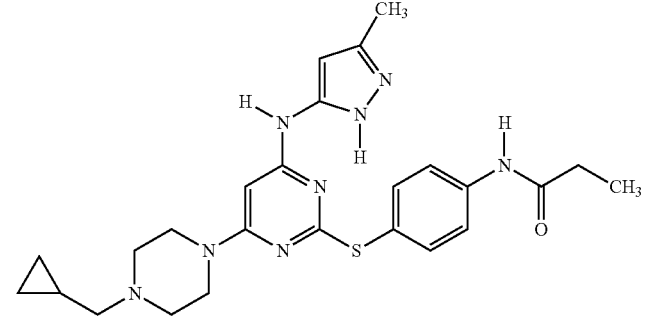 [SMILES: CCC(=O)Nc1ccc(Sc2nc(Nc3cc(C)n[nH]3)cc(N3CCN(CC4CC4)CC3)n2)cc1] |

TABLE 1-continued
| No. V- | Structure |
|---|---|
| 9 | 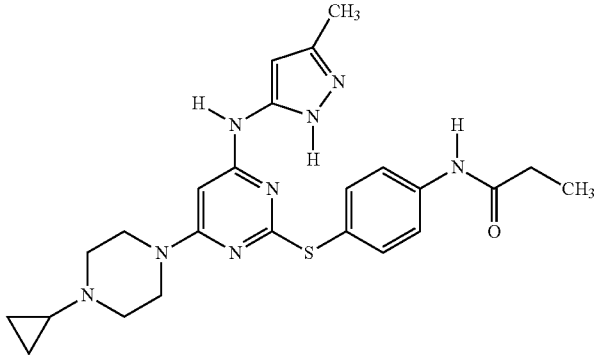 [SMILES: CCC(=O)Nc1ccc(Sc2nc(Nc3cc(C)n[nH]3)cc(N3CCN(C4CC4)CC3)n2)cc1] |
| 10 | 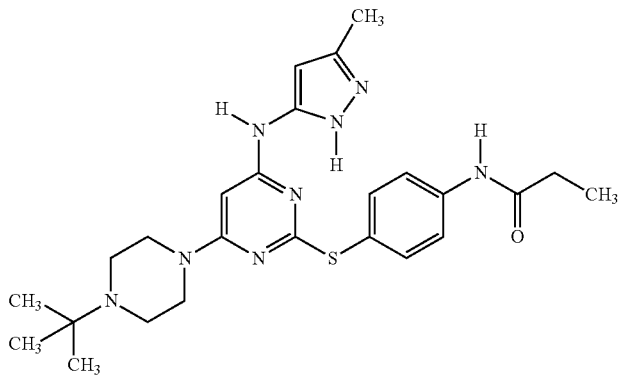 [SMILES: CCC(=O)Nc1ccc(Sc2nc(Nc3cc(C)n[nH]3)cc(N3CCN(C(C)(C)C)CC3)n2)cc1] |
| 11 | 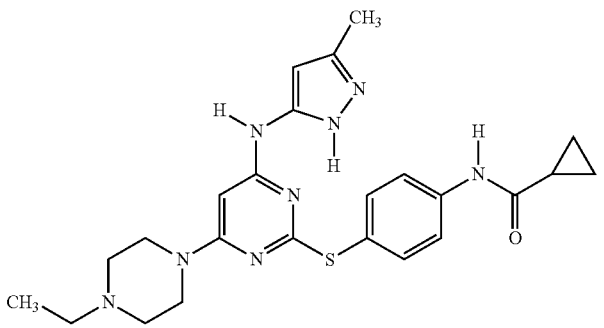 [SMILES: CCN1CCN(c2cc(Nc3cc(C)n[nH]3)nc(Sc3ccc(NC(=O)C4CC4)cc3)n2)CC1] |
| 12 | 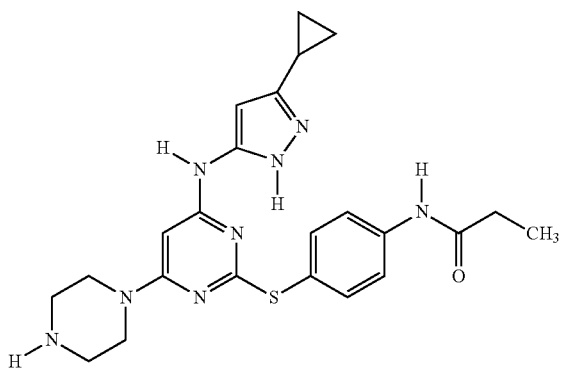 [SMILES: CCC(=O)Nc1ccc(Sc2nc(Nc3cc(C4CC4)n[nH]3)cc(N3CCNCC3)n2)cc1] |

TABLE 1-continued

| No. V- | Structure |
|---|---|
| 13 | (structure) |
| 14 | (structure) |
| 15 | (structure) |
| 16 | (structure) |

TABLE 1-continued
| No. V- | Structure |
|---|---|
| 17 | 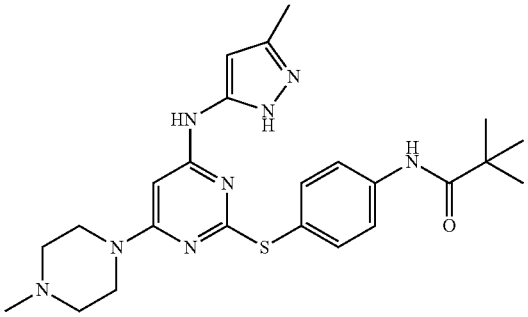 |
| 18 | 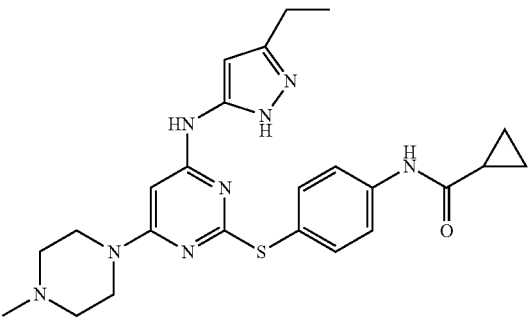 [SMILES: CCc1cc(Nc2cc(N3CCN(C)CC3)nc(Sc3ccc(NC(=O)C4CC4)cc3)n2)[nH]n1] |
| 19 | 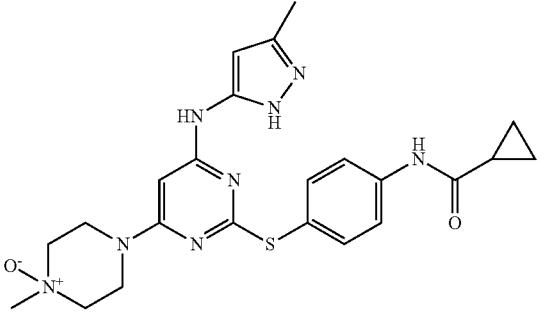 [SMILES: Cc1cc(Nc2cc(N3CC[N+](C)([O-])CC3)nc(Sc3ccc(NC(=O)C4CC4)cc3)n2)[nH]n1] |
| 20 | 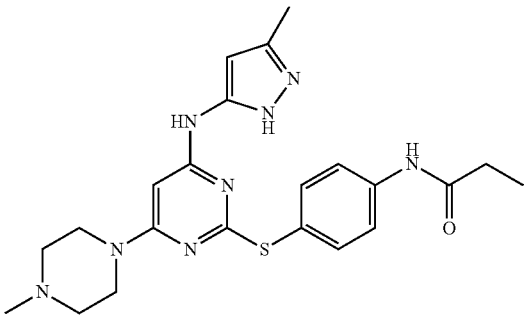 [SMILES: CCC(=O)Nc1ccc(Sc2nc(Nc3cc(C)n[nH]3)cc(N3CCN(C)CC3)n2)cc1] |

Other exemplary compounds of formula I prepared according to the processes of the present invention are set forth in Table 2 below.
TABLE 2
Exemplary Compounds of Formula I
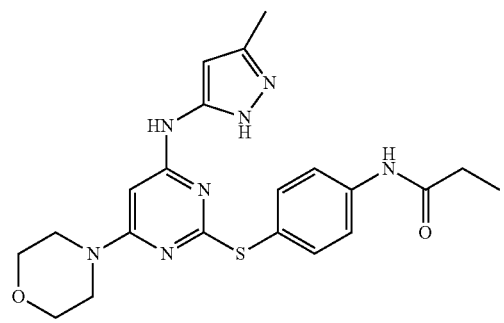 [SMILES: CCC(=O)Nc1ccc(Sc2nc(Nc3cc(C)n[nH]3)cc(N3CCOCC3)n2)cc1]
I-1
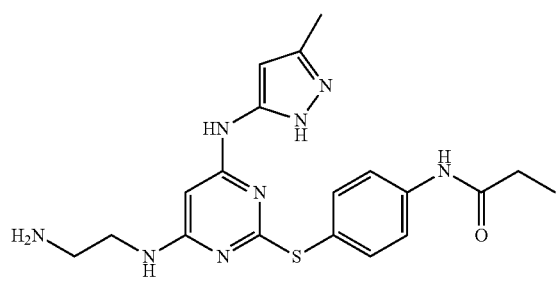 [SMILES: CCC(=O)Nc1ccc(Sc2nc(NCCN)cc(Nc3cc(C)n[nH]3)n2)cc1]
I-2
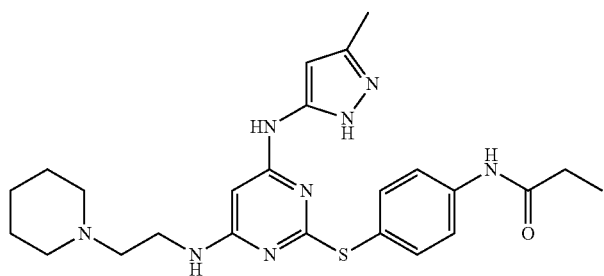 [SMILES: CCC(=O)Nc1ccc(Sc2nc(NCCN3CCCCC3)cc(Nc3cc(C)n[nH]3)n2)cc1]
I-3
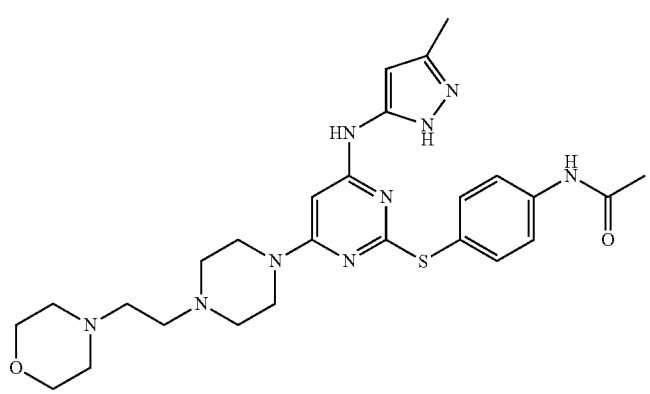 [SMILES: CC(=O)Nc1ccc(Sc2nc(Nc3cc(C)n[nH]3)cc(N3CCN(CCN4CCOCC4)CC3)n2)cc1]
I-4

TABLE 2-continued
Exemplary Compounds of Formula I
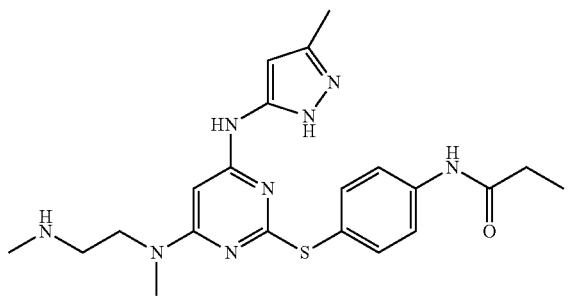 [SMILES: CCC(=O)Nc1ccc(Sc2nc(Nc3cc(C)n[nH]3)cc(N(C)CCNC)n2)cc1]
I-5
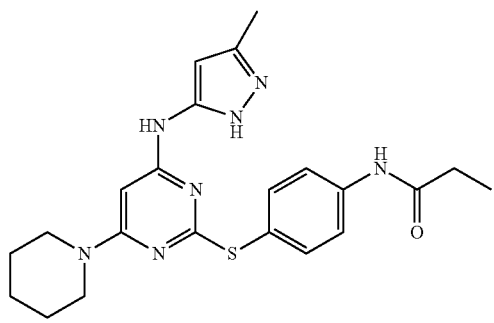 [SMILES: CCC(=O)Nc1ccc(Sc2nc(Nc3cc(C)n[nH]3)cc(N3CCCCC3)n2)cc1]
I-6
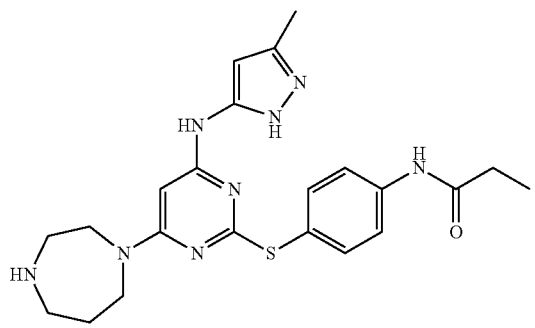 [SMILES: CCC(=O)Nc1ccc(Sc2nc(Nc3cc(C)n[nH]3)cc(N3CCCNCC3)n2)cc1]
I-7
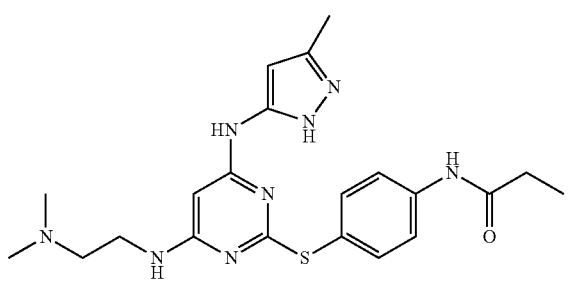 [SMILES: CCC(=O)Nc1ccc(Sc2nc(NCCN(C)C)cc(Nc3cc(C)n[nH]3)n2)cc1]
I-8
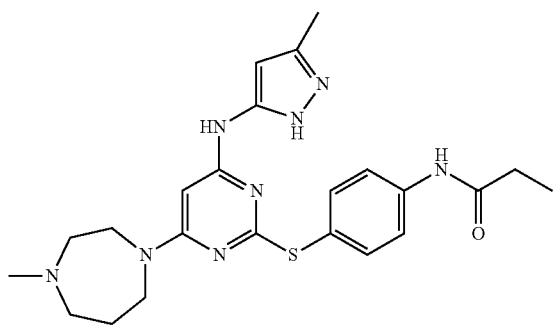 [SMILES: CCC(=O)Nc1ccc(Sc2nc(Nc3cc(C)n[nH]3)cc(N3CCCN(C)CC3)n2)cc1]
I-9

TABLE 2-continued
Exemplary Compounds of Formula I
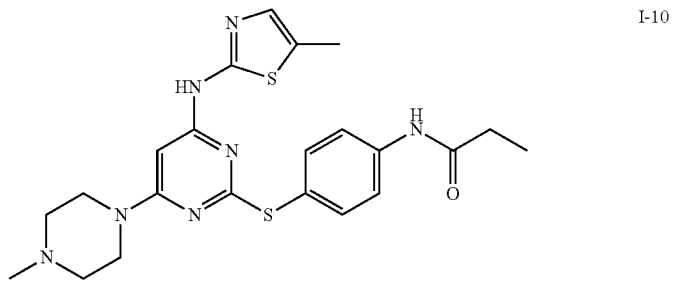
I-10
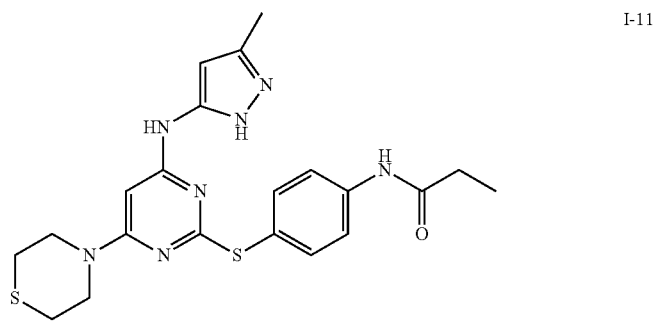
I-11
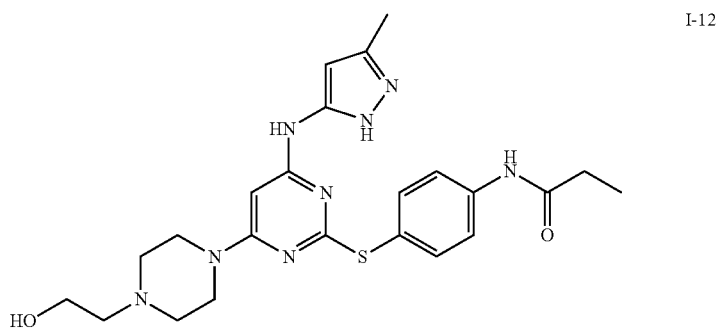
I-12
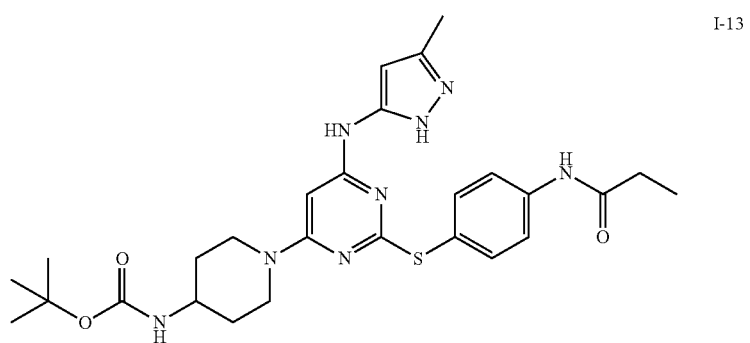
I-13

TABLE 2-continued
Exemplary Compounds of Formula I
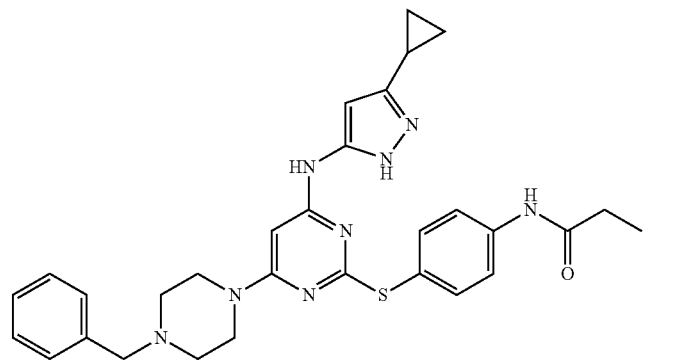 [SMILES: CCC(=O)Nc1ccc(Sc2nc(Nc3cc(C4CC4)n[nH]3)cc(N3CCN(Cc4ccccc4)CC3)n2)cc1]
I-14
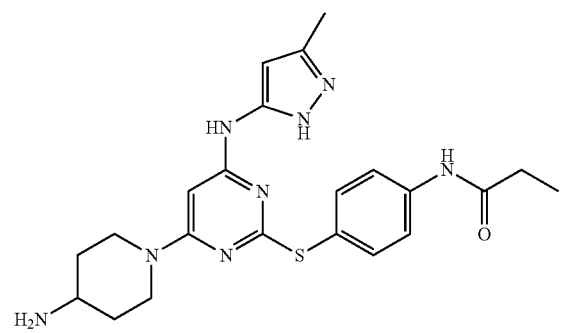 [SMILES: CCC(=O)Nc1ccc(Sc2nc(Nc3cc(C)n[nH]3)cc(N3CCC(N)CC3)n2)cc1]
I-15
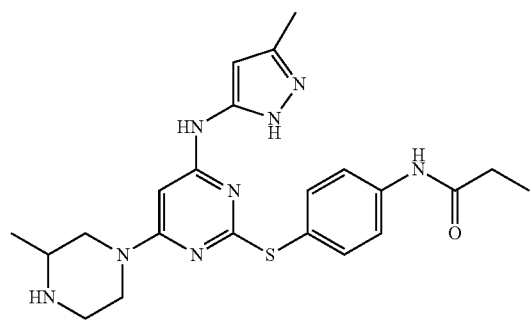 [SMILES: CCC(=O)Nc1ccc(Sc2nc(Nc3cc(C)n[nH]3)cc(N3CCNC(C)C3)n2)cc1]
I-16
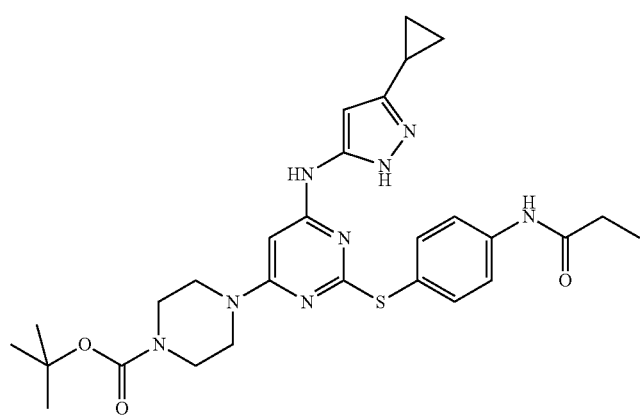 [SMILES: CCC(=O)Nc1ccc(Sc2nc(Nc3cc(C4CC4)n[nH]3)cc(N3CCN(C(=O)OC(C)(C)C)CC3)n2)cc1]
I-17

TABLE 2-continued
Exemplary Compounds of Formula I
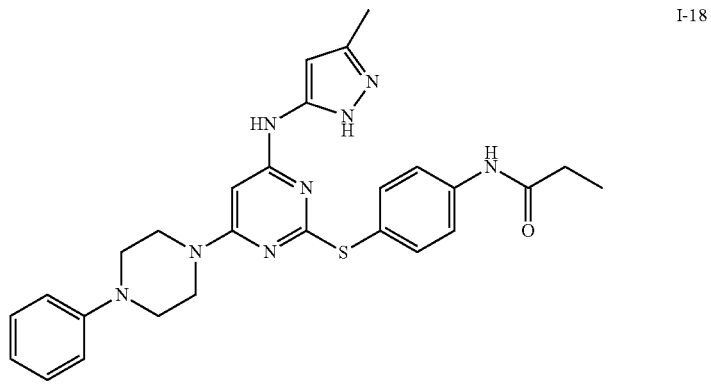
I-18
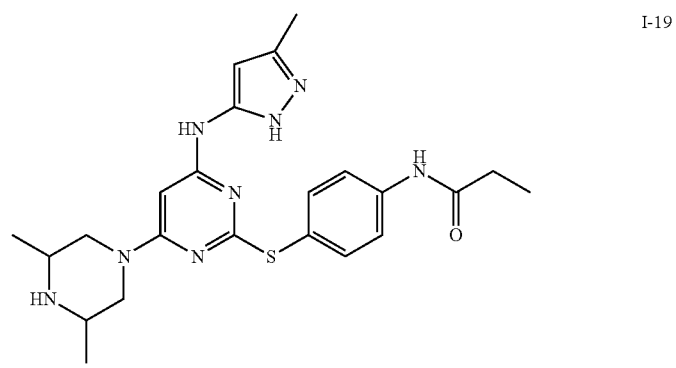
I-19
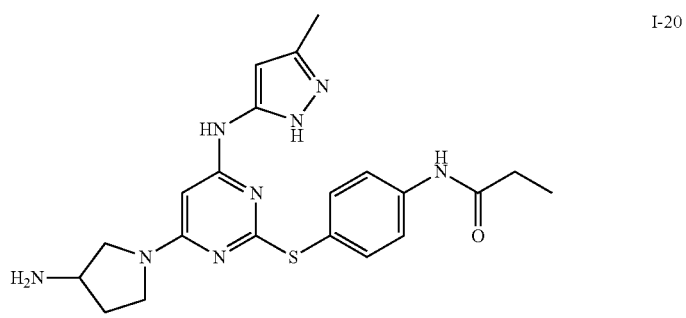
I-20
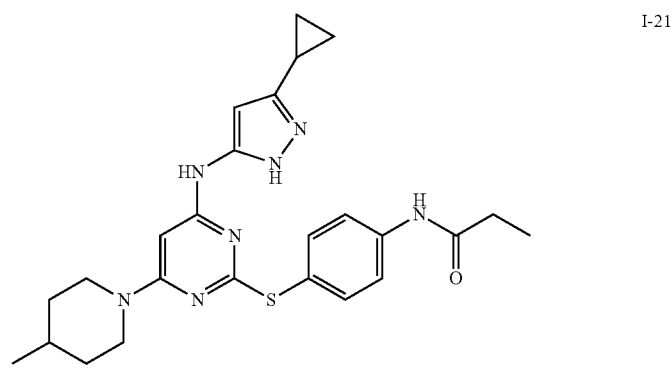
I-21

TABLE 2-continued
Exemplary Compounds of Formula I
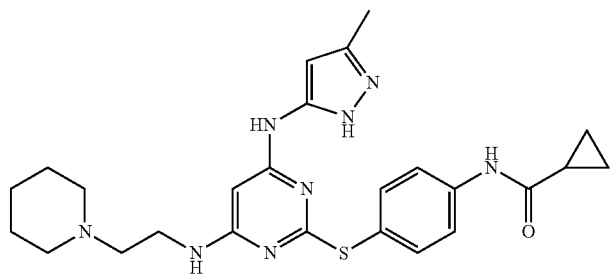 [SMILES: Cc1cc(Nc2cc(NCCN3CCCCC3)nc(Sc3ccc(NC(=O)C4CC4)cc3)n2)[nH]n1]
I-22
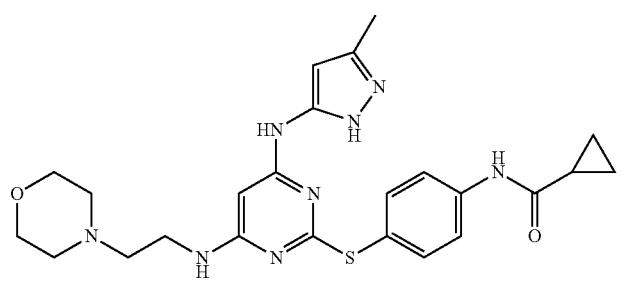 [SMILES: Cc1cc(Nc2cc(NCCN3CCOCC3)nc(Sc3ccc(NC(=O)C4CC4)cc3)n2)[nH]n1]
I-23
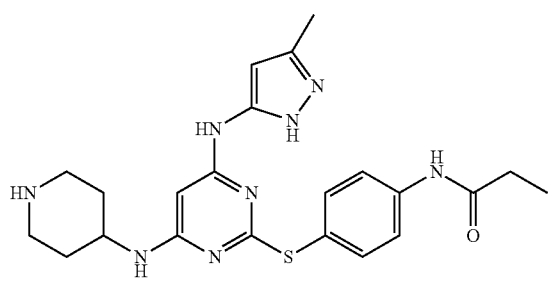 [SMILES: CCC(=O)Nc1ccc(Sc2nc(Nc3cc(C)n[nH]3)cc(NC3CCNCC3)n2)cc1]
I-24
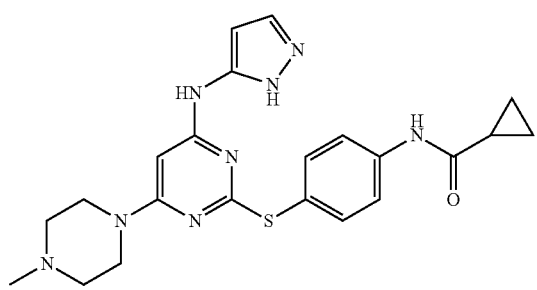 [SMILES: CN1CCN(c2cc(Nc3ccn[nH]3)nc(Sc3ccc(NC(=O)C4CC4)cc3)n2)CC1]
I-25
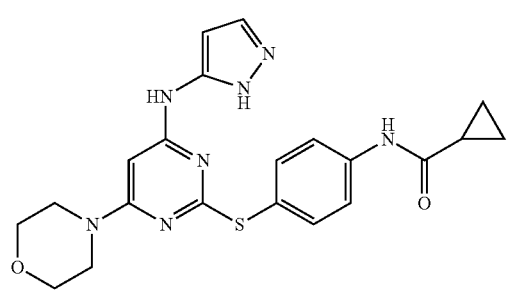 [SMILES: O=C(Nc1ccc(Sc2nc(Nc3ccn[nH]3)cc(N3CCOCC3)n2)cc1)C1CC1]
I-26

TABLE 2-continued
Exemplary Compounds of Formula I
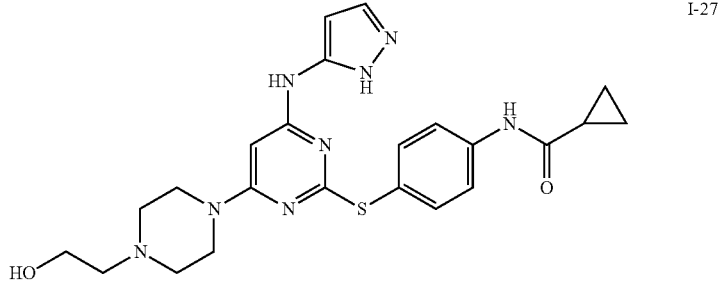
I-27
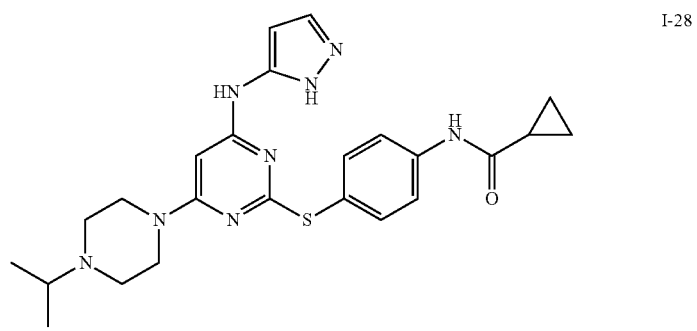
I-28
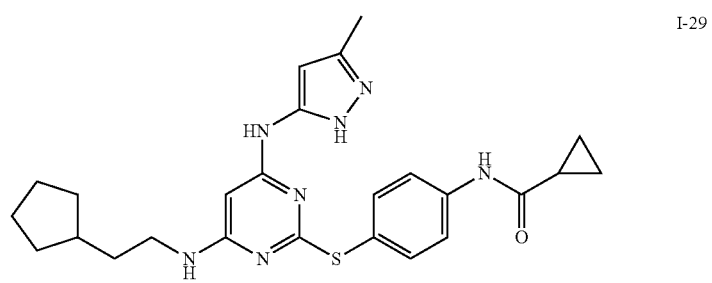
I-29
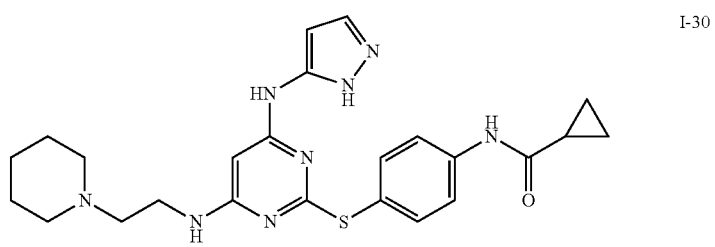
I-30
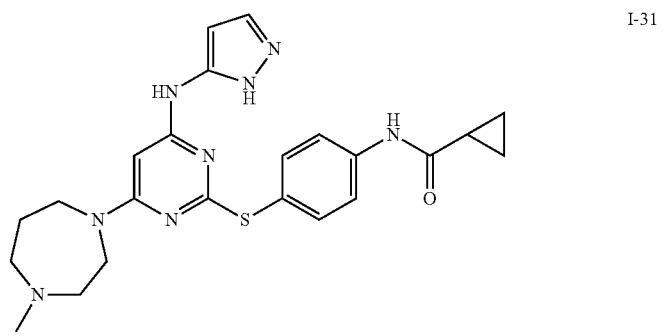
I-31

TABLE 2-continued
Exemplary Compounds of Formula I
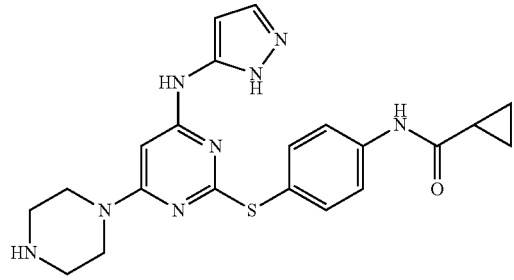 [SMILES: O=C(Nc1ccc(Sc2nc(Nc3ccn[nH]3)cc(N3CCNCC3)n2)cc1)C1CC1]
I-32
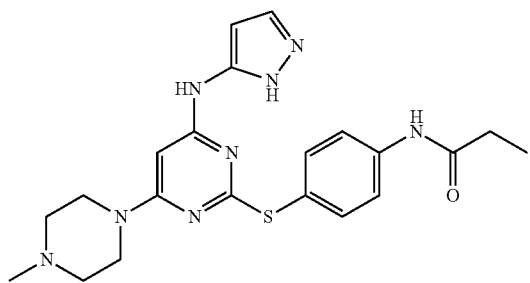 [SMILES: CCC(=O)Nc1ccc(Sc2nc(Nc3ccn[nH]3)cc(N3CCN(C)CC3)n2)cc1]
I-33
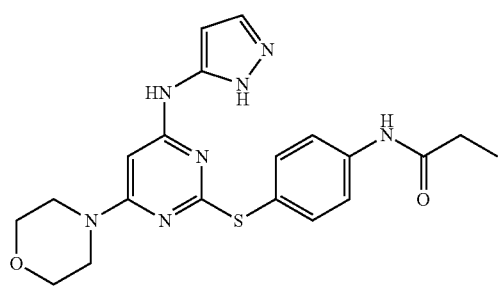 [SMILES: CCC(=O)Nc1ccc(Sc2nc(Nc3ccn[nH]3)cc(N3CCOCC3)n2)cc1]
I-34
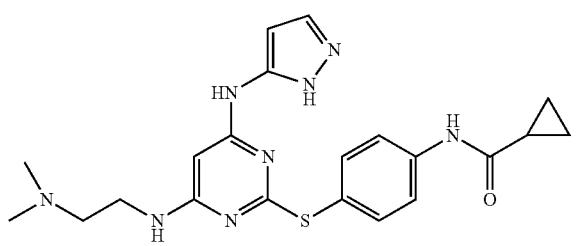 [SMILES: CN(C)CCNc1cc(Nc2ccn[nH]2)nc(Sc2ccc(NC(=O)C3CC3)cc2)n1]
I-35
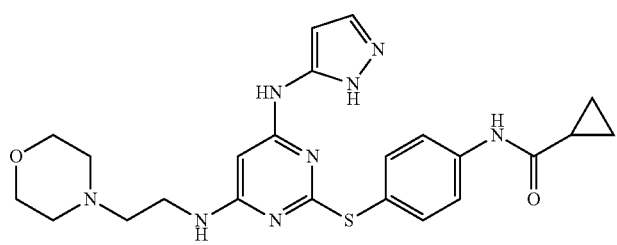 [SMILES: O=C(Nc1ccc(Sc2nc(NCCN3CCOCC3)cc(Nc3ccn[nH]3)n2)cc1)C1CC1]
I-36

TABLE 2-continued
Exemplary Compounds of Formula I
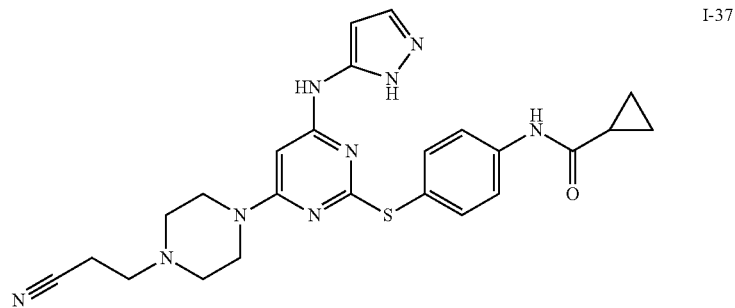
I-37
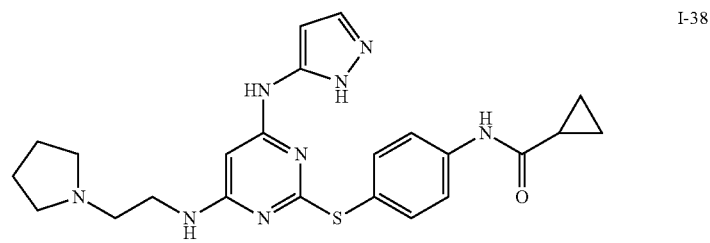
I-38
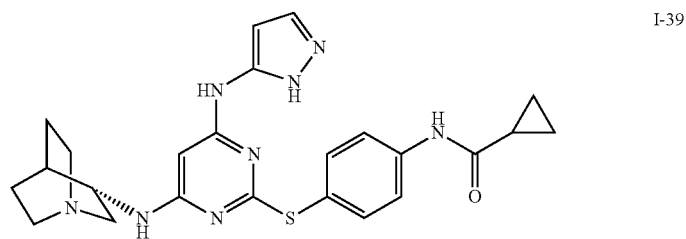
I-39
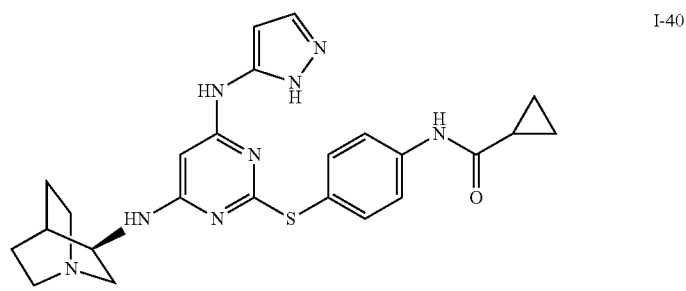
I-40
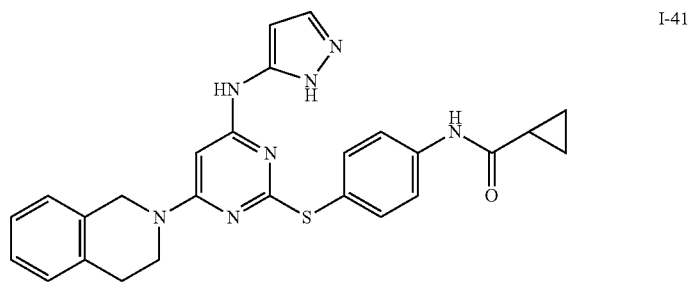
I-41

TABLE 2-continued
Exemplary Compounds of Formula I
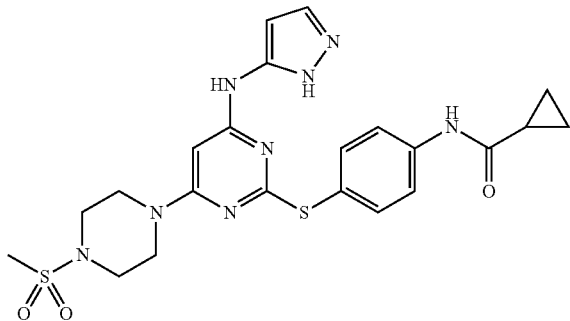 [SMILES: CS(=O)(=O)N1CCN(c2cc(Nc3ccn[nH]3)nc(Sc3ccc(NC(=O)C4CC4)cc3)n2)CC1]
I-42
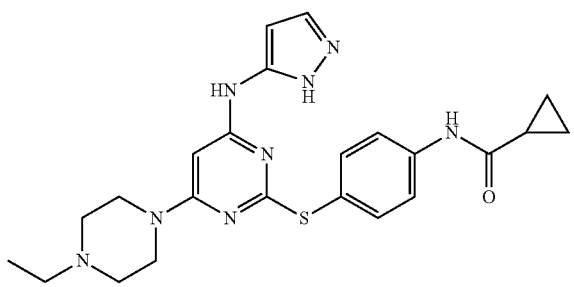 [SMILES: CCN1CCN(c2cc(Nc3ccn[nH]3)nc(Sc3ccc(NC(=O)C4CC4)cc3)n2)CC1]
I-43
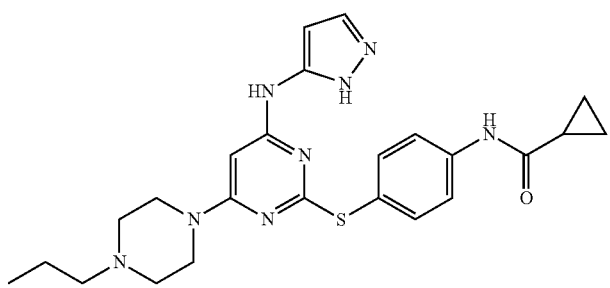 [SMILES: CCCN1CCN(c2cc(Nc3ccn[nH]3)nc(Sc3ccc(NC(=O)C4CC4)cc3)n2)CC1]
I-44
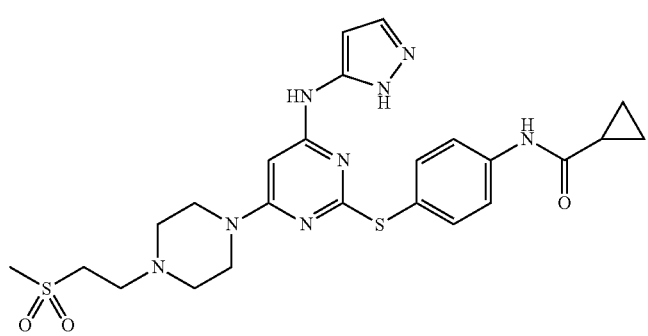 [SMILES: CS(=O)(=O)CCN1CCN(c2cc(Nc3ccn[nH]3)nc(Sc3ccc(NC(=O)C4CC4)cc3)n2)CC1]
I-45
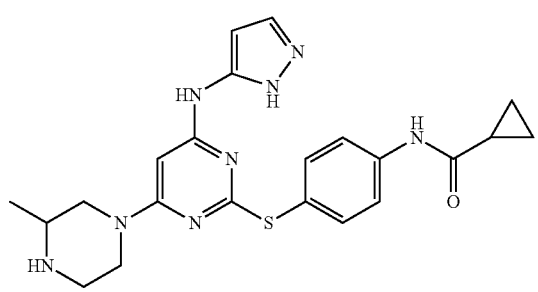 [SMILES: CC1CN(c2cc(Nc3ccn[nH]3)nc(Sc3ccc(NC(=O)C4CC4)cc3)n2)CCN1]
I-46

TABLE 2-continued
Exemplary Compounds of Formula I
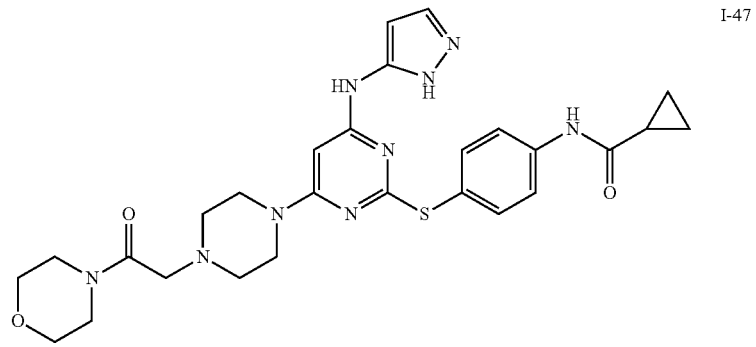
I-47
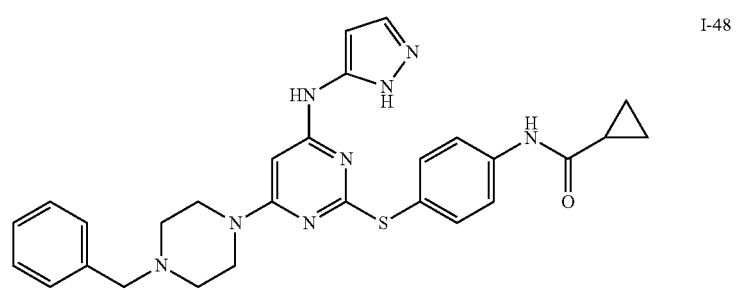
I-48
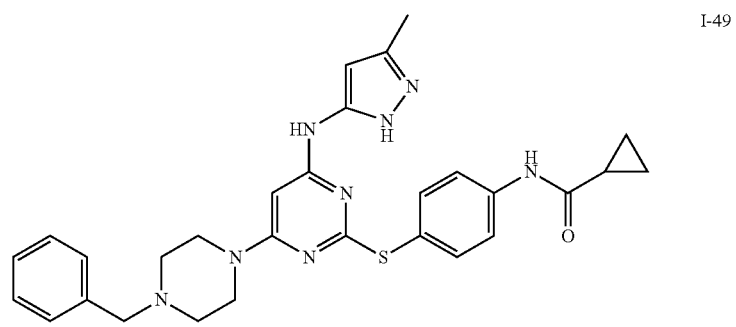
I-49
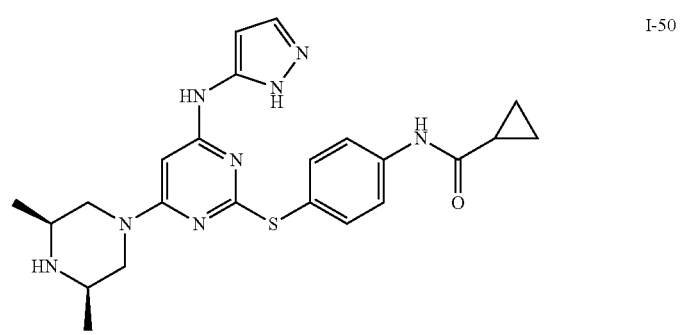
I-50

TABLE 2-continued
Exemplary Compounds of Formula I
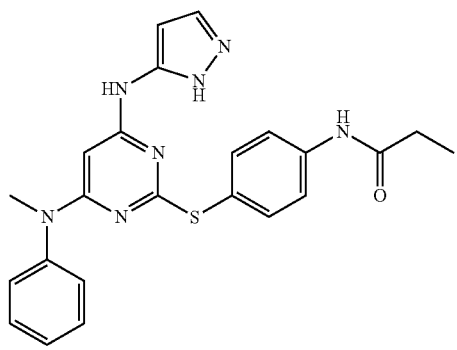 [SMILES: CCC(=O)Nc1ccc(Sc2nc(Nc3ccn[nH]3)cc(N(C)c3ccccc3)n2)cc1]
I-51
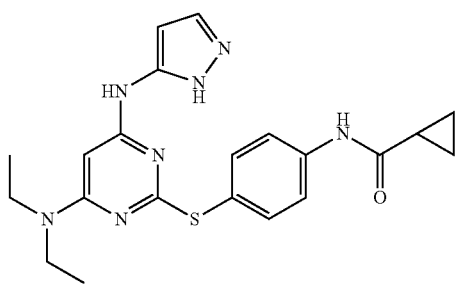 [SMILES: CCN(CC)c1cc(Nc2ccn[nH]2)nc(Sc2ccc(NC(=O)C3CC3)cc2)n1]
I-52
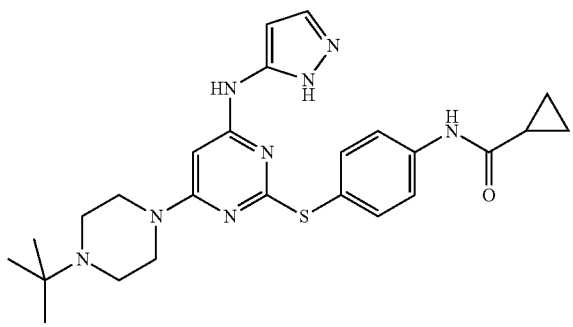 [SMILES: CC(C)(C)N1CCN(c2cc(Nc3ccn[nH]3)nc(Sc3ccc(NC(=O)C4CC4)cc3)n2)CC1]
I-53
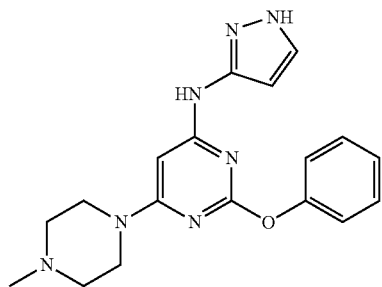 [SMILES: CN1CCN(c2cc(Nc3cc[nH]n3)nc(Oc3ccccc3)n2)CC1]
I-54
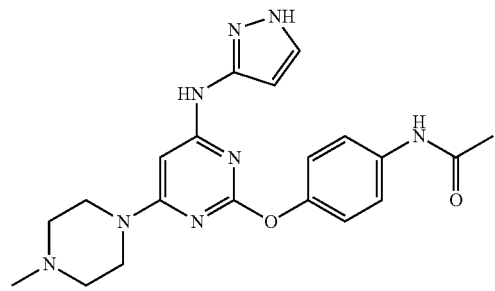 [SMILES: CC(=O)Nc1ccc(Oc2nc(Nc3cc[nH]n3)cc(N3CCN(C)CC3)n2)cc1]
I-55

TABLE 2-continued
Exemplary Compounds of Formula I
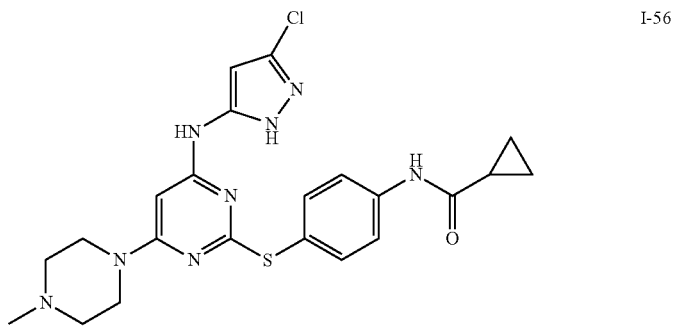
I-56
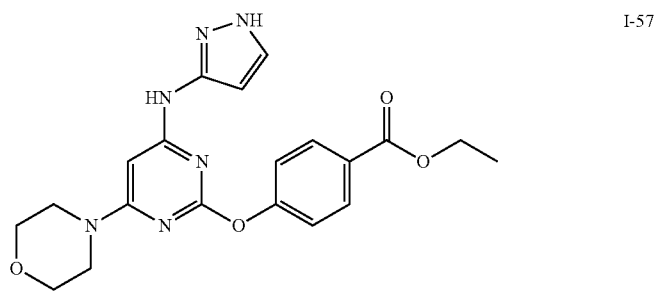
I-57
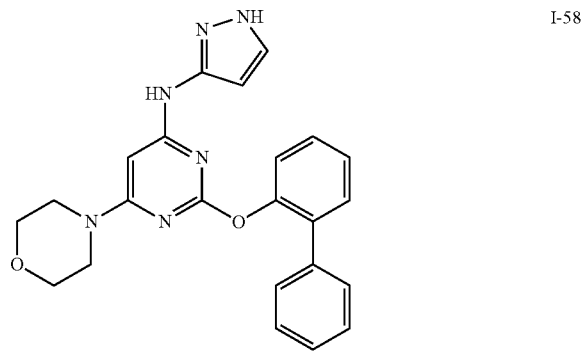
I-58
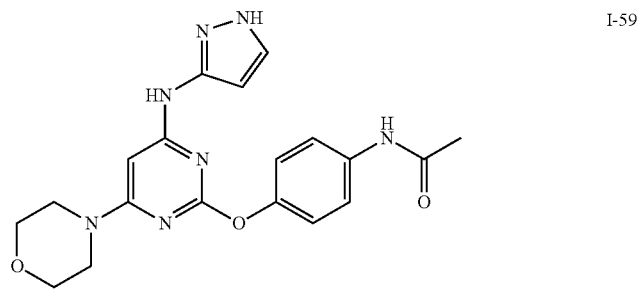
I-59
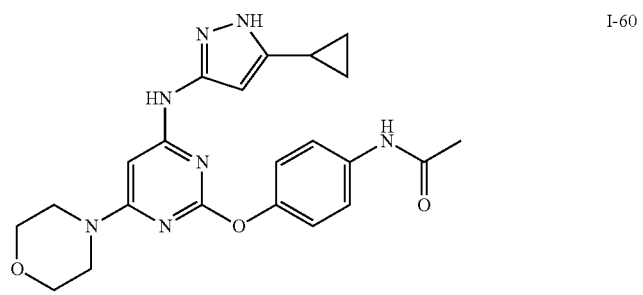
I-60

TABLE 2-continued

Exemplary Compounds of Formula I

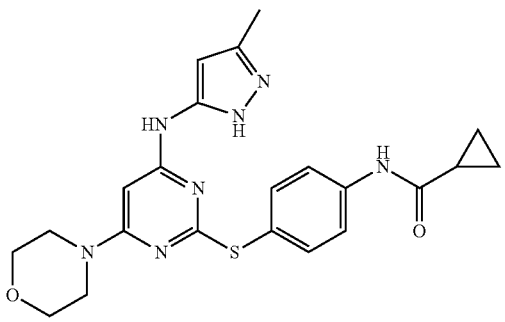 [SMILES: Cc1cc(Nc2cc(N3CCOCC3)nc(Sc3ccc(NC(=O)C4CC4)cc3)n2)[nH]n1]

I-61

Preferably the processes of the present invention are used to prepare a compound selected from Tables 1 and 2. More preferably the processes of the present invention are used to prepare a compound selected from Table 1.

According to an alternate embodiment, the present invention provides a compound of formula II, formula III, or formula IV:

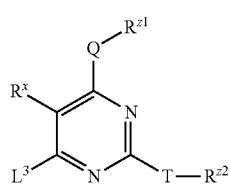

II

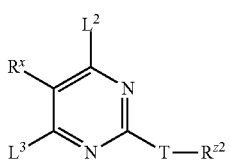

III

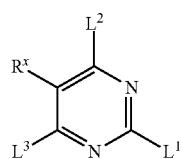

IV or a pharmaceutically acceptable salt thereof, wherein $R^x$, $R^y$, $L^1$, $L^2$, $L^3$, T, $R^{z2}$, and Q, and the preferred embodiments thereof, are as defined above.

According to a preferred embodiment, the present invention provides an intermediate of formula II.

According to another preferred embodiment, the present invention provides an intermediate of formula III.

According to yet another preferred embodiment, the present invention provides an intermediate of formula IV.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly Aurora and/or FLT-3 kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in protein kinase activity between a sample comprising said composition and protein kinase and an equivalent sample comprising protein kinase in the absence of said composition.

A "pharmaceutically acceptable derivative or salt" means any non-toxic salt, ester, salt of an ester or other derivative of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of Aurora and/or FLT-3 protein kinase.

According to another embodiment, the present invention provides processes for preparing a pharmaceutically acceptable salt of compound of formula I, I', or V comprising the step of converting a compound of formula I, I', or V prepared according to the processes of the present invention into the desired pharmaceutically acceptable salt. Such conversions are well known in the art. See, generally, "Advanced Organic Chemistry," Jerry March, 4$^{th}$ Ed., John Wiley and Sons, N.Y. (1992).

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

Table 3 below sets forth representative salts of compounds of Formula V of the present invention.

Representative Salts of Compounds of Formula V

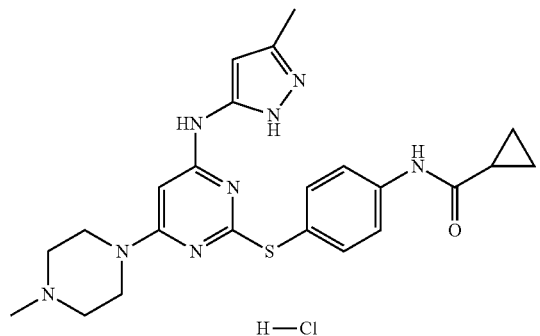 [SMILES: Cc1cc(Nc2cc(N3CCN(C)CC3)nc(Sc3ccc(NC(=O)C4CC4)cc3)n2)[nH]n1 ; Cl]

V-1i

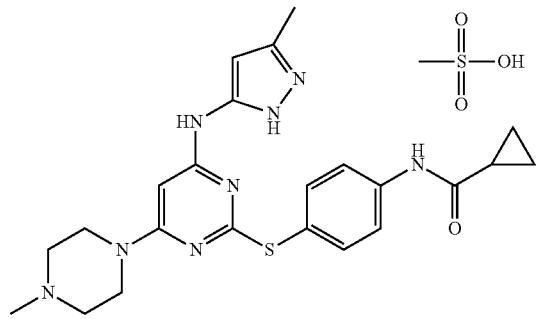

V-1ii

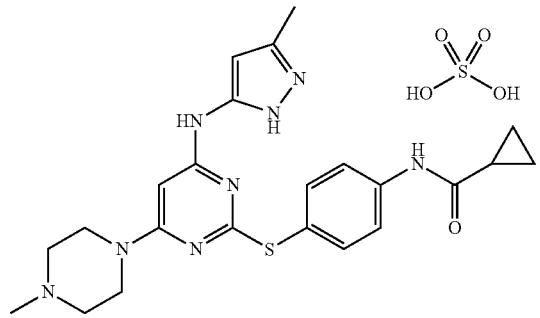

V-1iii

| Representative Salts of Compounds of Formula V |
|---|
| 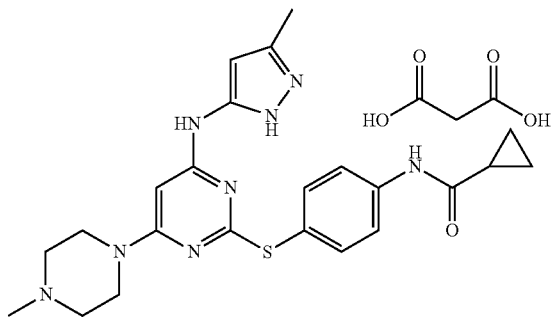 V-1iv |
| 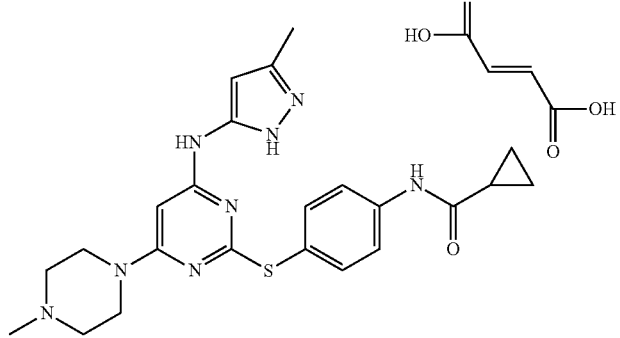 V-1v |
| 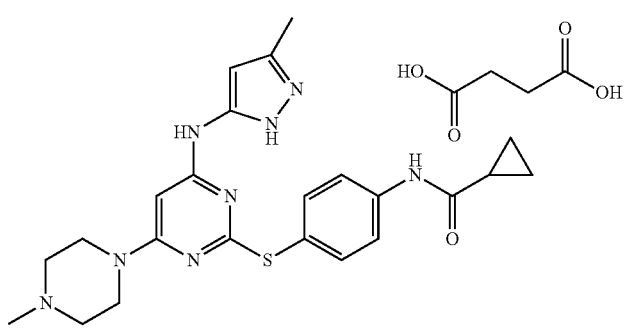 V-1vi |
| 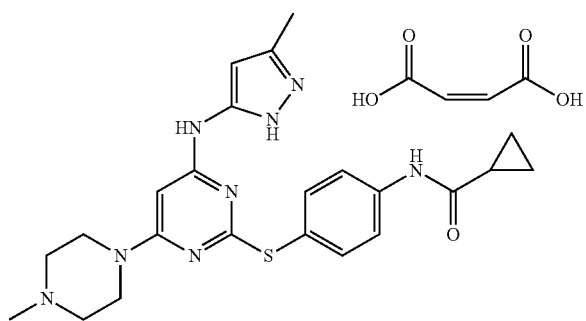 V-1vii |

Representative Salts of Compounds of Formula V
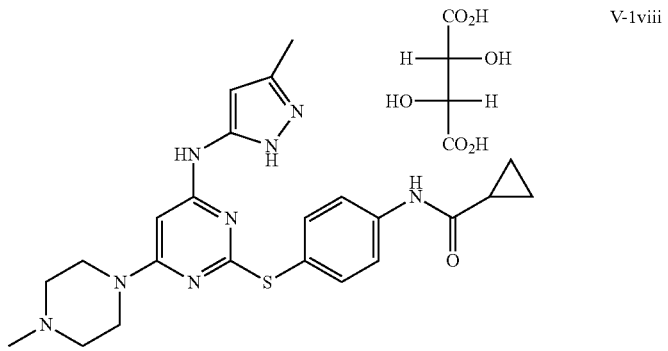
V-1viii
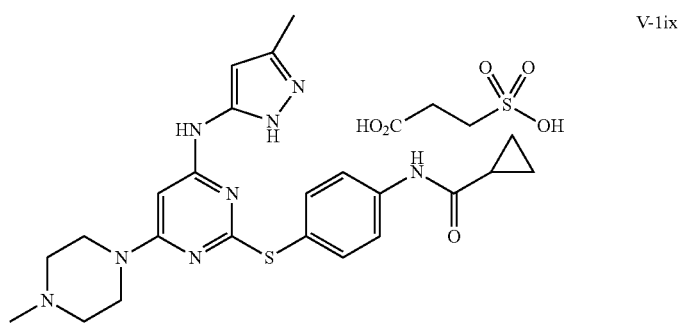
V-1ix
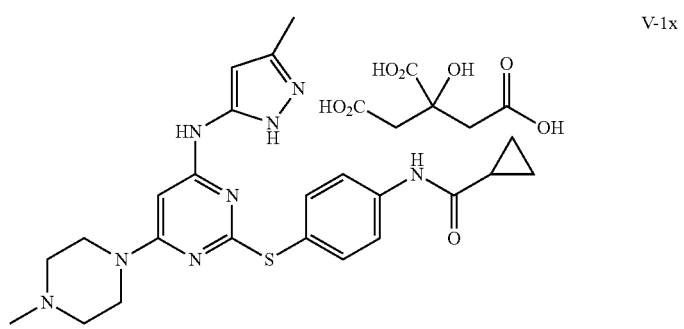
V-1x
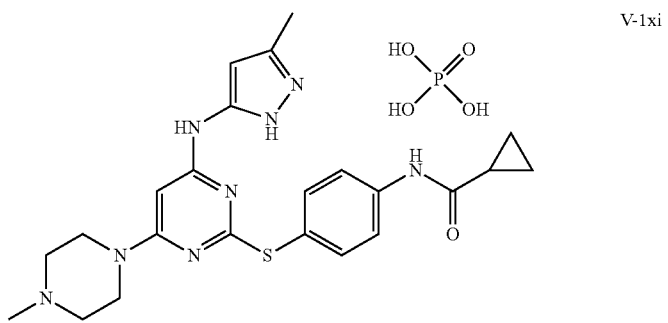
V-1xi Representative Salts of Compounds of Formula V

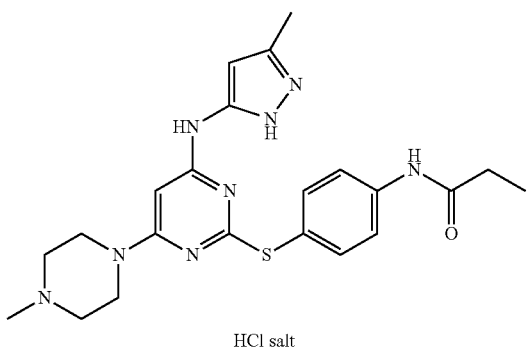 [SMILES: CCC(=O)Nc1ccc(Sc2nc(Nc3cc(C)n[nH]3)cc(N3CCN(C)CC3)n2)cc1]

V-20i

HCl salt

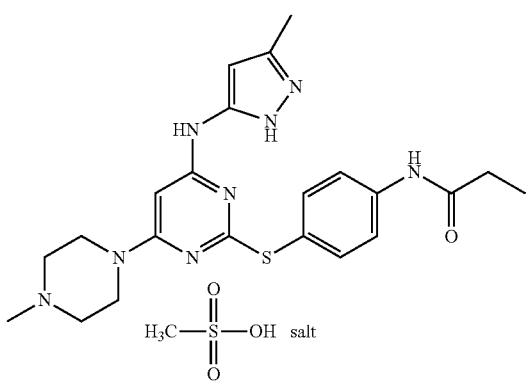

V-20ii salt

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetyl cholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Further examples of chemotherapeutic agents or other antiproliferative agents that may be combined with the compounds of the present invention to treat proliferative diseases and cancer include, but are not limited to, For example, other therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting Aurora-1, Aurora-2, Aurora-3, and/or FLT-3 kinase activity in a biological sample comprising the step of contacting said biological sample with a compound of formula V, or a composition comprising said compound.

The term "biological sample", as used herein, includes, without limitation, cell cultures or extracts thereof biopsied material obtained from a mammal or extracts thereof and blood, saliva, urine, feces, semen, tears, or other body fluids or extracts thereof.

Inhibition of Aurora-1, Aurora-2, Aurora-3, and/or FLT-3 kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention relates to a method of inhibiting Aurora-1 kinase activity in a patient comprising the step of administering to sail patient a compound of formula V, or a composition comprising said compound.

According to another embodiment, the invention relates to a method of inhibiting Aurora-2 kinase activity in a patient comprising the step of administering to said patient a compound of formula V, or a composition comprising said compound.

According to another embodiment, the invention relates to a method of inhibiting Aurora-3 kinase activity in a patient comprising the step of administering to said patient a compound of formula V, or a composition comprising said compound.

According to another embodiment, the invention relates to a method of inhibiting FLT-3 kinase activity in a patient comprising the step of administering to said patient a compound of formula V, or a composition comprising said compound.

According to another embodiment, the invention relates to a method of inhibiting Aurora-1, Aurora-2, Aurora-3, and FLT-3 kinase activity in a patient comprising the step of administering to said patient a compound of formula V, or a composition comprising said compound.

According to another embodiment, the invention provides a method for treating or lessening the severity of an Aurora-mediated disease or condition in a patient comprising the step of administering to said patient a compound of formula V, or composition comprising said compound.

The term "Aurora-mediated disease", as used herein, means any disease or other deleterious condition or disease in which an Aurora family protein kinase is known to play a role. Such diseases or conditions include, without limitation, melanoma, leukemia, or a cancer selected from colon, breast, gastric, ovarian, cervical, melanoma, renal, prostate, lymphoma, neuroblastoma, pancreatic, leukemia and bladder.

According to another embodiment, the present invention relates to a method of treating cancer in a patient, comprising the step of administering to said patient a compound of formula V or composition thereof.

According to another embodiment, the present invention relates to a method of treating melanoma, lymphoma, neuroblastoma, leukemia, or a cancer selected from colon, breast, lung, kidney, ovary, pancreatic, renal, CNS, cervical, prostate, or cancer of the gastric tract in a patient, comprising the step of administering to said patient a compound of formula V or composition thereof.

According to another embodiment, the present invention relates to a method of treating acute-myelogenous leukemia (AML), acute lymphocytic leukemia (ALL), mastocytosis or gastrointestinal stromal tumor (GIST) in a patient, comprising the step of administering to said patient a compound of formula V or composition thereof.

Another aspect of the present invention relates to the disruption of mitosis of cancer cells in a patient, comprising the step of administering to said patient a compound of formula V or composition thereof.

According to another embodiment, the present invention relates to a method of treating or lessening the severity of a cancer in a patient comprising the step of disrupting mitosis of the cancer cells by inhibiting Aurora-1, Aurora-2, and/or Aurora-3 with a compound of formula V or composition thereof.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

In order that the invention described herein may be more fully understood, the following examples are set forth. It should be understood that these examples are for illustrative purposes only and are not to be construed as limiting this invention in any manner.

EXAMPLES

General Scheme:

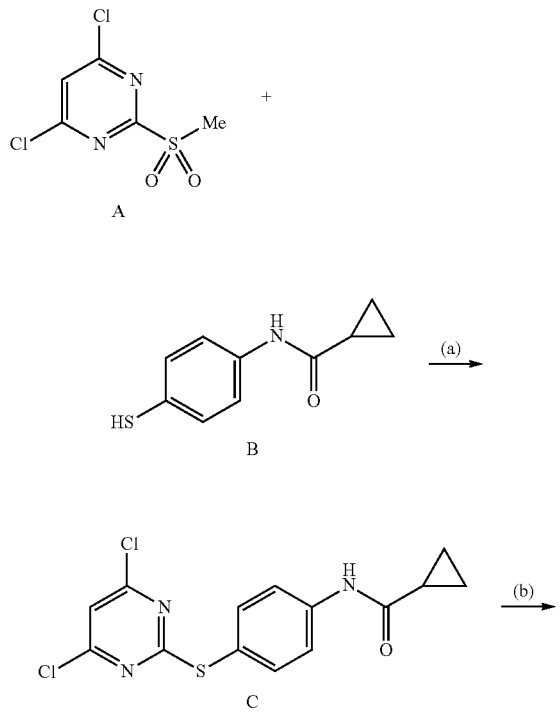

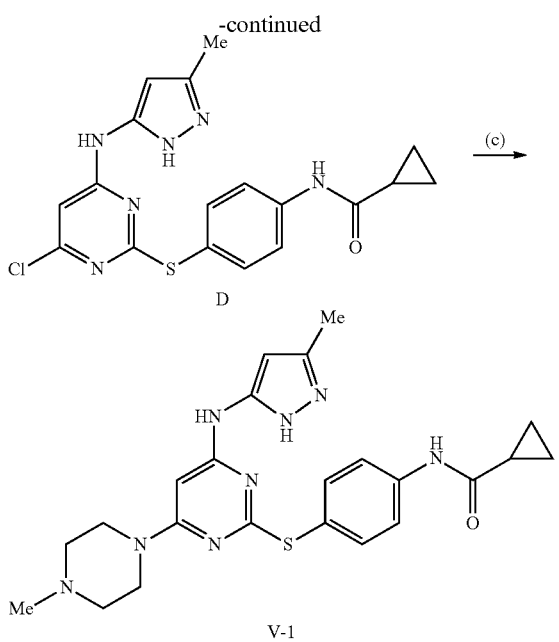

Example 1

4,6-Dichloropyrimidine-2-methylsulfone (A): Prepared by methods substantially similar to those set forth in Koppell et al, *JOC*, 26, 1961, 792, in the following manner. To a stirred solution of 4,6-dichloro-2-(methylthio)pyrimidine (50 g, 0.26 mol) in dichloromethane (1 L) at 0° C. was added meta-chloroperoxybenzoic acid (143.6 g, 0.64 mol) over a period of 20 minutes. The solution was allowed to warm to room temperature and was stirred for 4 hours. The mixture was diluted with dichloromethane (1.5 L) and then treated sequentially with 50% Na$_2$S$_2$O$_3$/NaHCO$_3$ solution (2×200 ml), sat. NaHCO$_3$ solution (4×300 ml), and brine (200 ml) then dried (MgSO$_4$). The solvent was removed in vacuo to afford an off-white solid which was redissolved in EtOAc (1 L) and treated sequentially with sat. NaHCO$_3$ solution (3×300 ml), and brine (100 ml) then dried (MgSO$_4$). The solvent was removed in vacuo to afford the title compound (A) as a white solid (55.6 g, 96% yield). $^1$H NMR CDCl$_3$ δ 3.40 (3H, s, CH3), 7.75 (1H, s. ArH).

Example 2

Cyclopropane carboxylic acid [4-(4,6-dichloro-pyrimidin-2-ylsulphanyl)-phenyl]-amide (C): A suspension of compound A (10 g, 44.04 mmol) and cyclopropane carboxylic acid (4-mercapto-phenyl)-amide (B, 8.51 g, 44.04 mmol) in t-butanol (300 ml) was degassed by evacuation, then flushing with nitrogen. The mixture was stirred at 90° C. under nitrogen atmosphere for 1 hour then the solvent was removed in vacuo. The residue was dissolved in ethyl acetate (600 ml) and washed with an aqueous solution of potassium carbonate and sodium chloride. The organic extract was dried over magnesium sulphate, concentrated to a low volume and allowed to crystallize. The product C was collected as colourless crystals, (11.15 g, 74%). $^1$H-NMR DMSO-d$^6$, δ 0.82-0.89 (4H, m), 1.80-1.88 (1H, m), 7.55 (2H, d), 7.70-7.76 (3H, m), 10.49 (1H, s); M+H, 340.

Example 3

Cyclopropane carboxylic acid{4-[4-chloro-6-(5-methyl-2H-pyrazol-3-ylamino)-pyrimidin-2-ylsulphanyl]-phenyl}amide (D): A mixture of compound C (1.0 g, 2.94 mmol) and 3-amino-5-methylpyrazole (314 mg, 3.23 mmol) in dimethylformamide (6 ml) was treated with diisopropylethylamine (0.614 ml, 3.53 mmol) and sodium iodide (530 mg, 3.53 mmol). The mixture was stirred under nitrogen at 85° for 4 hours, cooled to room temperature and diluted with ethyl acetate. The solution was washed with water (x 4), dried over magnesium sulphate and concentrated to 5 ml to afford, upon crystallization and harvesting of colourless crystals, the title compound D (920 mg, 78%).

$^1$H-NMR DMSO-d$^6$, δ 0.80-0.87 (4H, m), 1.77-1.85 (1H, m), 1.92 (1H, s), 5.24 (1H, br s), 6.47 (1H, br s), 7.55 (2H, d), 7.70-7.80 (2H, m), 10.24 (1H, s), 10.47 (1H, s), 11.92 (1H, s).

Example 4

Cyclopropane carboxylic acid {4-[4-(4-methyl-piperazin-1-yl)-6-(5-methyl-2H-pyrazol-3-ylamino)-pyrimidin-2-yl-sulphanyl]-phenyl}-amide (V-1): Compound D (2.373 g, 5.92 mmol) was treated with N-methylpiperazine (10 ml) and the mixture stirred at 110° for 2 hours. The excess N-methylpiperazine was removed in vacuo then the residue was dissolved in ethyl acetate, washed with aqueous sodium bicarbonate solution, dried over magnesium sulphate, and concentrated. The residue was crystallised from methanol to give colourless crystals of desired product V-1 (1.82 g, 66%), $^1$H-NMR DMSO-d$^6$, δ 0.81 (4H, d), 1.79 (1H, m), 2.01 (3H, s), 2.18 (3H, s), 2.30 (4H, m), 3.35 (masked signal), 5.42 (1H, s), 6.02 (1H, br s), 7.47 (2H, d), 7.69 (2H, d), 9.22 (1H, s), 10.39 (1H, s), 11.69 (1H, s).

Example 5

N-{4-[4-(5-Methyl-2H-pyrazol-3-ylmethyl)-6-(4-propyl-piperazin-1-yl)-pyrimidin-2-ylsulfanyl]-phenyl}-propionamide (V-5): Ethane carboxylic acid {4-[4-chloro-6-(5-methyl-2H-pyrazol-3-ylamino)-pyrimidin-2-ylsulphanyl]-phenyl}amide (119 mg, 0.306 mmol, prepared by methods analogous to those set forth in Examples 1, 2, and 3) in n-BuOH (5 mL) was treated with N-propylpiperazine dihydrobromide (887 mg, 3.06 mmol) followed by diisopropylethylamine (1.066 mL, 6.12 mmol). The resulting mixture was stirred at 110° for 20 hours. The solvent was removed under reduced pressure, and the residue was purified using preparative HPLC to afford the title compound. $^1$H NMR (DMSO): δ 1.10 (3H, t), 2.05 (3H, s), 2.35 (2H, d), 3.30 (4H, s), 3.70 (4H, s), 5.45 (1H, s), 6.05 (1H, br s), 7.45 (2H, d), 7.70 (2H, d), 9.20 (1H, s), 10.05 (1H, s), 11.70 (1H, br s).

Example 6

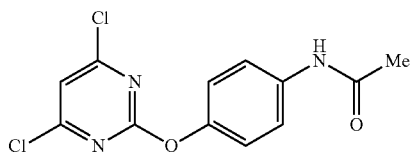 [SMILES: CC(=O)Nc1ccc(Oc2nc(Cl)cc(Cl)n2)cc1]

N-[4-(4,6-Dichloro-pyrimidin-2-yloxy)-phenyl]-acetamide: A solution of 4-acetamidophenol (666 mg, 4.40 mmol) in anhydrous THF (40 ml), stirring at ambient temperature, was treated with a 60% dispersion of sodium hydride in mineral oil (176 mg, 4.40 mmol). The reaction mixture was then allowed to stir for 30 minutes at ambient temperature before 4,6-dichloro-2-methanesulfonyl-pyrimidine (1.0 g, 4.40 mmol) was added. The reaction was then allowed to stir for a further 3 hours before the reaction was diluted with saturated aqueous NH$_4$Cl and EtOAc. The organic layer was separated, washed with saturated aqueous NaCl and dried over sodium sulfate then concentrated in vacuo. The residue was purified by column chromatography (Silica Gel, MeOH:CH$_2$Cl$_2$, 5:95) yield the title compound 1.25 g, (95%) as a solid. $^1$H-NMR (400 MHz, DMSO-d$_6$): δ 2.06 (3H, s), 7.18 (2H, d, J=8.5 Hz), 7.62 (2H, d, J=8.5 Hz), 10.05 (1H, s), LC-MS: ES+=298.16, ES−=296.18).

Example 7

Cyclopropanecarboxylic acid {4-[4-(4-methyl-4-oxy-piperazin-1-yl)-6-(5-methyl-2H-pyrazol-3-ylamino)-pyrimidin-2-ylsulfanyl]-phenyl}-amide (V-19): Compound V-1 (1 g, 2.1 mmol) was suspended in dichloromethane (20 mL), cooled to 0° C. and treated with a dichloromethane solution of mCPBA in 10 aliquots at 10 minute intervals (each aliquot consisting of 100 mg, 0.44 mmol in 1 ml DCM). Each time an aliquot was added the solution turned brown and gradually returned to a yellow colour as the mCPBA was consumed. Once all the starting material had been consumed, the solvent was removed in vacuo and the resulting orange oil was purified by preparative HPLC to give the title compound as an off-white solid (69 mg, 7%); $^1$H NMR (DMSO-d$_6$): 0.85-0.91 (4H, m), 1.90 (1H, m), 2.10 (3H, s), 3.10-3.17 (2H, m), 3.25 (3H, s), 3.50-3.66 (4H, m), 3.98 (2H, d), 5.50 (1H, s), 6.11 (1H, br s), 7.56 (2H, d), 7.80 (2H, d), 9.42 (1H, s), 10.50 (1H, s), 11.82 (1H, br s).

Example 8

Cyclopropane carboxylic acid {4-[4-(4-methyl-piperazin-1-yl)-6-(5-methyl-2H-pyrazol-3-ylamino)-pyrimidin-2-yl-sulphanyl]-phenyl}-amide methanesulfonate (V-iii): Compound V-1 (515 mg, 1.11 mmol) was suspended in ethanol (80 mL) and heated to reflux. To the clear solution was added methanesulfonic acid (106 mg, 1.11 mmol) and the reaction mixture was refluxed for a further 10 minutes. The mixture was allowed to cool to room temperature and the solvent was evaporated until a precipitate began to form. The mixture was then cooled to 0° C. and the resulting precipitate collected by filtration before being dried under vacuum to afford the title compound as a white solid (290 mg, 47%); $^1$H NMR (400 MHz, DMSO-d$_6$) 0.81-0.82 (4H, d), 1.82 (1H, m), 2.36 (6H, s), 2.83 (3H, d), 3.03-3.12 (4H, m), 3.40-3.47 (2H, m), 3.79 (br s, OH), 4.14-4.18 (2H, m), 5.50 (1H, s), 6.05 (1H, s), 7.49 (2H, d), 7.72 (2H, d), 9.61 (1H, s), 10.41 (1H, br s), 10.80 (1H, s)

Example 9

The following compounds set forth in Table 4 below were prepared according to the processes of the present invention and by methods substantially similar to those set forth in Examples 1-8 above. The characterization data for these compounds is summarized in Table 4 below and includes $^1$H NMR, melting point (m.p.), and mass spectral (MS) data.

Unless otherwise indicated each annotated $^1$H NMR, set forth in Table 4, was obtained at 400 MHz in deuterated dimethylsulfoxide (dmso-d$_6$).

TABLE 4

Characterization Data for Representative Compounds

| No. | Structure | m.p. | $^1$H-NMR | Mass Spec |
|---|---|---|---|---|
| V-2 | 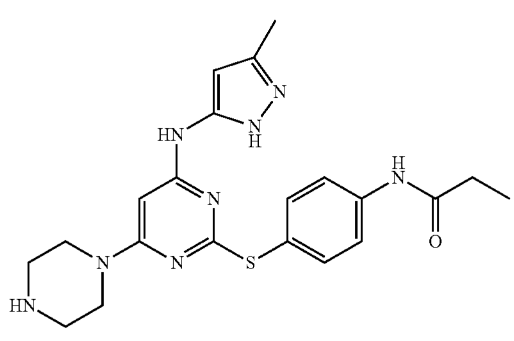 [SMILES: CCC(=O)Nc1ccc(Sc2nc(Nc3cc(C)n[nH]3)cc(N3CCNCC3)n2)cc1] | — | 1.09 (3H, t), 2.00 (3H, s), 2.34 (2H, q), 2.72 (4H, m), 3.3 (masked signal), 5.42 (1H, s), 5.98 (1H, s), 7.47 (2H, d), 7.69 (2H, d), 9.20 (1H, s), 10.07 (1H, s),. 11.69 (1H, s) | ES+ 439.4 ES− 437.4 |

TABLE 4-continued

Characterization Data for Representative Compounds

| No. | Structure | m.p. | ¹H-NMR | Mass Spec |
|---|---|---|---|---|
| V-3 | 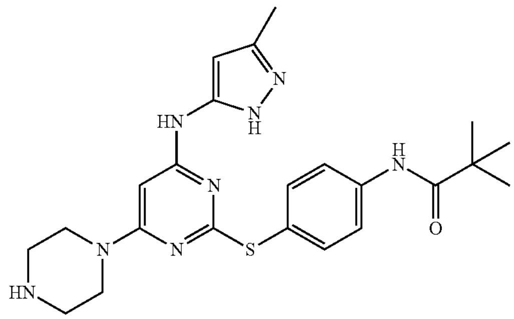 [SMILES: Cc1cc(Nc2cc(N3CCNCC3)nc(Sc3ccc(NC(=O)C(C)(C)C)cc3)n2)[nH]n1] | 178-181° C. | 1.24 (9H, s), 1.98 (3H, s), 2.68-2.70 (4H, m), 3.31 (4H, masked signal), 5.35 (1H, s), 5.96 (1H, br s), 7.47 (2H, d), 7.79 (2H, d), 9.20 (1H, s), 9.33 (1H, s), 11.66 (1H, s) | ES+ 467.35 ES− 465.38 |
| V-4 | 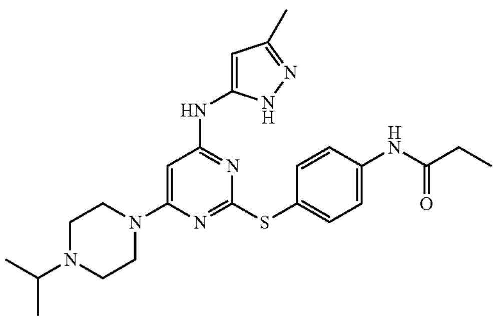 [SMILES: CCC(=O)Nc1ccc(Sc2nc(Nc3cc(C)n[nH]3)cc(N3CCN(C(C)C)CC3)n2)cc1] | — | 0.97 (6H, d), 1.10 (3H, t), 2.00 (3H, s), 2.35 (2H, q), 2.45 (4H, br s), 2.65 (1H, br s), 3.35 (4H, br s), 5.40 (1H, s), 6.00 (1H, br s), 7.50 (2H, d), 7.70 (2H, d), 9.20 (1H, s), 10.10 (1H, s), 11.70 (1H, br s) | ES+ 481.4 |
| V-6 | 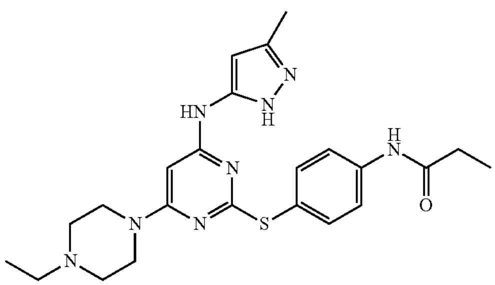 [SMILES: CCC(=O)Nc1ccc(Sc2nc(Nc3cc(C)n[nH]3)cc(N3CCN(CC)CC3)n2)cc1] | — | 1.01 (3H, t), 1.09 (3H, t), 2.00 (3H, s), 2.31-2.37 (8H, m), 3.35 (masked signal), 5.42 (1H, s), 6.01 (1H, br s), 7.47 (2H, d), 7.70 (2H, d), 9.22 (1H, s), 10.07 (1H, s), 11.69 (1H, s) | ES+ 467.3 ES− 465.4 |
| V-7 | 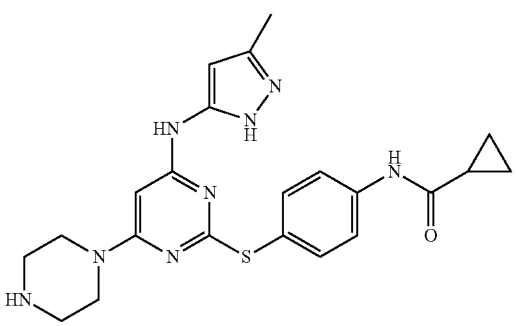 [SMILES: Cc1cc(Nc2cc(N3CCNCC3)nc(Sc3ccc(NC(=O)C4CC4)cc3)n2)[nH]n1] | — | 0.80-0.82 (4H, m), 1.81 (1H, m), 2.01 (3H, s), 2.68 (4H, m), 3.1-3.5 (5H, m), 5.43 (1H, s), 5.99 (1H, br s), 7.47 (2H, d), 7.69 (2H, d), 9.21 (1H, s), 10.40 (1H, s), 11.70 (1H, s) | ES+ 451.3 ES− 449.4 |
| V-8 | 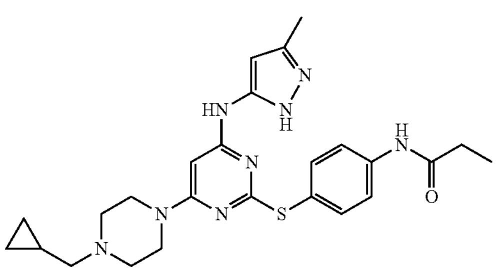 [SMILES: CCC(=O)Nc1ccc(Sc2nc(Nc3cc(C)n[nH]3)cc(N3CCN(CC4CC4)CC3)n2)cc1] | — | 0.08 (2H, m), 0.46 (2H, m), 0.84 (1H, m), 1.09 (3H, t), 2.00 (3H, s), 2.19 (2H, d), 2.34 (2H, q), 2.44 (4H, m), 3.35 (masked signal), 5.41 (1H, s), 6.00 (1H, br s), 7.47 (2H, d), 7.70 (2H, d), 9.23 (1H, s), 10.08 (1H, s), 11.66 (1H, s) | ES+ 493.4 ES− 491.4 |

TABLE 4-continued

Characterization Data for Representative Compounds

| No. | Structure | m.p. | ¹H-NMR | Mass Spec |
|---|---|---|---|---|
| V-9 | 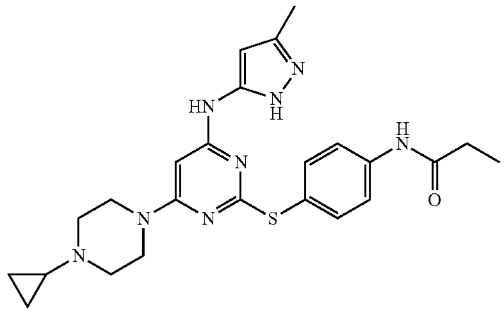 [SMILES: CCC(=O)Nc1ccc(Sc2nc(Nc3cc(C)n[nH]3)cc(N3CCN(C4CC4)CC3)n2)cc1] | — | 0.33 (2H, m), 0.42 (2H, m), 1.09 (3H, t), 1.62 (1H, m), 2.00 (3H, s), 2.34 (2H, q), 2.53 (4H, m), 3.32 (masked signal), 5.42 (1H, s), 6.00 (1H, br s), 7.47 (2H, d), 7.70 (2H, d), 9.22 (1H, s), 10.07 (1H, s), 11.69 (1H, s) | ES+ 479.4 ES− 477.4 |
| V-10 | 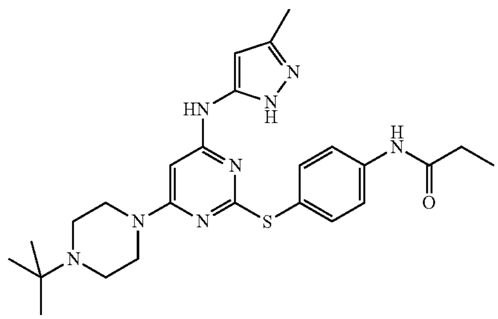 [SMILES: CCC(=O)Nc1ccc(Sc2nc(Nc3cc(C)n[nH]3)cc(N3CCN(C(C)(C)C)CC3)n2)cc1] | 161-163 | 1.01 (9H, s), 1.09 (3H, t), 2.00 (3H, s), 2.34 (2H, q), 2.5 (masked signal), 3.36 (masked signal), 5.42 (1H, s), 5.98 (1H, br s), 7.47 (2H, d), 7.70 (2H, d), 9.21 (1H, s), 10.08 (1H, s), 11.69 (1H, s) | ES+ 495.4 ES− 493.4 |
| V-11 | 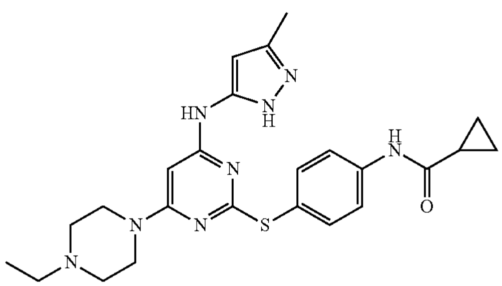 [SMILES: CCN1CCN(c2cc(Nc3cc(C)n[nH]3)nc(Sc3ccc(NC(=O)C4CC4)cc3)n2)CC1] | — | 0.80-0.82 (4H, m), 1.01 (3H, t), 1.81 (1H, m), 2.01 (3H, s), 2.32-2.37 (6H, m), 3.35 (masked signal), 5.43 (1H, s), 6.01 (1H, br s), 7.47 (2H, d), 7.69 (2H, d), 9.23 (1H, s), 10.40 (1H, s), 11.69 (1H, s) | ES+ 479.3 ES− 477.4 |
| V-12 | 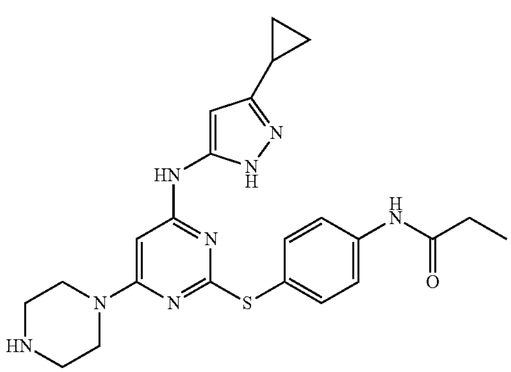 [SMILES: CCC(=O)Nc1ccc(Sc2nc(Nc3cc(C4CC4)n[nH]3)cc(N3CCNCC3)n2)cc1] | — | 0.48-0.59 (2H, m), 1.75-1.87 (2H, m), 1.08 (3H, t, J = 7.5 Hz), 1.61-1.75 (1H, m), 2.32 (2H, q, J = 7.5 Hz), 2.61-2.71 (4H, m), 3.20-3.30 (4H, m), 5.47 (1H, s), 6.10 (1H, brs), 7.47 (2H, d, J = 8.4 Hz), 7.70 (2H, d, J = 8.4 Hz), 9.20 (1H, brs), 10.13 (1H, s), 11.74 (1H, brs) | ES+ 465.34 ES− 463.37 |

TABLE 4-continued

Characterization Data for Representative Compounds

| No. | Structure | m.p. | ¹H-NMR | Mass Spec |
|---|---|---|---|---|
| V-13 | 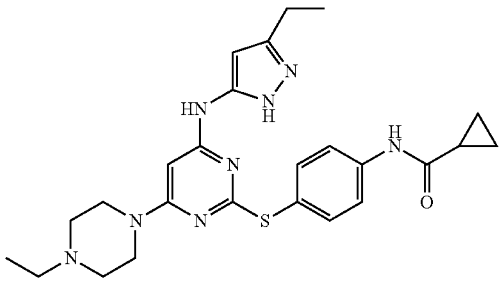 [SMILES: CCc1cc(Nc2cc(N3CCN(CC)CC3)nc(Sc3ccc(NC(=O)C4CC4)cc3)n2)[nH]n1] | — | 0.81-0.82 (4H, m), 1.01 (3H, t), 1.05 (3H, t), 1.81 (1H, m), 2.26-2.38 (8H, m), 3.35 (masked signal), 5.44 (1H, s), 6.03 (1H, br s), 7.47 (2H, d), 7.70 (2H, d), 9.25 (1H, s), 10.39 (1H, s), 11.74 (1H, s) | ES+ 493.4 ES− 491.4 |
| V-14 | 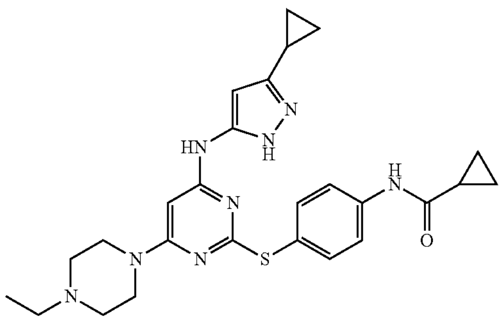 [SMILES: CCN1CCN(c2cc(Nc3cc(C4CC4)n[nH]3)nc(Sc3ccc(NC(=O)C4CC4)cc3)n2)CC1] | — | 0.54 (2H, m), 0.79-0.82 (6H, m), 1.01 (3H, t), 1.69 (1H, m), 1.82 (1H, m), 2.32-2.36 (6H, m), 3.35 (masked signal), 5.45 (1H, s), 6.07 (1H, br s), 7.47 (2H, d), 7.70 (2H, d), 9.23 (1H, s), 10.38 (1H, s), 11.70 (1H, s) | ES+ 505.4 ES− 503.4 |
| V-15 | 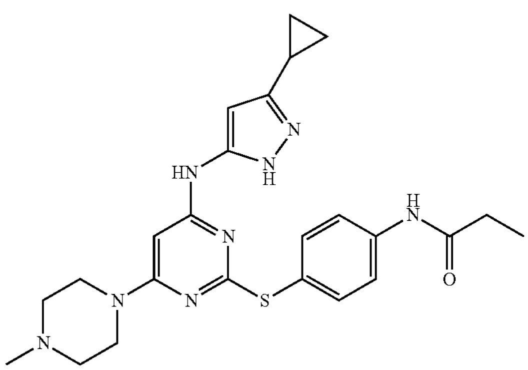 | — | 0.49-0.59 (2H, m), 0.76-0.85 (2H, m), 1.08 (3H, t, J = 7.5 Hz), 1.63-1.72 (1H, m), 2.19 (3H, s), 2.23-2.38 (6H, m), 3.30-3.43 (4H, m), 5.50 (1H, s), 6.15 (1H, brs), 7.48 (2H, d, J = 8.6 Hz), 7.70 (2H, d, J = 8.6 Hz), 9.23 (1H, brs), 10.04 (1H, s), 11.71 (1H, brs). | ES+ 479.34 ES− 477.37 |
| V-16 | 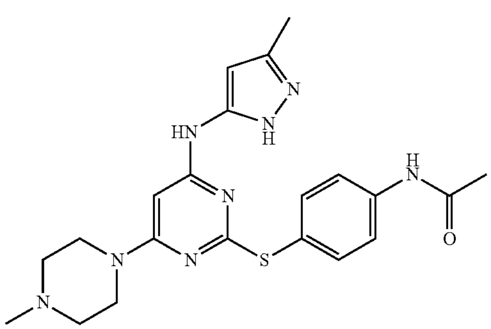 [SMILES: CC(=O)Nc1ccc(Sc2nc(Nc3cc(C)n[nH]3)cc(N3CCN(C)CC3)n2)cc1] | — | 2.02 (3H, s), 2.07 (3H, s), 2.18 (3H, s), 2.30 (4H, m), 3.35 (masked signal), 5.44 (1H, s), 6.03 (1H, br s), 7.47 (2H, d), 7.67 (2H, d), 9.23 (1H, s), 10.14 (1H, s), 11.71 (1H, s) | ES+ 439.3 ES− 437.4 |

TABLE 4-continued

Characterization Data for Representative Compounds

| No. | Structure | m.p. | ¹H-NMR | Mass Spec |
|---|---|---|---|---|
| V-17 | 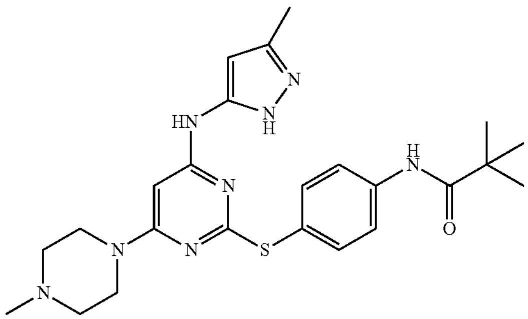 [SMILES: Cc1cc(Nc2cc(N3CCN(C)CC3)nc(Sc3ccc(NC(=O)C(C)(C)C)cc3)n2)[nH]n1] | | 1.23 (9H, s), 1.97 (3H, s), 2.20 (3H, s), 2.30-2.33 (4H, m), 3.31 (4H, masked signal), 5.37 (1H, s), 5.96 (1H, br s), 7.47 (2H, d), 7.79 (2H, d), 9.24 (1H, s), 9.38 (1H, s), 11.67 (1H, br s) | ES+ 481.4 ES− 479.4 |
| V-18 | 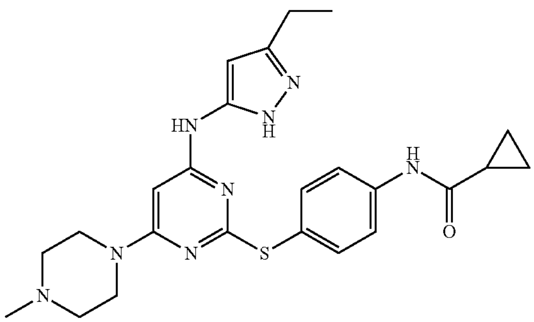 [SMILES: CCc1cc(Nc2cc(N3CCN(C)CC3)nc(Sc3ccc(NC(=O)C4CC4)cc3)n2)[nH]n1] | | 0.76-0.91 (4H, m), 1.00-1.18 (3H, m), 1.76-1.86 (1H, m), 2.18 (3H, s), 2.22-2.43 (6H, m), 3.3-3.4 (4H obscured), 5.46 (1H, s), 6.08 (1H br s), 7.49 (2H, d), 7.72 (2H, d), 9.30 (1H, s), 10.40 (1H, s), 11.72 (1H, s) | ES+ 479.3 ES− 477.3 |
| V-20 | 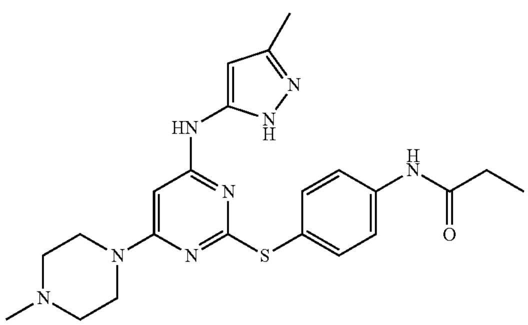 [SMILES: CCC(=O)Nc1ccc(Sc2nc(Nc3cc(C)n[nH]3)cc(N3CCN(C)CC3)n2)cc1] | 137.5-138.9 | 1.10 (3H, t), 2.00 (2H, s), 2.18 (3H, s), 2.28-2.36 (5H, m), 2.98 (2H, br s), 3.32 (4H, m), 5.40 (1H, s), 6.05 (1H, br s), 7.45 (2H, d), 7.70 (2H, d), 9.20 (1H, s), 10.10 (1H, s), 11.70 (1H, s) | MS 453.5 (M + H)+ |
| I-1 | 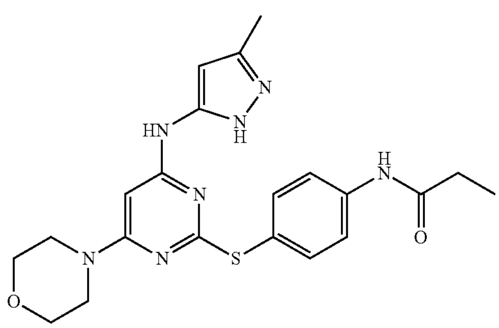 [SMILES: CCC(=O)Nc1ccc(Sc2nc(Nc3cc(C)n[nH]3)cc(N3CCOCC3)n2)cc1] | 238-239 | 1.10 (3H, t), 2.00 (3H, s), 2.45 (2H, q), 3.65 (4H, s), 5.45 (1H, s), 6.05 (1H, br s), 7.50 (2H, d), 7.80 (2H, d), 9.25 (1H, s), 10.05 (1H, s), 11.70 (1H, brs) | MS 440.3 (M + H)+ |
| I-2 | 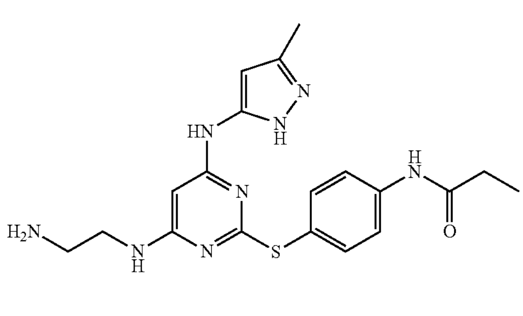 [SMILES: CCC(=O)Nc1ccc(Sc2nc(NCCN)cc(Nc3cc(C)n[nH]3)n2)cc1] | — | 1.09 (3H, t), 2.00 (3H, s), 2.34 (2H, q), 2.59 (2H, m), 3.04 (2H, m), 3.3 (masked signal), 5.39 (1H, s), 5.77 (1H, br s), 6.85 (1H, s), 7.47 (2H, d), 7.69 (2H, d), 9.07 (1H, s), 10.07 (1H, s), 11.63 (1H, br s) | ES+ 413.3 ES− 411.4 |

TABLE 4-continued

Characterization Data for Representative Compounds

| No. | Structure | m.p. | ¹H-NMR | Mass Spec |
|---|---|---|---|---|
| I-3 | 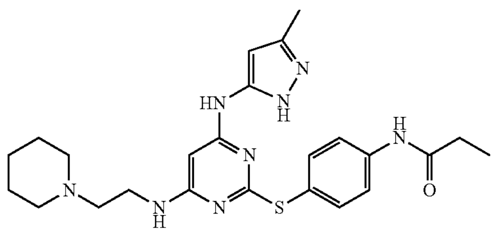 [SMILES: CCC(=O)Nc1ccc(Sc2nc(NCCN3CCCCC3)cc(Nc3cc(C)n[nH]3)n2)cc1] | — | 1.09 (3H, t), 1.35-1.37 (2H, m), 1.44-1.46 (4H, m), 2.03 (3H, s), 2.26 (6H, m), 2.33 (2H, q), 3.13 (2H, m), 5.45 (1H, s), 5.84 (1H, br s), 6.75 (1H, br s), 7.46 (2H, d), 7.68 (2H, d), 9.05 (1H, s), 10.05 (1H, s), 11.65 (1H, br s) | ES+ 481.3 ES− 479.4 |
| I-4 | 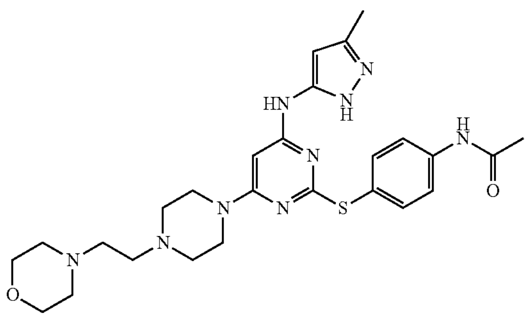 [SMILES: CC(=O)Nc1ccc(Sc2nc(Nc3cc(C)n[nH]3)cc(N3CCN(CCN4CCOCC4)CC3)n2)cc1] | — | 2.01 (3H, s), 2.07 (3H, s), 2.34-2.44 (12H, m), 3.3 (masked signal), 3.55 (4H, m), 5.43 (1H, s), 6.02 (1H, br s), 7.47 (2H, d), 7.67 (2H, d), 9.22 (1H, s), 10.14 (1H, s), 11.70 (1H, s) | ES+ 538.3 ES− 536.4 |
| I-5 | 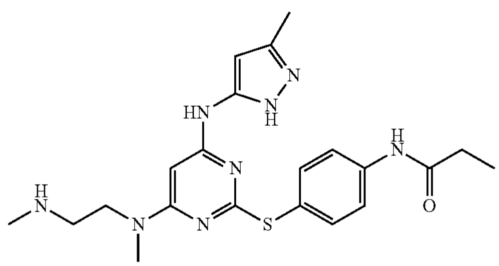 [SMILES: CCC(=O)Nc1ccc(Sc2nc(Nc3cc(C)n[nH]3)cc(N(C)CCNC)n2)cc1] | — | 1.06 (3H, t), 1.98 (3H, s), 2.20 (3H, s), 2.31 (2H, q), 2.50 (masked signal), 2.84 (3H, s), 3.38 (2H, m), 5.42 (1H, s), 5.77 (1H, s), 7.45 (2H, d), 7.65 (2H, d), 9.00 (1H, s), 10.18 (1H, s), 11.68 (1H, br s) | ES+ 441.3 ES− 439.4 |
| I-6 | 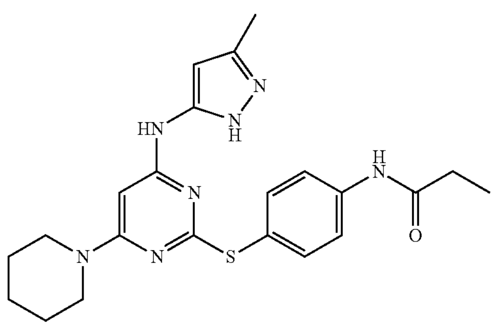 [SMILES: CCC(=O)Nc1ccc(Sc2nc(Nc3cc(C)n[nH]3)cc(N3CCCCC3)n2)cc1] | — | 1.10 (3H, t), 1.45 (4H, s), 1.60 (2H, s), 2.00 (3H, s), 2.35 (2H, q), 3.35 (4H, s), 5.40 (1H, s), 6.05 (1H, br s), 7.50 (2H, d), 7.70 (2H, d), 9.15 (1H, s), 10.05 (1H, s), 11.80 (1H, br s) | ES+ 438.3 |
| I-7 | 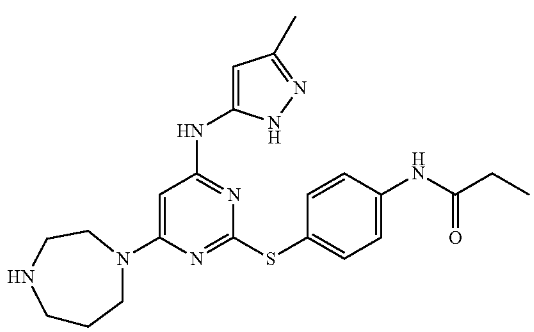 [SMILES: CCC(=O)Nc1ccc(Sc2nc(Nc3cc(C)n[nH]3)cc(N3CCCNCC3)n2)cc1] | — | 1.10 (3H, t), 1.70 (2H, s), 2.05 (3H, s), 2.35 (2H, q), 2.70 (2H, s), 2.75 (2H, s), 3.45 (2H, s), 5.50 (1H, s), 6.00 (1H, br s), 7.50 (2H, d), 7.70 (2H, d), 9.15 (1H, s), 10.10 (1H, s), 11.70 (1H, br s) | ES+ 453.3 |

TABLE 4-continued

Characterization Data for Representative Compounds

| No. | Structure | m.p. | ¹H-NMR | Mass Spec |
|---|---|---|---|---|
| I-8 | 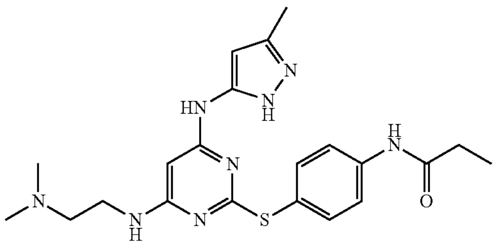 [SMILES: CCC(=O)Nc1ccc(Sc2nc(NCCN(C)C)cc(Nc3cc(C)n[nH]3)n2)cc1] | — | 1.10 (3H, t), 2.05 (3H, s), 2.15 (6H, s), 2.3-2.4 (4H, m), 3.15 (2H, s), 5.40 (1H, s), 5.85 (1H, br s), 6.75 (1H, br s), 7.45 (2H, d), 7.70 (2H, d), 9.05 (1H, br s), 10.10 (1H, s), 11.65 (1H, br s) | ES+ 441.3 |
| I-9 | 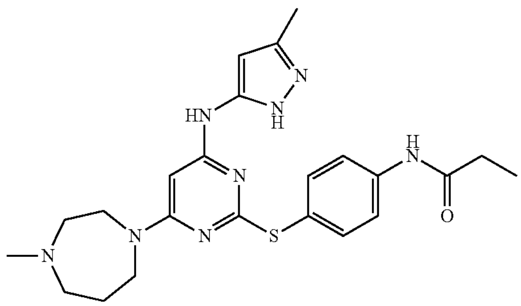 [SMILES: CCC(=O)Nc1ccc(Sc2nc(Nc3cc(C)n[nH]3)cc(N3CCCN(C)CC3)n2)cc1] | — | 1.09 (3H, t), 1.78 (2H, m), 2.03 (3H, s), 2.22 (3H, s), 2.33 (2H, q), 2.41 (4H, m), 3.3 (masked signal), 3.50 (2H, m), 5.48 (1H, s), 5.97 (1H, br s), 7.46 (2H, d), 7.68 (2H, d), 9.14 (1H, s), 10.06 (1H, s), 11.70 (1H, s) | ES+ 467.4 ES− 465.4 |
| I-10 | 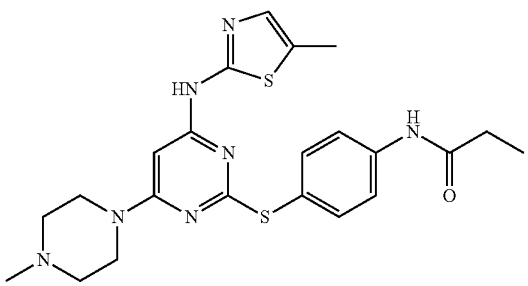 [SMILES: CCC(=O)Nc1ccc(Sc2nc(Nc3ncc(C)s3)cc(N3CCN(C)CC3)n2)cc1] | — | 1.09 (3H, t), 1.94 (3H, s), 2.20 (3H, s), 2.30-2.38 (6H, m), 3.42 (4H, m), 6.94 (1H, s), 7.49 (2H, d), 7.69 (2H, d), 7.95 (1H, s), 9.27 (1H, s), 10.07 (1H, s) | ES+ 470.2 ES− 468.3 |
| I-11 | 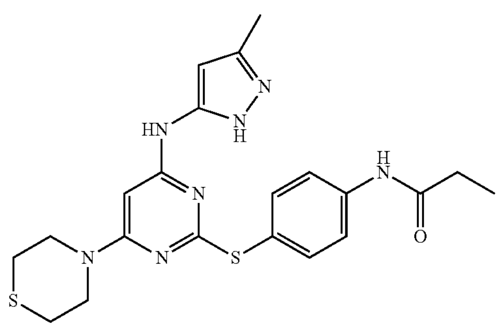 [SMILES: CCC(=O)Nc1ccc(Sc2nc(Nc3cc(C)n[nH]3)cc(N3CCSCC3)n2)cc1] | — | 1.10 (3H, t), 2.05 (3H, s), 2.35 (2H, d), 3.30 (4H, s), 3.70 (4H, s), 5.45 (1H, s), 6.05 (1H, br s), 7.45 (2H, d), 7.70 (2H, d), 9.20 (1H, s), 10.05 (1H, s), 11.70 (1H, br s) | ES+ 456.2 |
| I-12 | 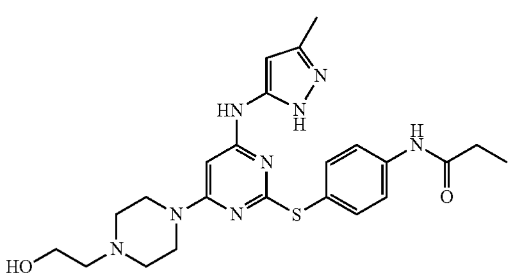 [SMILES: CCC(=O)Nc1ccc(Sc2nc(Nc3cc(C)n[nH]3)cc(N3CCN(CCO)CC3)n2)cc1] | — | 1.09 (3H, t), 2.00 (3H, s), 2.25-2.41 (8H, m), 3.35 (partially masked signal), 3.51 (2H, m), 4.45 (1H, m), 5.42 (1H, s), 6.00 (1H, br s), 7.47 (2H, d), 7.70 (2H, d), 9.22 (1H, s), 10.08 (1H, s), 11.70 (1H, s) | ES+ 483.4 ES− 481.4 |

TABLE 4-continued

Characterization Data for Representative Compounds

| No. | Structure | m.p. | ¹H-NMR | Mass Spec |
|---|---|---|---|---|
| I-13 | 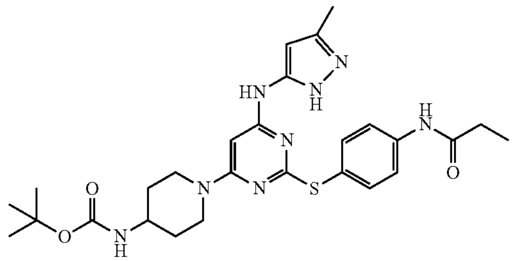 [SMILES: CCC(=O)Nc1ccc(Sc2nc(Nc3cc(C)n[nH]3)cc(N3CCC(NC(=O)OC(C)(C)C)CC3)n2)cc1] | — | 1.10 (3H, t), 1.23 (2H, q), 1.37 (9H, s), 1.70 (2H, d), 2.00 (3H, s), 2.35 (2H, q), 2.83 (2H, t), 3.47 (1H, m), 3.95 (2H, d), 5.45 (1H, s), 6.05 (1H, br s), 6.85 (1H, d), 7.50 (2H, d), 7.70 (2H, d), 9.20 (1H, s), 10.10 (1H, s), 11.70 (1H, br s) | ES+ 553.4 |
| I-14 | 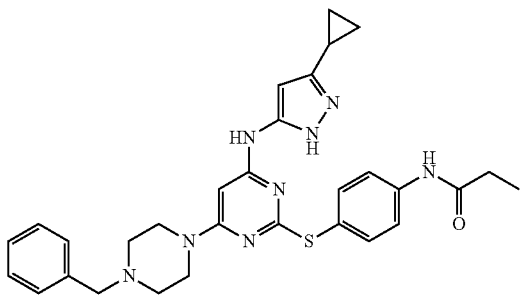 [SMILES: CCC(=O)Nc1ccc(Sc2nc(Nc3cc(C4CC4)n[nH]3)cc(N3CCN(Cc4ccccc4)CC3)n2)cc1] | — | 0.46-0.58 (2H, m), 0.78-0.89 (2H, m), 1.08 (3H, t, J = 7.5 Hz), 1.62-1.72 (1H, m), 2.21-2.43 (6H, m), 3.23-3.40 (4H, m), 3.50 (2H, s), 5.48 (1H, s), 6.10 (1H, brs), 7.19-7.36 (5H, m), 7.46 (2H, d, J = 8.5 Hz), 7.68 (2H, d, J = 8.5 Hz), 9.21 (1H, s), 10.03 (1H, s), 11.70 (1H, brs) | ES+ 555.34 ES− 553.40 |
| I-15 | 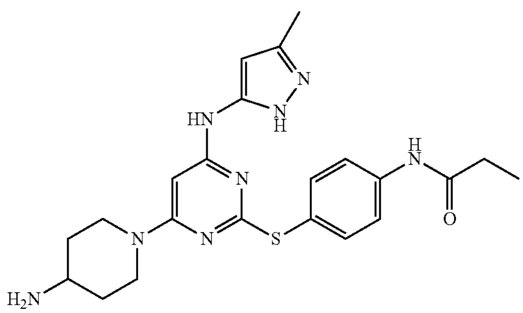 [SMILES: CCC(=O)Nc1ccc(Sc2nc(Nc3cc(C)n[nH]3)cc(N3CCC(N)CC3)n2)cc1] | — | 1.07 (3H, t), 1.12-1.22 (2H, m), 1.70 (2H, d), 2.02 (3H, s), 2.35 (2H, q), 2.80-2.90 (3H, m), 3.95 (2H, d), 5.45 (1H, s), 6.00 (1H, br s), 7.45 (2H, d), 7.70 (2H, d), 9.20 (1H, s), 10.15 (1H, s), 11.75 (1H, br s) | ES+ 453.3 |
| I-16 | 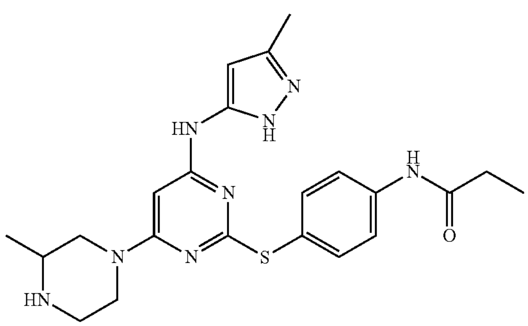 [SMILES: CCC(=O)Nc1ccc(Sc2nc(Nc3cc(C)n[nH]3)cc(N3CCNC(C)C3)n2)cc1] | — | 1.00 (3H, d), 1.08 (3H, t), 2.00 (3H, s), 2.35 (2H, q), 2.55-2.90 (3H, m), 3.65-4.25 (5H, m), 5.45 (1H, s), 6.00 (1H, br s), 7.45 (2H, d), 7.70 (2H, d), 9.25 (1H, br s), 10.20 (1H, s), 11.70 (1H, br s) | ES+ 453.3 |
| I-17 | 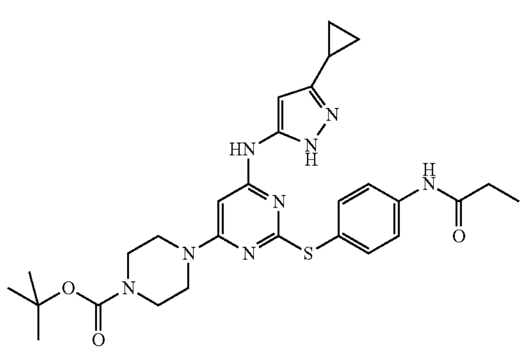 [SMILES: CCC(=O)Nc1ccc(Sc2nc(Nc3cc(C4CC4)n[nH]3)cc(N3CCN(C(=O)OC(C)(C)C)CC3)n2)cc1] | — | 0.47-0.55 (2H, m), 0.72-0.81 (2H, m), 1.08 (3H, t, J = 7.5 Hz), 1.41 (9H, s), 1.62-1.73 (1H, m), 2.32 (2H, q, J = 7.5 Hz), 3.30-3.41 (8H, m), 5.48 (1H, s), 6.10 (1H, brs), 7.47 (2H, d, J = 8.5 Hz), 7.70 (2H, d, J = 8.5 Hz), 9.29 (1H, brs), 10.05 (1H, s), 11.74 (1H, brs). | ES+ 565.33 ES− 563.36 |

TABLE 4-continued

Characterization Data for Representative Compounds

| No. | Structure | m.p. | ¹H-NMR | Mass Spec |
|---|---|---|---|---|
| I-18 | 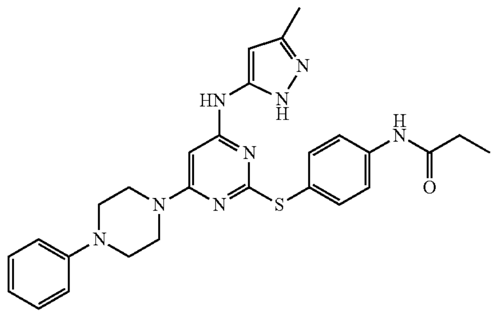 [SMILES: CCC(=O)Nc1ccc(Sc2nc(Nc3cc(C)n[nH]3)cc(N3CCN(c4ccccc4)CC3)n2)cc1] | — | 1.10 (3H, t), 2.01 (3H, s), 2.35 (2H, q), 3.16-3.18 (4H, m), 3.52-3.54 (4H, m), 5.43 (1H, s), 6.08 (1H, br s), 6.891 (1H, t), 6.97 (2H, d), 7.23 (2H, t), 7.49 (2H, d), 7.71 (2H, d), 9.28 (1H, s), 10.09 (1H, s), 11.72(1H, s) | ES+ 515.3 ES− 513.4 |
| I-19 | 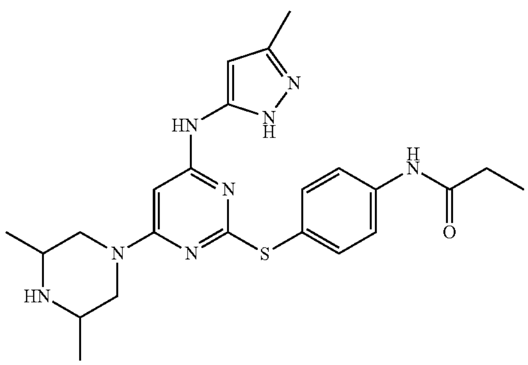 [SMILES: CCC(=O)Nc1ccc(Sc2nc(Nc3cc(C)n[nH]3)cc(N3CC(C)NC(C)C3)n2)cc1] | 151-152 | 0.95 (6H, s), 1.10 (3H, t), 2.05 (3H, s), 2.20 (2H, t), 2.35 (2H, q), 2.60 (2H, br s), 3.80 (2H, br s), 5.50 (1H, s), 6.05 (1H, br s), 7.50 (2H, d), 7.70 (2H, d), 9.15 (1H, s), 10.05 (1H, s), 11.70 (1H, br s) | ES+ 467.3 |
| I-20 | 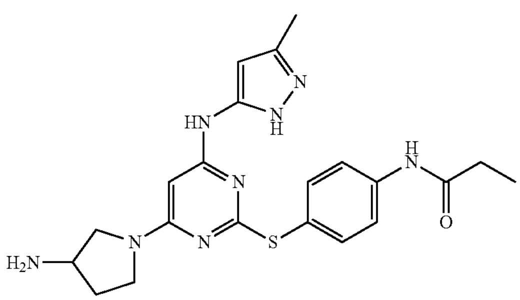 [SMILES: CCC(=O)Nc1ccc(Sc2nc(Nc3cc(C)n[nH]3)cc(N3CCC(N)C3)n2)cc1] | 159-160 | 1.10 (3H, t), 1.75 (1H, br s), 2.00 (3H, s), 2.30-2.40 (3H, m), 2.65 (1H, m), 3.25-3.45 (3H, m), 3.60 (1H, br s), 5.45 (1H, s), 5.80 (1H, br s), 7.50 (2H, d), 7.70 (2H, d), 9.15 (1H, br s), 10.05 (1H, s), 11.70 (1H, br s) | ES+ 439.3 |
| I-21 | 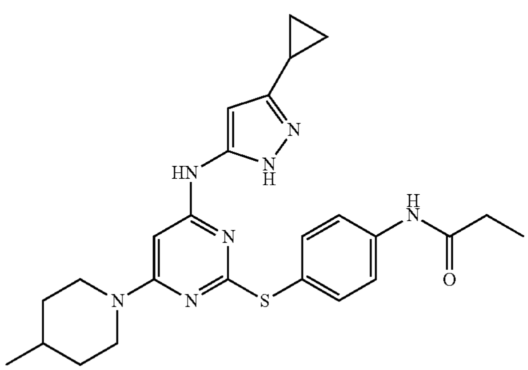 [SMILES: CCC(=O)Nc1ccc(Sc2nc(Nc3cc(C4CC4)n[nH]3)cc(N3CCC(C)CC3)n2)cc1] | — | 0.50-0.58 (2H, m), 0.78-0.85 (2H, m), 0.90 (3H, d, J = 6.1 Hz), 0.95-1.05 (2H, m), 1.09 (3H, t, J = 7.6 Hz), 1.51-1.64 (3H, m), 1.66-1.75 (1H, m), 2.32 (2H, q, J = 7.5 Hz), 2.66-2.78 (2H, m), 3.96-4.08 (2H, m), 5.48 (1H, s), 6.16 (1H, brs), 7.48 (2H, q, J = 8.6 Hz), 7.69 (2H, d, J = 8.6 Hz), 9.18 (1H, brs), 10.04 (1H, s), 11.74 (1H, brs) | ES+ 478.37 ES− 476.39 |

TABLE 4-continued

Characterization Data for Representative Compounds

| No. | Structure | m.p. | $^1$H-NMR | Mass Spec |
|---|---|---|---|---|
| I-22 | 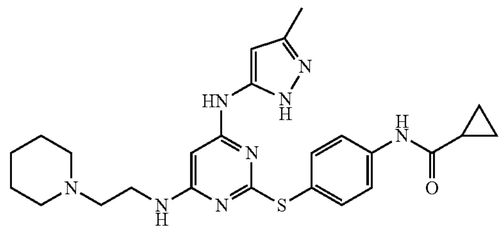 [SMILES: Cc1cc(Nc2cc(NCCN3CCCCC3)nc(Sc3ccc(NC(=O)C4CC4)cc3)n2)[nH]n1] | — | 0.80-0.81 (4H, m), 1.23-1.38 (6H, m), 1.82 (1H, m), 2.04 (3H, s), 2.34 (6H, m), 3.17 (2H, m), 5.47 (1H, s), 5.86 (1H, br s), 6.80 (1H, br s), 7.46 (2H, d), 7.69 (2H, d), 9.07 (1H, s), 10.41 (1H, s), 11.65 (1H, br s) | ES+ 493.4 ES− 491.4 |
| I-23 | 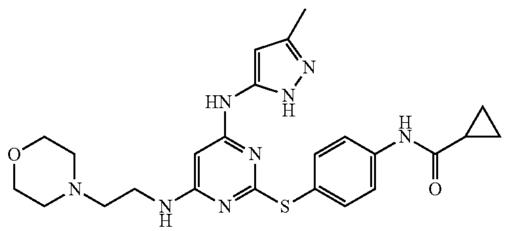 [SMILES: Cc1cc(Nc2cc(NCCN3CCOCC3)nc(Sc3ccc(NC(=O)C4CC4)cc3)n2)[nH]n1] | — | 0.80-0.82 (4H, m), 1.81 (1H, m), 2.04 (3H, s), 2.28 (6H, m), 3.15 (2H, m), 3.53 (4H, m), 5.48 (1H, s), 5.89 (1H, br s), 6.81 (1H, br s), 7.46 (2H, d), 7.68 (2H, d), 9.06 (1H, s), 10.38 (1H, s), 11.66(1H, br s) | ES+ 495.4 ES− 493.4 |
| I-24 | 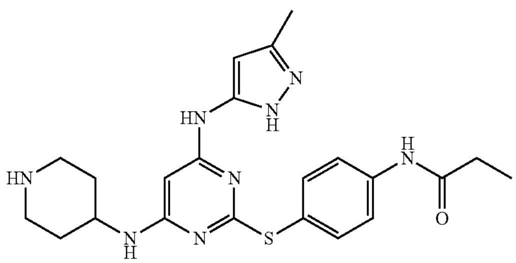 [SMILES: CCC(=O)Nc1ccc(Sc2nc(Nc3cc(C)n[nH]3)cc(NC3CCNCC3)n2)cc1] | — | 1.10 (3H, t), 1.47 (2H, q), 1.90 (2H, d), 2.03 (3H, s), 2.35 (2H, q), 2.85 (2H, br s), 3.23 (2H, d), 5.45 (1H, s), 5.90 (1H, br s), 7.05 (1H, d), 7.50 (2H, d), 7.70 (2H, d), 8.30 (1H, br s), 8.55 (1H, br s), 9.10 (1H, s), 10.10 (1H, s), 11.70 (1H, br s) | ES+ 453.3 |
| I-25 | 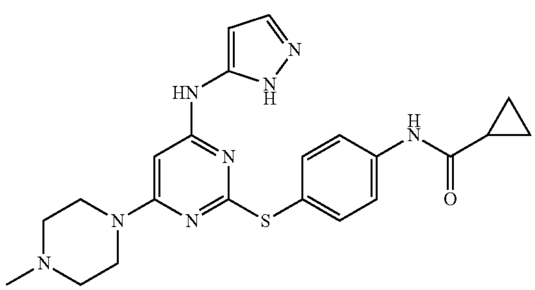 [SMILES: CN1CCN(c2cc(Nc3ccn[nH]3)nc(Sc3ccc(NC(=O)C4CC4)cc3)n2)CC1] | — | 0.83 (4H, m), 1.82 (1H, m), 2.22 (3H, s), 2.89 (4H, m), 3.33 (4H, m) (masked), 5.81 (1H, s), 6.24 (1H, br s), 7.36 (1H, s), 7.48 (2H, d), 7.65 (2H, d), 9.32 (1H, br s), 10.35 (1H, s), 12.10 (1H, br s) | ES+ 449.4 ES− 451.3 |
| I-26 | 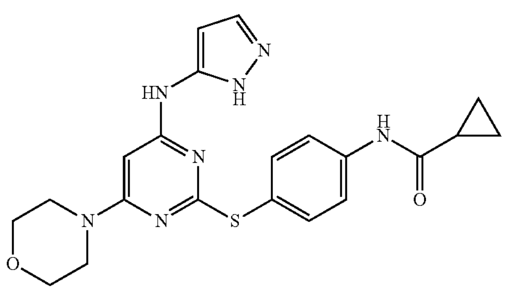 [SMILES: O=C(Nc1ccc(Sc2nc(Nc3ccn[nH]3)cc(N3CCOCC3)n2)cc1)C1CC1] | — | 0.81-0.83 (4H, m), 1.81 (1H, m), 3.29-3.31 (4H, m), 3.59-3.61 (4H, m), 5.82 (1H, s), 6.22 (1H, br s), 7.36 (1H, s), 7.48 (2H, d), 7.64 (2H, d), 9.38 (1H, s), 10.37 (1H, s), 12.10 (1H, s) | ES+ 438.3 ES− 436.4 |
| I-27 | 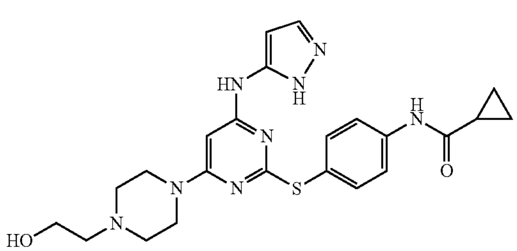 [SMILES: O=C(Nc1ccc(Sc2nc(Nc3ccn[nH]3)cc(N3CCN(CCO)CC3)n2)cc1)C1CC1] | — | 0.81-0.83 (4H, m), 1.81 (1H, m), 2.37-2.41 (6H, m), 3.3 (masked signal), 3.50 (2H, m), 4.44 (1H, s), 5.81 (1H, s), 6.23 (1H, br s), 7.36 (1H, s), 7.47 (2H, d), 7.65 (2H, d), 9.32 (1H, s), 10.38 (1H, s), 12.10 (1H, s) | ES+ 481.3 ES− 479.4 |

TABLE 4-continued

Characterization Data for Representative Compounds

| No. | Structure | m.p. | ¹H-NMR | Mass Spec |
|---|---|---|---|---|
| I-28 | 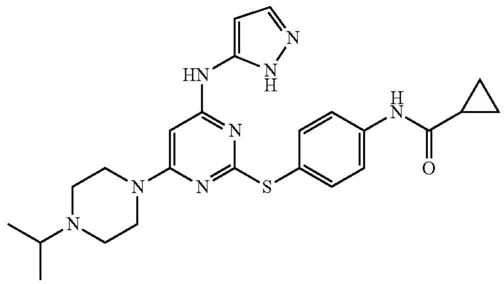 [SMILES: CC(C)N1CCN(c2cc(Nc3ccn[nH]3)nc(Sc3ccc(NC(=O)C4CC4)cc3)n2)CC1] | — | 0.81-0.83 (4H, m), 0.96 (6H, d), 1.81 (1H, m), 2.41-2.43 (4H, m), 2.65 (1H, m), 3.3 (masked signal), 5.82 (1H, s), 6.24 (1H, br s), 7.36 (1H, s), 7.47 (2H, d), 7.65 (2H, d), 9.31 (1H, s), 10.37 (1H, s), 12.10 (1H, s) | ES+ 479.3 ES− 477.4 |
| I-29 | 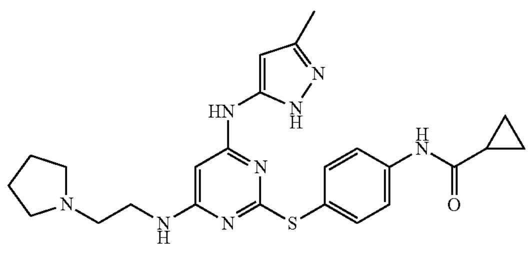 [SMILES: Cc1cc(Nc2cc(NCCN3CCCC3)nc(Sc3ccc(NC(=O)C4CC4)cc3)n2)[nH]n1] | 220-222 | — | M + H 479 |
| I-30 | 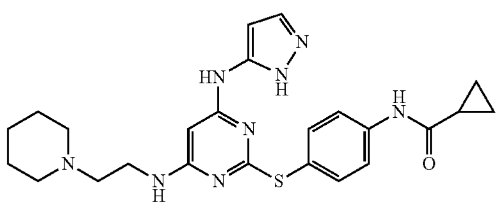 [SMILES: O=C(Nc1ccc(Sc2nc(NCCN3CCCCC3)cc(Nc3ccn[nH]3)n2)cc1)C1CC1] | — | 0.77-0.88 (4H, m), 1.28-1.55 (6H, m), 1.76-1.88 (1H, m), 2.12-2.43 (6H, m), 3.05-3.17 (2H, m), 5.81 (1H, brs), 6.04 (1H, brs), 6.84 (1H, brs), 7.39 (1H, brs), 7.47 (2H, d, J = 8.6 Hz), 7.65 (2H, d, J = 8.6 Hz), 9.12 (1H, brs), 10.33 (1H, s), 12.06 (1H, brs) | ES+ 479.35 ES− 477.41 |
| I-31 | 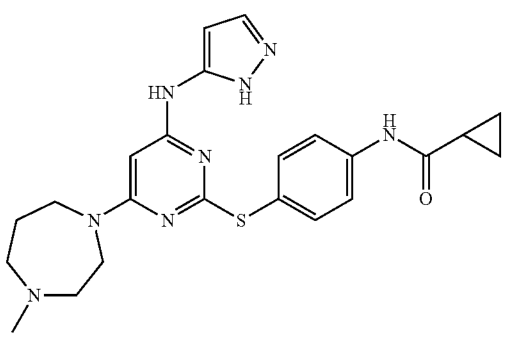 [SMILES: CN1CCCN(c2cc(Nc3ccn[nH]3)nc(Sc3ccc(NC(=O)C4CC4)cc3)n2)CC1] | — | 0.78-0.89 (4H, m), 1.59-1.86 (3H, m), 2.18-2.26 (3H, m), 2.38-2.52 (2H, m), 2.70-2.83 (2H, m), 3.28-3.55 (4H, m), 5.88 (1H, s), 6.15 (1H, brs), 7.39 (1H, s), 7.47 (2H, d, J = 8.6 Hz), 7.63 (2H, d, J = 8.6 Hz), 9.25 (1H, brs), 10.35 (1H, s), 12.11 (1H, brs) | ES+ 465.34 ES− 463.41 |
| I-32 | 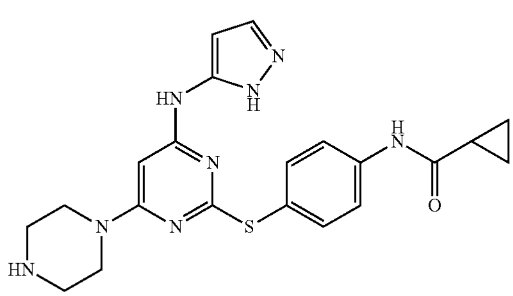 [SMILES: O=C(Nc1ccc(Sc2nc(Nc3ccn[nH]3)cc(N3CCNCC3)n2)cc1)C1CC1] | — | 0.72-0.90 (4H, m), 1.31-1.54 (3H, m), 2.20-2.35 (2H, m), 2.57-2.75 (3H, m), 3.12-3.50 (2H, m), 5.80 (1H, s), 6.22 (1H, brs), 7.38 (1H, brs), 7.47 (2H, d, J = 8.6 Hz), 7.64 (2H, d, J = 8.6 Hz), 9.29 (1H, s), 10.36 (1H, s), 12.08 (1H, brs) | ES+ 437.3 ES− 435.37 |

TABLE 4-continued

Characterization Data for Representative Compounds

| No. | Structure | m.p. | ¹H-NMR | Mass Spec |
|---|---|---|---|---|
| I-33 | 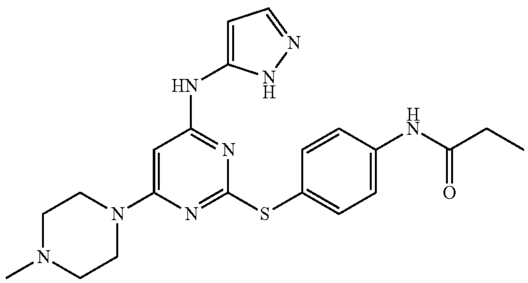 [SMILES: CCC(=O)Nc1ccc(Sc2nc(Nc3ccn[nH]3)cc(N3CCN(C)CC3)n2)cc1] | — | 1.15 (3H, t, J = 7.5 Hz), 2.19 (3H, s), 2.25-2.40 (6H, m), 3.30-3.40 (4H, m), 5.80 (1H, s), 6.25 (1H, brs), 7.38 (1H, s), 7.48 (2H, d, J = 8.6 Hz), 7.66 (2H, d, J = 8.6 Hz), 9.32 (1H, s), 10.06 (1H, s), 12.12 (1H, brs). | ES+ 439.34 ES− 437.39 |
| I-34 | 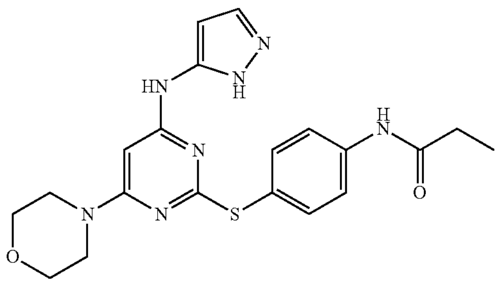 [SMILES: CCC(=O)Nc1ccc(Sc2nc(Nc3ccn[nH]3)cc(N3CCOCC3)n2)cc1] | — | 1.10 (3H, t, J = 7.5 Hz), 2.36 (2H, q, J = 7.5 Hz), 3.25-3.40 (4H, m), 3.55-3.69 (4H, m), 5.80 (1H, s), 6.21 (1H, brs), 7.32 (1H, brs), 7.47 (2H, d, J = 8.6 Hz), 7.65 (2H, d, J = 8.6 Hz), 9.38 (1H, s), 10.04 (1H, s), 12.10 (1H, brs). | ES+ 426.29 ES− 424.38 |
| I-35 | 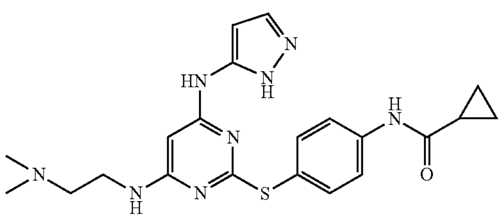 [SMILES: CN(C)CCNc1cc(Nc2ccn[nH]2)nc(Sc2ccc(NC(=O)C3CC3)cc2)n1] | Shrinks 140° C. Melts 280-282° C. | 0.81-0.82 (4H, m), 1.81 (1H, m), 2.08 (6H, s), 2.33 (2H, br s), 3.10-3.12 (2H, m), 5.81 (1H, s), 6.03 (1H, br s), 6.79 (1H, br s), 7.38 (1H, s), 7.47 (2H, d), 7.64 (2H, d), 9.12 (1H, brs), 10.34 (1H, s), 12.05 (1H, br s) | ES+ 439.40 ES− 437.24 |
| I-36 | 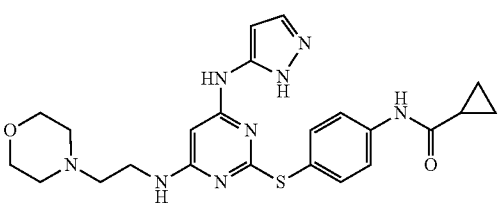 [SMILES: O=C(Nc1ccc(Sc2nc(NCCN3CCOCC3)cc(Nc3ccn[nH]3)n2)cc1)C1CC1] | mpt Shrinks 130° C. Melts 209-212° C. | 0.81-0.82 (4H, m), 1.80 (1H, m), 2.24 (6H, m), 3.10-3.15 (2H, m), 3.51-3.53 (4H, m), 5.84 (1H, br s), 6.05 (1H, br s), 6.87 (1H, br s), 7.41 (1H, s), 7.48 (2H, d), 7.66 (2H, d), 9.13 (1H, br s), 10.35 (1H, s), 12.07 (1H, br s) | ES+ 481.34 ES− 479.39 |
| I-37 | 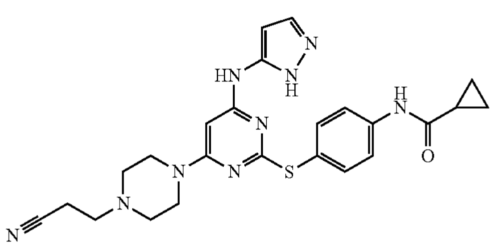 [SMILES: N#CCCN1CCN(c2cc(Nc3ccn[nH]3)nc(Sc3ccc(NC(=O)C4CC4)cc3)n2)CC1] | 131-132 | 0.80-0.85 (4H, m), 1.82 (1H, quin), 2.40-2.45 (4H, m), 2.58 (2H, t), 2.70 (2H, t), 3.33-3.38 (4H, m), 5.85 (1H, s), 6.30 (1H, br s), 7.40 (1H, s), 7.50 (2H, d), 7.70 (2H, d), 9.35 (1H, s), 10.40 (1H, s), 12.10 (1H, br s) | ES+ 490.3 |
| I-38 | 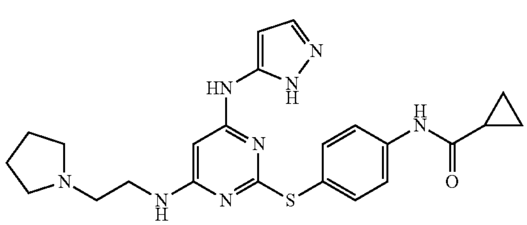 [SMILES: O=C(Nc1ccc(Sc2nc(NCCN3CCCC3)cc(Nc3ccn[nH]3)n2)cc1)C1CC1] | Shrinks 220° C. mpt greater than 340° C. | 0.80-0.82 (4H, m), 1.63 (4H, m), 1.63 (1H, m), 2.33 (6H, m), 3.10-3.13 (2H, m), 5.82 (1H, s), 5.99 (1H, br s), 6.87 (1H, br s), 7.38 (1H, s), 7.46 (2H, d), 7.65 (2H, d), 9.17 (1H, br s), 10.37 (1H, s), 12.07 (1H, br s) | ES+ 465.39 ES− 463.31 |

TABLE 4-continued

Characterization Data for Representative Compounds

| No. | Structure | m.p. | $^1$H-NMR | Mass Spec |
|---|---|---|---|---|
| I-39 | 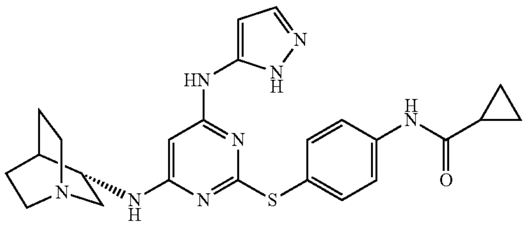 [SMILES: O=C(Nc1ccc(Sc2nc(Nc3ccn[nH]3)cc(N[C@@H]3CN4CCC3CC4)n2)cc1)C1CC1] | — | 0.80-0.83 (4H, m), 1.15-2.02 (5H, m), 2.22-2.47 (1H, 2m), 2.63-2.79 (1H, 2m), 2.91-3.62 (6H, m), 4.03-4.53 (1H, 2m), 5.80 (1H, s), 6.15 and 6.24 (1H, 2br s), 7.35 (1H, s), 7.46-4.49 (2H, d), 7.65-7.69 (2H, 2d), 9.32 and 9.37 (1H, 2s), 10.48 and 10.49 (1H, 2s), 12.09 (1H, br s) | ES+ 477.3 ES− 475.4 |
| I-40 | 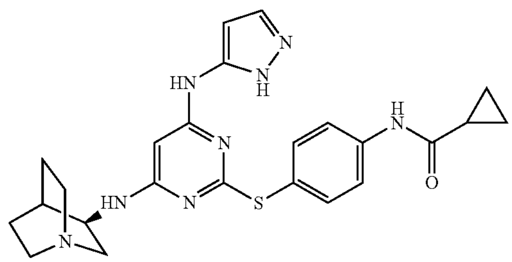 [SMILES: O=C(Nc1ccc(Sc2nc(Nc3ccn[nH]3)cc(N[C@H]3CN4CCC3CC4)n2)cc1)C1CC1] | — | 0.80-0.83 (4H, m), 1.15-2.02 (5H, m), 2.22-2.47 (1H, 2m), 2.63-2.79 (1H, 2m), 2.91-3.62 (6H, m), 4.03-4.53 (1H, 2m), 5.80 (1H, s), 6.15 and 6.24 (1H, 2br s), 7.35 (1H, s), 7.46-4.49 (2H, d), 7.65-7.69 (2H, 2d), 9.32 and 9.37 (1H, 2s), 10.48 and 10.49 (1H, 2s), 12.09 (1H, br s) | ES+ 477.3 ES− 475.4 |
| I-41 | 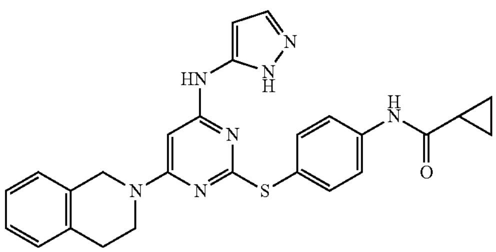 [SMILES: O=C(Nc1ccc(Sc2nc(Nc3ccn[nH]3)cc(N3CCc4ccccc4C3)n2)cc1)C1CC1] | — | 0.79-0.89 (4H, m), 1.80-1.89 (1H, m), 2.65-2.73 (1H, m), 2.90-2.99 (1H, m), 4.49 (2H, s), 5.86 (1H, brs), 6.30 (1H, brs), 6.95-7.20 (4H, m), 7.40 (1H, s), 7.50 (2H, d, J = 8.6 Hz), 7.69 (2H, d, J = 8.6 Hz), 9.36 (1H, s), 10.40 (1H, s), 12.15 (1H, brs) | ES+ 484.36 ES− 482.37 |
| I-42 | 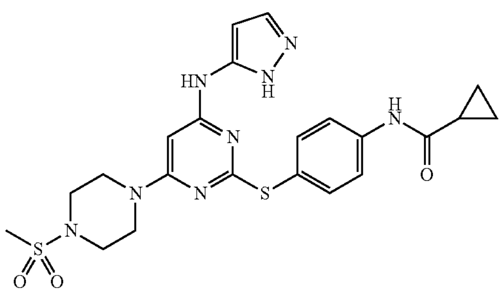 [SMILES: CS(=O)(=O)N1CCN(c2cc(Nc3ccn[nH]3)nc(Sc3ccc(NC(=O)C4CC4)cc3)n2)CC1] | 168-169 | 0.80-0.88 (4H, m), 1.82 (1H, m), 2.88 (3H, s), 3.13 (4H, br s), 3.48 (4H, br s), 5.82 (1H, s), 6.27 (1H, br s), 7.40 (1H, s), 7.50 (2H, d), 7.68 (2H, d), 9.41 (1H, s), 10.40 (1H, s), 12.15 (1H, br s) | ES+ 515.3 |
| I-43 | 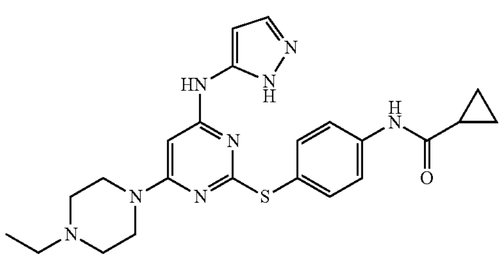 [SMILES: CCN1CCN(c2cc(Nc3ccn[nH]3)nc(Sc3ccc(NC(=O)C4CC4)cc3)n2)CC1] | — | 0.86 (7H, m), 1.43 (2H, m), 1.80 (1H, m), 2.23 (2H, t), 2.33 (4H, m), 3.31 (4H, m) (masked), 5.81 (1H, s), 6.23 (1H, br s), 7.36 (1H, s), 7.48 (2H, d), 7.65 (2H, d), 9.31 (1H, s), 10.35 (1H, s), 12.15 (1H, br s) | ES+ 463.4 ES− 465.3 |
| I-44 | 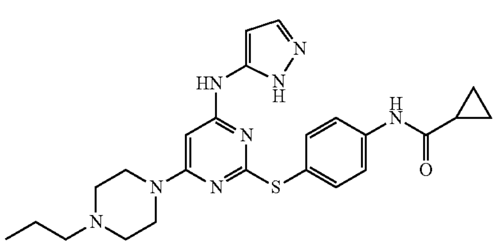 [SMILES: CCCN1CCN(c2cc(Nc3ccn[nH]3)nc(Sc3ccc(NC(=O)C4CC4)cc3)n2)CC1] | — | 0.83 (4H, m), 1.82 (1H, m), 2.22 (3H, s), 2.89 (4H, m), 3.33 (4H, m) (masked), 5.81 (1H, s), 6.24 (1H, br s), 7.36 (1H, s), 7.48 (2H, d), 7.65 (2H, d), 9.32 (1H, br s), 10.35 (1H, s), 12.10 (1H, br s) | ES+ 477.5 ES− 479.4 |

TABLE 4-continued

Characterization Data for Representative Compounds

| No. | Structure | m.p. | ¹H-NMR | Mass Spec |
|---|---|---|---|---|
| I-45 | 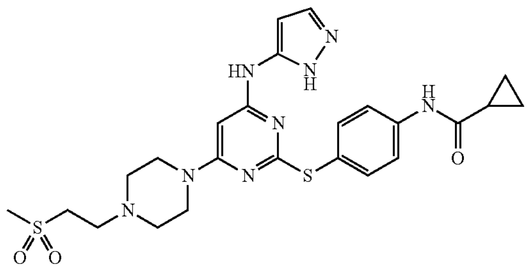 [SMILES: CS(=O)(=O)CCN1CCN(c2cc(Nc3ccn[nH]3)nc(Sc3ccc(NC(=O)C4CC4)cc3)n2)CC1] | 154-155 | 0.80-0.84 (4H, m), 1.80 (1H, quin), 2.40-2.43 (4H, m), 2.72 (2H, t), 3.03 (3H, s), 3.28-3.35 (6H, m), 5.80 (1H, s). 6.25 (1H, br s), 7.40 (1H, s), 7.50 (2H, d), 7.65 (2H, d), 9.35 (1H, s), 10.40 (1H, s), 12.10 (1H, br s) | ES+ 543.3 |
| I-46 | 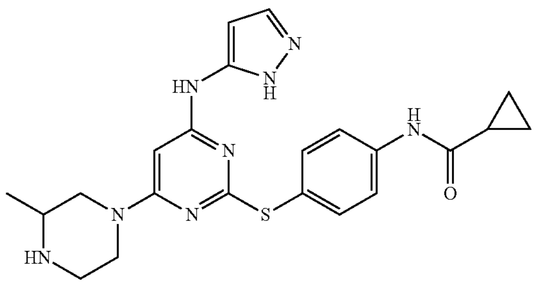 [SMILES: CC1CN(c2cc(Nc3ccn[nH]3)nc(Sc3ccc(NC(=O)C4CC4)cc3)n2)CCN1] | 160-161 | 0.80-0.85 (4H, m), 1.06 (3H, d), 1.80 (1H, quin), 2.67 (1H, br s), 3.65 (1H, m), 4.05 (1H, br s), 5.85 (1H, s), 6.25 (1H, br s), 7.40 (1H, s), 7.50 (2H, d), 7.65 (2H, d), 9.30 (1H, br s), 10.35 (1H, s), 12.10 (1H, br s) | ES+ 451.3 |
| I-47 | 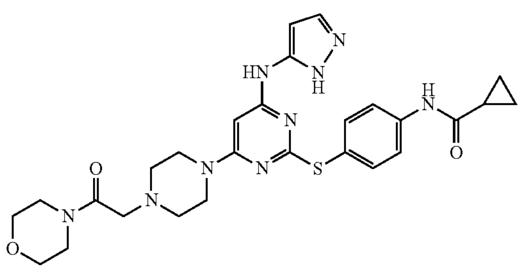 [SMILES: O=C(Nc1ccc(Sc2nc(Nc3ccn[nH]3)cc(N3CCN(CC(=O)N4CCOCC4)CC3)n2)cc1)C1CC1] | 158-159 | 0.80-0.85 (4H, m), 1.82 (1H, quin), 2.35-2.45 (4H, m), 3.17 (2H, br s), 3.22-3.26 (2H, m), 3.42-3.45 (2H, m), 3.50-3.58 (6H, m), 5.85 (1H, s), 6.25 (1H, br s), 7.40 (1H, s), 7.50 (2H, d), 7.70 (2H, d), 9.35 (1H, br s), 10.40 (1H, s), 12.10 (1H, br s) | ES+ 564.3 |
| I-48 | 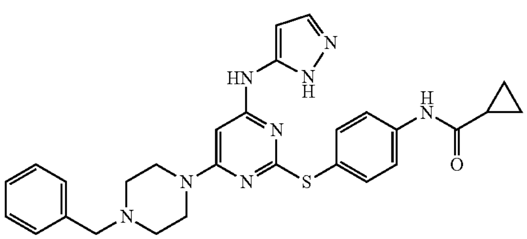 [SMILES: O=C(Nc1ccc(Sc2nc(Nc3ccn[nH]3)cc(N3CCN(Cc4ccccc4)CC3)n2)cc1)C1CC1] | — | 0.78-0.82 (4H, m), 1.79 (1H, m), 2.36 (4H, m), 3.3 (masked signal), 3.48 (2H, s), 5.81 (1H, s), 6.19 (1H, br s), 7.24-7.35 (6H, m), 7.47 (2H, d), 7.63 (2H, d), 9.33 (1H, s), 10.34 (1H, s), 12.09 (1H, s) | ES+ 527.4 ES− 525.4 |
| I-49 | 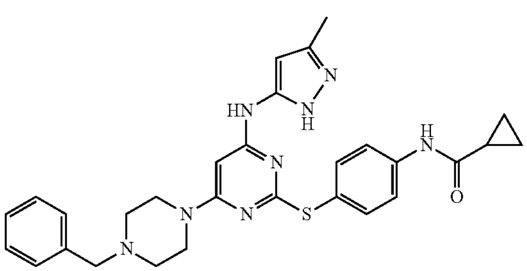 [SMILES: Cc1cc(Nc2cc(N3CCN(Cc4ccccc4)CC3)nc(Sc3ccc(NC(=O)C4CC4)cc3)n2)[nH]n1] | — | 0.80-0.81 (4H, m), 1.80 (1H, m), 2.00 (3H, s), 2.36-2.38 (4H, m), 3.3 (masked signal), 3.49 (2H, s), 5.42 (1H, s), 5.99 (1H, br s), 7.25-7.35 (5H, m), 7.47 (2H, d), 7.69 (2H, d), 9.23 (1H, s), 10.39 (1H, s), 11.69 (1H, s) | ES+ 541.4 ES− 539.4 |

TABLE 4-continued

Characterization Data for Representative Compounds

| No. | Structure | m.p. | ¹H-NMR | Mass Spec |
|---|---|---|---|---|
| I-50 | 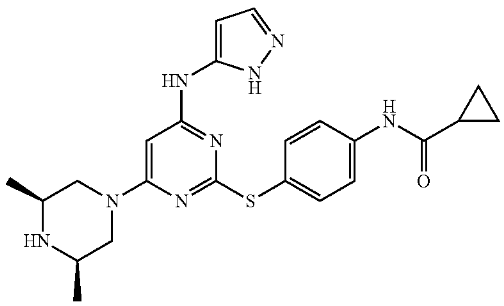 [SMILES: C[C@@H]1CN(c2cc(Nc3ccn[nH]3)nc(Sc3ccc(NC(=O)C4CC4)cc3)n2)C[C@H](C)N1] | — | 0.80 (4H, m), 0.93 (6H, d), 1.82 (1H, m), 2.20 (2H, t), 2.58 (2H, m), 3.79 (2H, m), 5.87 (1H, s), 6.23 (1H, br s), 7.40 (1H, s), 7.47 (2H, d), 7.74 (2H, d), 9.27 (1H, br s), 10.35 (1H, s), 12.11 (1H, br s) | ES+ 463.5 ES− 465.4 |
| I-51 | 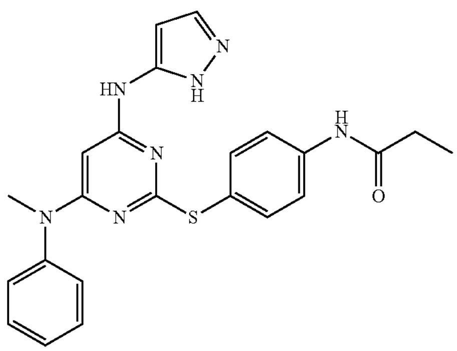 [SMILES: CCC(=O)Nc1ccc(Sc2nc(Nc3ccn[nH]3)cc(N(C)c3ccccc3)n2)cc1] | — | 1.10 (£h, t, J = 7.5 Hz), 2.36 (2H, q, J = 7.5 Hz), 3.32 (3H, s), 5.80 (1H, brs), 6.05 (1H, brs), 7.12-7.45 (6H, m), 7.49 (2H, d, J = 8.6 Hz), 7.71 (2H, d, J = 8.6 Hz), 9.48 (1H, brs), 10.11 (1H, s), 12.05 (1H, brs). | ES+ 446.31 ES− 444.34 |
| I-52 | 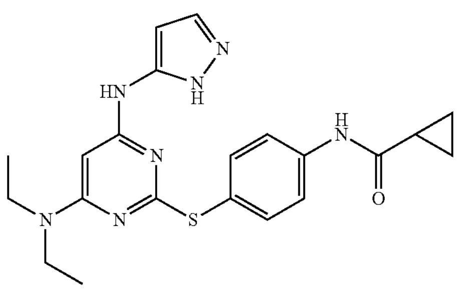 [SMILES: CCN(CC)c1cc(Nc2ccn[nH]2)nc(Sc2ccc(NC(=O)C3CC3)cc2)n1] | — | 0.75-0.89 (4H, m), 0.89-1.03 (6H, m), 1.74-1.88 (1H, m), 3.15.3.29 (4H, m), 5.89 (1H, brs), 6.18 (1H, brs), 7.42 (1H, brs), 7.47 (2H, d, J = 8.6 Hz), 7.63 (2H, d, J = 8.6 Hz), 9.19 (1H, brs), 10.34 (1H, s), 12.10 (1H, brs). | ES+ 424.34 ES− 422.35 |
| I-53 | 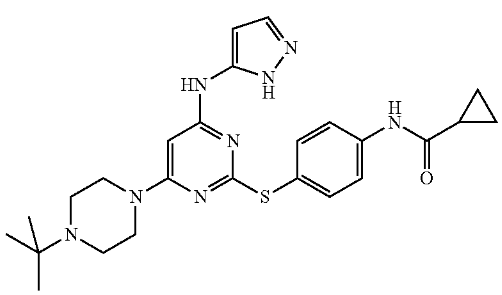 [SMILES: CC(C)(C)N1CCN(c2cc(Nc3ccn[nH]3)nc(Sc3ccc(NC(=O)C4CC4)cc3)n2)CC1] | 167-169 | 0.81-0.83 (4H, m), 1.00 (9H, s), 1.81 (1H, m), 2.47 (4H, m), 3.14 (4H, m), 5.82 (1H, s), 6.20 (1H, br s), 7.36 (1H, s), 7.47 (2H, d), 7.65 (2H, d), 9.32 (1H, s), 10.37 (1H, s), 12.09 (1H, s) | ES+ 493.4 ES− 491.4 |
| I-54 | 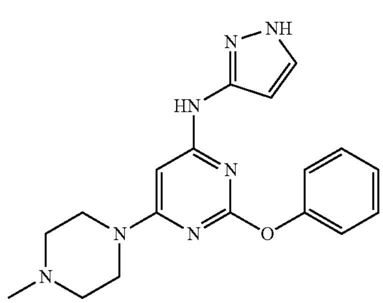 [SMILES: CN1CCN(c2cc(Nc3cc[nH]n3)nc(Oc3ccccc3)n2)CC1] | — | 2.21 (3H, s), 2.27-2.40 (4H, m), 3.31-3.50 (4H, m), 5.90 (1H, s), 6.31 (1H, brs), 7.10-7.25 (3H, m), 7.35-7.50 (3H, m), 9.38 (1H, s), 12.14 (1H, brs). | ES+ 352.28 ES− 350.32 |

TABLE 4-continued

Characterization Data for Representative Compounds

| No. | Structure | m.p. | ¹H-NMR | Mass Spec |
|---|---|---|---|---|
| I-55 | 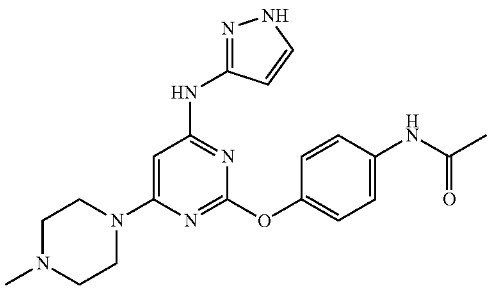 [SMILES: CC(=O)Nc1ccc(Oc2nc(Nc3cc[nH]n3)cc(N3CCN(C)CC3)n2)cc1] | — | 2.05 (3H, s), 2.19 (3H, s), 2.26-2.39 (4H, m), 3.36-3.46 (4H, m), 5.95 (1H, brs), 6.37 (1H, brs), 7.06 (2H, d, J = 8.9 Hz), 7.45 (1H, brs), 7.56 (2H, d, J = 8.9 Hz), 9.30 (1H, brs), 9.95 (1H, s), 12.12 (1H, s). | ES+ 409.31 ES− 407.37 |
| I-56 | 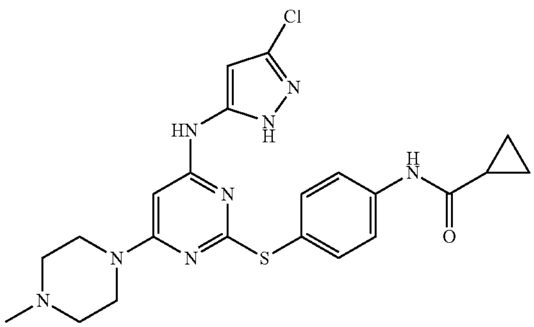 [SMILES: CN1CCN(c2cc(Nc3cc(Cl)n[nH]3)nc(Sc3ccc(NC(=O)C4CC4)cc3)n2)CC1] | drkns 250 277-9 | | ES+ 485.3 |
| I-57 | 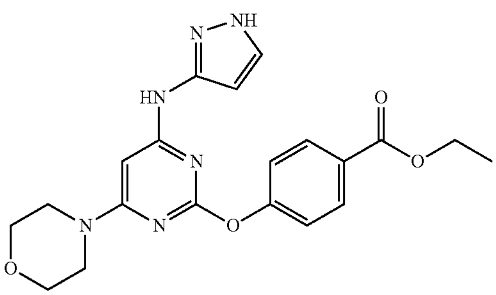 [SMILES: CCOC(=O)c1ccc(Oc2nc(Nc3cc[nH]n3)cc(N3CCOCC3)n2)cc1] | — | 1.34 (3H, t, J = 7.1 Hz), 3.33-3.42 (4H, m), 3.59-3.68 (4H, m), 4.32 (2H, q, J = 7.1 Hz), 5.94 (1H, s), 6.40 (1H, brs), 7.29 (2H, d, J = 8.7 Hz), 7.49 (1H, brs), 7.99 (2H, d, J = 8.7 Hz), 9.50 (1H, s), 12.20 (1H, brs). | ES+ 411.30 ES− 409.37 |
| I-58 | 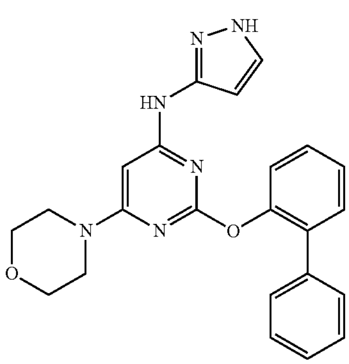 [SMILES: c1ccc(-c2ccccc2Oc2nc(Nc3cc[nH]n3)cc(N3CCOCC3)n2)cc1] | — | 3.30-3.39 (4H, m), 3.60-3.65 (4H, m), 5.89 (1H, s), 6.25 (1H, brs), 7.15-7.50 (9H, m), 9.40 9!H, brs), 12.12 (1H, s). | ES+ 415.32 ES− 413.37 |

| No. | Structure | m.p. | ¹H-NMR | Mass Spec |
|---|---|---|---|---|
| I-59 | 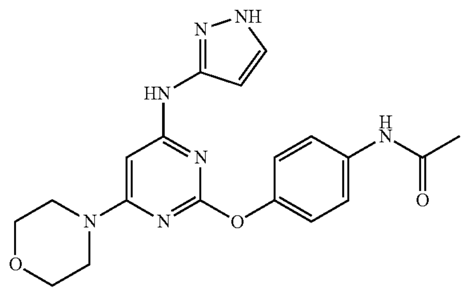 [SMILES: CC(=O)Nc1ccc(Oc2nc(Nc3cc[nH]n3)cc(N3CCOCC3)n2)cc1] | — | 2.05 (3H, s), 3.25-3.45 (4H, m), 3.59-3.70 (4H, m), 5.94 (1H, s), 6.35 (1H, brs), 7.07 (2H, d, J = 8.9 Hz), 7.46 (1H, brs), 7.58 (2H, d, J = 8.9 Hz), 9.40 (1H, s), 9.98 (1H, s), 12.13 (1H, brs). | ES+ 396.32 ES− 394.38 |
| I-60 | 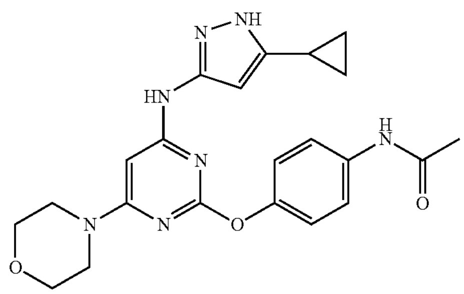 [SMILES: CC(=O)Nc1ccc(Oc2nc(Nc3cc(C4CC4)[nH]n3)cc(N3CCOCC3)n2)cc1] | — | 0.38-0.48 (2H, m), 0.79-0.89 (2H, m), 1.64-1.73 (1H, m), 2.04 (3H, s), 3.34-3.40 (4H, m), 3.61-3.69 (4H, m), 5.46 (1H, s), 6.10 (1H, brs), 7.05 (2H, d, J = 8.9 Hz), 7.61 (2H, d, J = 8.9 Hz), 9.34 (1H, s), 9.99 (1H, s), 11.85 (1H, brs). | ES+ 436.36 ES− 434.41 |
| I-61 | 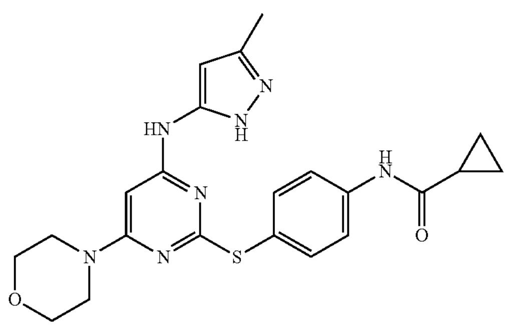 [SMILES: Cc1cc(Nc2cc(N3CCOCC3)nc(Sc3ccc(NC(=O)C4CC4)cc3)n2)[nH]n1] | 238-239 | 0.85 (4H, s), 1.80 (1H, m), 2.00 (3H, s), 3.35 (4H, s), 3.60 (4H, s), 5.43 (1H, s), 6.00 (1H, br s), 7.50 (2H, d), 7.70 (2H, d), 9.30 (1H, s), 10.40 (1H, s), 11.70 (1H, br s) | ES+ 452.2 |
| V-1i | 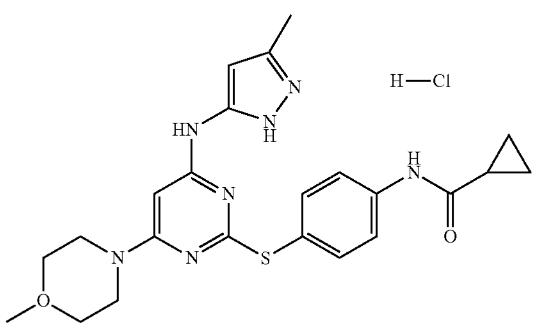 | — | 0.81 (4H, d), 1.83 (1H, m), 2.02 (3H, s), 2.77 (3H, s), 2.90-3.17 (4H, m), 4.09-4.33 (4H, m), 5.46 (1H, s), 6.06 (1H, s), 7.47 (2H, d), 7.72 (2H, d), 9.35 (1H, s), 1.45 (1H, s), 10.62 (1H, s), 11.72 (1H, s) | — |
| V-1iii | 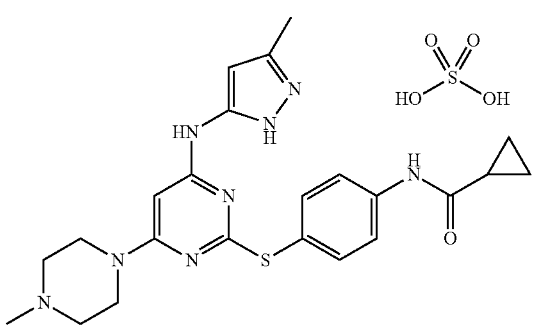 | — | 0.81-0.83 (4H, d), 1.81 (1H, m), 2.04 (3H, s), 2.82-2.83 (3H, m), 3.08-3.11 (4H, m), 3.42-3.47 (4H, m), 4.14-4.17 (br m, OH), 5.49 (1H, s), 6.04 (1H, s), 7.48 (2H, d), 7.71 (2H, d), 9.53 (1H, s), 9.64 (1H, s), 10.39 (1H, s) | — |

TABLE 4-continued

Characterization Data for Representative Compounds

| No. | Structure | m.p. | ¹H-NMR | Mass Spec |
|---|---|---|---|---|
| V-1iv | 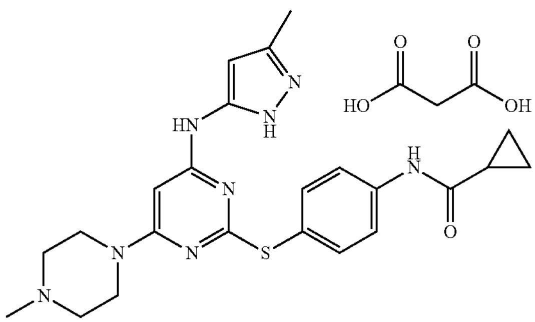 | — | 0.82 (4H, d), 1.80 (1H, m), 2.02 (3H, s), 2.45 (3H, s), 2.69 (brs. OH), 3.01 (2H, s), 3.38-3.47 (8H, m), 5.45 (1H, s), 6.05 (1H. s), 7.47 (2H, d), 7.70 (2H, d), 9.25 (1H, s), 10.36 (1H, s) | — |
| V-1v | 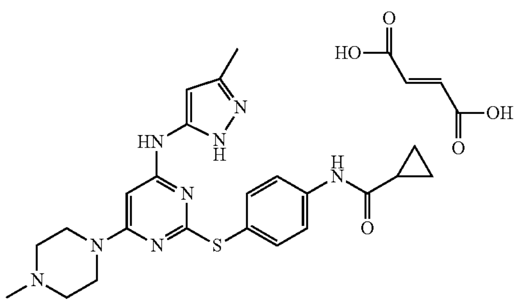 | — | 0.80-0.82 (4H, m), 1.81 (1H, m), 2.02 (3H, s), 2.21 (3H, s), 2.34-2.36 (4H, m), 3.36-3.38 (masked signal for 4H + OH), 5.45 (1H, s), 6.04 (1H, s), 6.61 (1H, s), 7.47 (2H, d), 7.69 (2H, d), 9.18 (1H, s), 10.36 (1H, s) | — |
| V-1vi | 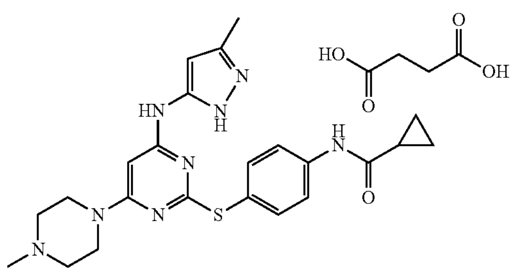 | — | 0.80-0.82 (4H, d), 1.81 (1H, m), 2.02 (3H, s), 2.21 (3H, s), 2.33-2.36 (4H, m), 2.41 (4H, s), 3.30-3.45 (masked signal, 4H, m), 4.19 (1H, br s), 5.45 (1H, s), 6.03 (1H, br s), 7.47 (2H, d), 7.69 (2H, d), 9.18 (1H, s), 10.35 (1H, s), 11.70 (1H br s) | — |
| V-1vii | 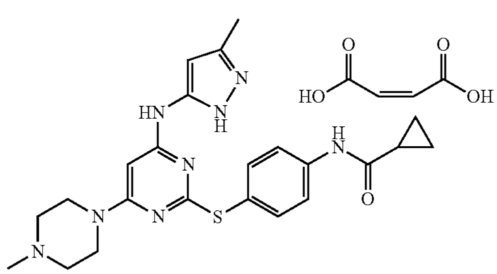 | — | 0.81-0.83 (4H, d), 1.81 (1H, m), 2.02 (3H, s), 2.80 (3H, s), 3.11-3.45 (masked signal, 8H, m), 5.45 (1H, s), 6.07 (3H, s), 7.48 (2H, d), 7.71 (2H, d), 9.36 (1H, s), 10.38 (1H, s), 11.75 (1H, br s) | — |
| V-1viii | 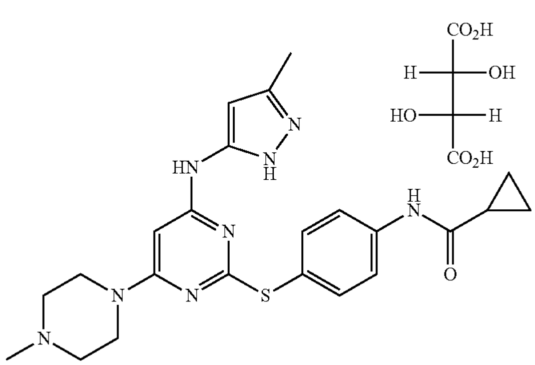 | — | 0.81-0.82 (4H, d), 1.81 (1H, m), 2.02 (3H, s), 2.27 (3H, s), 2.43 (4H, m), 3.38-3.47 (masked signal, 4H, m), 4.20 (2H, s), 5.45 (1H, s), 6.04 (1H, br s), 7.47 (2H, d), 7.69 (2H, d), 9.20 (1H, s), 10.36 (1H, s) | — |

TABLE 4-continued
Characterization Data for Representative Compounds
| No. | Structure | m.p. | ¹H-NMR | Mass Spec |
|---|---|---|---|---|
| V-1ix | 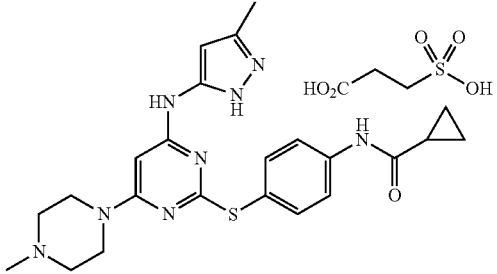 | — | 0.81-0.83 (4H, d), 1.81 (1H, m), 2.02 (3H, s), 2.82 (3H, s), 3.03-3.13 (4H, m), 3.36-3.75 (masked signal, 6H, m), 4.12-4.15 (2H, m), 5.45 (1H, s), 6.05 (1H, s), 7.48 (2H, d), 7.71 (2H, d), 9.37 (1H, s), 9.61 (1H, br s), 10.38 (1H, s) | — |
| V-1x | 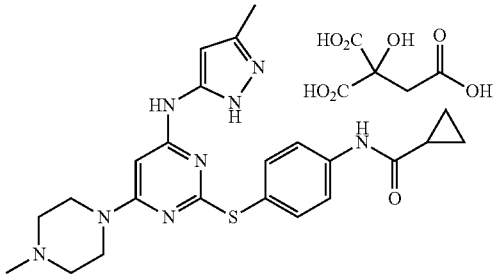 | — | 0.81-0.82 (4H, d), 1.81 (1H, m), 2.02 (3H, s), 2.40 (3H, s), 2.54-2.68 (8H, m), 3.40-3.45 (masked signal, 4H, m), 4.32 (1H, br s), 5.45 (1H, s), 6.05 (1H, br s), 7.47 (2H, d), 7.69 (2H, d), 9.24 (1H, s), 10.36 (1H, s) | — |
| V-1xi | 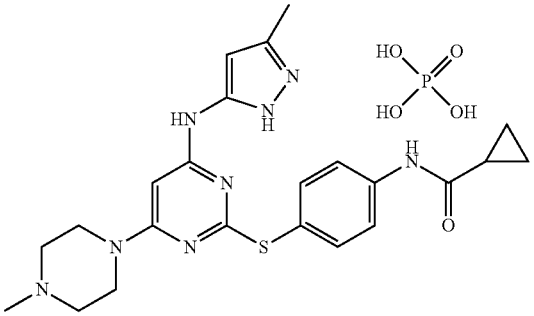 | — | 0.80-0.82 (4H, d), 1.80 (1H, m), 2.02 (3H, s), 2.31 (3H, s), 2.50 (masked signal, 4H), 3.36-3.47 (4H, m), 4.88 (br m, OH), 5.45 (1H. s), 6.04 (1H, s), 7.47 (2H, d), 7.69 (2H, d), 9.22 (1H, s), 10.36 (1H, s) | — |
| V-20i | 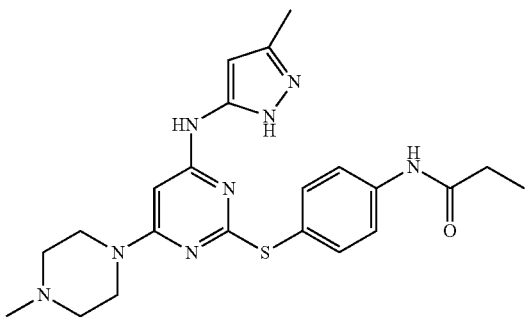\nHCl salt | — | 1.09 (3H, t), 2.00 (3H, s), 2.38 (2H, q), 2.77 (3H, s), 3.00 (2H, m), 3.18 (2H, m), 3.40 (2H, d), 4.10 (2H, d), 5.41 (1H, s), 6.06 (1H, br s), 7.48 (2H, d), 7.73 (2H, d), 9.42 (1H, s), 10.15 (1H, s), 10.64 (1H, br s), 11.77 (1H, br s) | ES- 451.4 ES+ 453.4 (M + H)+ |

TABLE 4-continued

Characterization Data for Representative Compounds

| No. | Structure | m.p. | $^1$H-NMR | Mass Spec |
|---|---|---|---|---|
| V-20ii | [chemical structure: 4-(4-methylpiperazin-1-yl)-6-((5-methyl-1H-pyrazol-3-yl)amino)-2-((4-propionamidophenyl)thio)pyrimidine, methanesulfonic acid salt] | | 1.09 (3H, t), 2.0 (3H, s), 2.35 (5H, m), 2.81 (3H, s), 3.09 (4H, m), 3.44 (2H, d), 4.12 (2H, d), 5.41 (1H, s), 6.02 (1H, br s), 7.48 (2H, d), 7.73 (2H, d), 9.44 (1H, s), 9.70 (1H, br s), 10.10 (1H, s), 11.80 (1H, br s) | ES− 451.4 ES+ 453.4 (M + H)+ |

Biological Assays

The activity of the compounds of this invention as kinase inhibitors may be assayed in vitro, in vivo or in a cell line. In vitro assays include assays that determine inhibition of either the kinase activity or ATPase activity of activated Aurora and/or FLT-3 enzyme. Alternate in vitro assays quantitate the ability of the inhibitor to bind to Aurora and/or FLT-3 and may be measured either by radiolabelling the inhibitor prior to binding, isolating the inhibitor/Aurora and/or inhibitor/FLT-3 complex and determining the amount of radiolabel bound, or by running a competition experiment where new compounds are incubated with Aurora and/or FLT-3 bound to known radioligands. One may use any type or isoform of Aurora, depending upon which Aurora type or isoform is to be inhibited. The details of the conditions used for the enzymatic assays are set forth in the Examples hereinbelow.

Example 10

$K_i$ Determination for the Inhibition of Aurora

Compounds were screened in the following manner for their ability to inhibit Aurora using a standard coupled enzyme assay (Fox et al (1998) *Protein Sci* 7, 2249). To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (LRRASLG, American Peptide, Sunnyvale, Calif.) was added a DMSO solution of a compound of the present invention to a final concentration of 30 μM. The resulting mixture was incubated at 30° C. for 10 minutes. The reaction was initiated by the addition of 10 μL of Aurora stock solution to give a final concentration of 70 nM in the assay. The rates of reaction were obtained by monitoring absorbance at 340 nm over a 5 minute read time at 30° C. using a BioRad Ultramark plate reader (Hercules, Calif.). The $K_i$ values were determined from the rate data as a function of inhibitor concentration.

Compounds of formula V of the present invention were found to be inhibitors of Aurora-1, Aurora-2, and Aurora-3.

Example 11

$K_i$ Determination for the Inhibition of FLT-3

Compounds were screened for their ability to inhibit FLT-3 activity using a radiometric filter-binding assay. This assay monitors the $^{33}$P incorporation into a substrate poly(Glu, Tyr) 4:1 (pE4Y). Reactions were carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 90 μM ATP and 0.5 mg/ml pE4Y (both from Sigma Chemicals, St Louis, Mo.). The final concentration of a compound of the present invention is generally between 0.01 and 5 μM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM MgCl$_2$, 25 mM NaCl, 1 mg/ml pE4Y and 180 μM ATP (containing 0.3 μCi of [γ-$^{33}$P] ATP for each reaction). Solution 2 contains 100 mM HEPES (pH 7.5), 10 mM MgCl$_2$, 25 mM NaCl, 2 mM DTT, 0.02% BSA and 3 nM FLT-3. The assay was run on a 96 well plate by mixing 50 μl each of Solution 1 and 2.5 ml of the compounds of the present invention. The reaction was initiated with Solution 2. After incubation for 20 minutes at room temperature, the reaction was stopped with 50 μl of 20% TCA containing 0.4 mM of ATP. All of the reaction volume was then transferred to a filter plate and washed with 5% TCA by a Harvester 9600 from TOMTEC (Hamden, Conn.). The amount of $^{33}$P incorporation into pE4y was analyzed by a Packard Top Count Microplate Scintillation Counter (Meriden, Conn.). The data was fitted using Prism software to get an IC$_{50}$ or $K_i$.

Compounds of formula V of the present invention were found to be inhibitors of FLT-3.

Example 12

IC$_{50}$ Determination for the Inhibition of Aurora in a Colo205 Cellular Assay Compounds were also assayed for the inhibition of cell proliferation. In this assay, a complete media was prepared by adding 10% fetal bovine serum, L-glutamine and penicillin/streptomycin solution to RPMI 1640 medium (Sigma). Colon cancer cells (COLO-205 cell line) were added to a 96 well plate at a seeding density of 1.25×104 cells/well/150 μL. A solution of test compound was prepared in complete media by serial dilution, the test compound solution (50 μL) was added to each per well.

Each plate contained a series of wells in which only complete media (200 μL) was added to form a control group in order to measure maximal proliferation. A vehicle control group was also added to each plate. The plates were incubated at 37° C. for 2 days. A stock solution of $^3$H-thymidine (1 mCi/mL, Amersham Phamacia UK) was diluted to 20 μCi/mL in RPMI medium then 25 μL of this solution was added to each well. The plates were further incubated at 37° C. for 3 hours then harvested and analyzed for $^3$H-thymidine uptake using a liquid scintillation counter.

Compounds of formula V of the present invention were found to be inhibitors of proliferation of Colo205 cancer cells.

Example 13

Measurement of Cell Proliferation in a Panel of Tumour and Normal Cell Types: $^3$H thymidine Incorporation Assay The $^3$H thymidine incorporation assay was chosen as a well characterized method of determining cell proliferation. Cells from normal tissues and a wide variety of different tumour types were chosen for analysis. Many of the tumour cells were selected because they express high levels of Aurora proteins (e.g. MCF-7, PC3, A375, A549) (See section 5.3.5 and Bischoff et al EMBO J. 1998 17, 3052-3065) and/or are able to form tumours in nude mice or rats (e.g. HCT116, MCF-7 and MDA-MB-231).

Logarithmically growing cells were incubated with compound for 96 hours. To measure cell proliferation, 3 hours prior to the end of the experiment 0.5 μCi of $^3$H thymidine was added to each well. Cells were then harvested, washed and the incorporated radioactivity counted on a Wallac microplate beta-counter. To determine the inhibition of proliferation, cpm were plotted versus compound concentration, and the $IC_{50}$ graphically determined.

Table 5 below sets forth the cell lines utilized in the above described cell proliferation assay. For each cell line, the inhibition of cell proliferation and $^3$H thymidine incorporation (96 hour time-point) was determined.

TABLE 5

| Origin | Cell line |
| --- | --- |
| Colorectal adenocarcinoma | HCT-116 |
| Colorectal adenocarcinoma | LS174T |
| Leukemia | HL60 |
| Mammary gland adenocarcinoma | MDA-MB-231 |
| Mammary gland adenocarcinoma | ZR-75-1 |
| Mammary gland adenocarcinoma | MCF-7 |
| Prostate adenocarcinoma | PC3 |
| Pancreatic | MIA-Pa-Ca-2 |
| Melanoma | A375 |
| Primary PHA-stimulated human lymphocytes | PHA blasts |

While a number of embodiments of this invention have been described, it is apparent that the basic examples may be altered to provide other embodiments which utilize the compounds and methods of this invention. Therefore, it will be appreciated that the scope of this invention is to be defined by the appended claims rather than by the specific embodiments which have been represented by way of example.

We claim:
1. A method for preparing a compound of formula I:

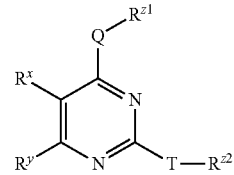

wherein:
Q is independently selected from oxygen, sulfur or N(R);
T is independently selected from oxygen or sulfur;
each R is independently selected from hydrogen or an optionally substituted $C_{1-6}$ aliphatic group;
$R^x$ is U—$R^5$;
$R^5$ is selected from halogen, $NO_2$, CN, R, or Ar;
each U is independently selected from a valence bond or a $C_{1-4}$ alkylidene chain, wherein:
  up to two methylene units of U are optionally and independently replaced by —O—, —S—, —SO—, —SO$_2$—, —N(R)SO$_2$—, —SO$_2$N(R)—, —N(R)—, —C(O)—, —CO$_2$—, —N(R)C(O)—, —N(R)C(O)O—, —N(R)CON(R)—, —N(R)SO$_2$N(R)—, —N(R)N(R)—, —C(O) N(R)—, —OC(O)N(R)—, —C(R)=NN(R)—, or —C(R)=N—O—;
each Ar is independently selected from an optionally substituted ring selected from a 3-7 membered monocyclic or an 8-10 membered bicyclic saturated, partially unsaturated, or fully unsaturated ring having 0-4 heteroatoms independently selected from nitrogen, oxygen, or sulfur;
$R^y$ is —N($R^1$)$_2$;
each $R^1$ is independently selected from R or a 3-8 membered monocyclic, an 8-10 membered bicyclic, or a 10-12 membered tricyclic saturated, partially unsaturated, or fully unsaturated ring having 0-4 heteroatoms independently selected from nitrogen, oxygen, or sulfur, and wherein:
  each $R^1$ is optionally and independently substituted by up to four substituents independently selected from $R^2$;
each $R^2$ is independently selected from —$R^3$, —$OR^3$, —$SR^3$, —CN, —$NO_2$, oxo, halogen, —N($R^3$)$_2$, —C(O)$R^3$, —OC(O)$R^3$, —CO$_2R^3$, —SO$_2R^3$, —SO$_2$N($R^3$)$_2$, —N($R^3$)SO$_2R^3$, —C(O)NR($R^3$), —C(O)N($R^3$)$_2$, —OC(O)NR($R^3$), —OC(O)N($R^3$)$_2$, —NR$^3$C(O)$R^3$, —NR$^3$C(O)N($R^3$)$_2$, or —NR$^3$CO$_2$($R^3$);
each $R^3$ is independently selected from R or Ar;
$R^{z1}$ is selected from a $C_{1-6}$ aliphatic group or a 3-8 membered monocyclic, an 8-10 membered bicyclic, or a 10-12 membered tricyclic saturated, partially unsaturated, or fully unsaturated ring having 0-4 heteroatoms independently selected from oxygen, nitrogen or sulfur, wherein:
  $R^{z1}$ is substituted with 0-4 independently selected $R^2$ groups;
$R^{z2}$ is $C_{1-6}$ aliphatic group or a 3-8 membered monocyclic or an 8-10 membered bicyclic saturated, partially unsaturated, or fully unsaturated ring having 0-4 heteroatoms independently selected from nitrogen, oxygen or sulfur, wherein:

$R^{z2}$ is substituted by 0-4 substituents independently selected from oxo or U—$R^5$;

said process comprising the step of combining a compound of formula II and a compound of formula $R^y$—H in a suitable medium:

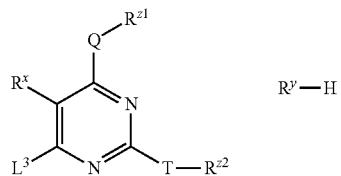

II wherein:
said suitable medium comprises:
  i) a suitable solvent independently selected from a protic solvent, a halogenated hydrocarbon, an ether, an aromatic hydrocarbon, a polar or non—polar aprotic solvent; and
  ii) optionally, a suitable base independently selected from organic amine, an alkaline earth metal carbonate, an alkaline earth metal hydride, or an alkaline earth metal hydroxide; and $L^3$ is a suitable leaving group independently selected from halogen, alkoxy, sulphonyloxy, optionally substituted alkylsulphonyl, optionally substituted alkenylsulfonyl, optionally substituted arylsulfonyl, and diazonium moieties.

2. The method according to claim 1, wherein said compound of formula II is prepared by combining a compound of formula III with a compound of formula $R^{z1}$—Q—H in a suitable medium:

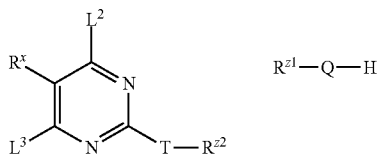

III wherein:
said suitable medium comprises:
  i) a suitable solvent independently selected from a protic solvent, a halogenated hydrocarbon, an ether, an aromatic hydrocarbon, a polar or non—polar aprotic solvent; and
  ii) optionally, a suitable base independently selected from organic amine, an alkaline earth metal carbonate, an alkaline earth metal hydride, or an alkaline earth metal hydroxide; and $L^2$ is a suitable leaving group independently selected from halogen, alkoxy, sulphonyloxy, optionally substituted alkylsulphonyl, optionally substituted alkenylsulfonyl, optionally substituted arylsulfonyl, and diazonium moieties.

3. The method according to claim 2, wherein said compound of formula III is prepared by combining a compound of formula IV with a compound of formula $R^{z2}$—T—H in a suitable medium:

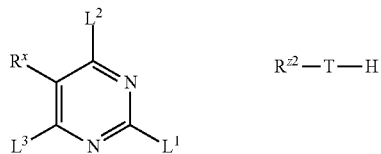

IV wherein:
said suitable medium comprises:
  i) a suitable solvent independently selected from a protic solvent, a halogenated hydrocarbon, an ether, an aromatic hydrocarbon, a polar or non—polar aprotic solvent; and
  ii) optionally, a suitable base independently selected from organic amine, an alkaline earth metal carbonate, an alkaline earth metal hydride, or an alkaline earth metal hydroxide; and $L^1$ is a suitable leaving group independently selected from halogen, alkoxy, sulphonyloxy, optionally substituted alkylsulphonyl, optionally substituted alkenylsulfonyl, optionally substituted arylsulfonyl, and diazonium moieties.

4. The method according to claim 1, wherein $L^3$ is selected from halogen, optionally substituted arylsulfonyl, or optionally substituted alkylsulphonyl.

5. The method according to claim 4, wherein $L^3$ is fluoro, chloro, bromo, iodo, paratoluenesulfonyl, methanesulfonyl, paranitrophenylsulfonyl, parabromophenylsulfonyl, or trifluoromethanesulfonate.

6. The method according to claim 5, wherein $L^3$ is chloro or iodo.

7. The method according to claim 2, wherein $L^2$ is halogen, optionally substituted arylsulfonyl, or optionally substituted alkylsulphonyl.

8. The method according to claim 7, wherein $L^2$ is fluoro, chloro, bromo, iodo, paratoluenesulfonate, methanesulfonate, paranitrophenylsulfonyl, parabromophenylsulfonyl, or trifluoromethanesulfonate.

9. The method according to claim 8, wherein $L^2$ is chloro or iodo.

10. The method according to claim 3, wherein $L^1$ is halogen, optionally substituted arylsulfonyl, or optionally substituted alkylsulphonyl.

11. The method according to claim 10, wherein $L^1$ is optionally substituted alkylsulfonyl.

12. The method according to claim 11, wherein $L^1$ is methanesulfonyl.

13. The method according to claim 1, wherein Q is N(R).

14. The method according to claim 1, wherein T is sulfur.

15. The method according to claim 1, wherein:
$R^1$ is selected from R or a 3-7 membered monocyclic or an 8-10 membered bicyclic saturated, partially unsaturated, or fully unsaturated ring having 0-4 heteroatoms independently selected from nitrogen, oxygen, or sulfur, or:
  each $R^1$ is R such that the two R on the same nitrogen atom are taken together to form an optionally substituted 4-7 membered saturated ring having up to two additional heteroatoms independently selected from nitrogen, oxygen, or sulfur, and wherein:
  each $R^1$ is optionally and independently substituted by up to four substituents selected from —$R^3$, —$OR^3$, —$SR^3$, —CN, —$NO_2$, oxo, halogen, —$N(R^3)_2$, —$C(O)R^3$, —$OC(O)R^3$, —$CO_2R^3$, —SO$_2$R$^3$, —SO$_2$N(R$^3$)$_2$, —N(R$^3$)SO$_2$R$^3$, —C(O)NR(R$^3$), —C(O)N(R$^3$)$_2$, —OC(O)NR(R$^3$), —OC(O)N(R$^3$)$_2$, —NR$^3$C(O)R$^3$, —NR$^3$C(O)N(R$^3$)$_2$, or —NR$^3$CO$_2$(R$^3$).

16. The method according to claim 15, wherein:
each R$^1$ is independently selected from R, wherein R is hydrogen or an optionally substituted C$_{1-4}$ aliphatic group.

17. The method according to claim 15, wherein:
each R$^1$ is R such that the two R groups are taken together to form an optionally substituted 4-7 membered saturated ring having up to two additional heteroatoms independently selected from nitrogen, oxygen, or sulfur.

18. The method according to claim 17, wherein R$^y$ is selected from pyrrolidin-1-yl, piperidin-1-yl, morpholin-4-yl, thiomorpholin-4-yl, piperazin-1-yl, diazepanyl, or tetrahydroisoquinolinyl, wherein each ring is optionally substituted with one or two groups independently selected from methyl, ethyl, methylsulfonyl, (CH$_2$)$_2$SO$_2$CH$_3$, cyclopropyl, CH$_2$cyclopropyl, (CH$_2$)$_2$OH, CO$_2$t-butyl, CH$_2$phenyl, phenyl, NH$_2$, NH(CH$_3$), N(CH$_3$)$_2$, (CH$_2$)$_2$NH$_2$, (CH$_2$)$_2$morpholin-4-yl, (CH$_2$)$_2$N(CH$_3$)$_2$, isopropyl, propyl, t-butyl, (CH2)2CN, or (CH$_2$)$_2$C(O)morpholin-4-yl.

19. The method according to claim 1, wherein R$^{z1}$ is a 3-7 membered monocyclic or an 8-10 membered bicyclic saturated, partially unsaturated, or fully unsaturated ring having 0-4 heteroatoms independently selected from oxygen, nitrogen or sulfur, wherein said ring is optionally and independently substituted by up to three substituents selected from —R$^3$, —OR$^3$, —SR$^3$, —CN, —NO$_2$, oxo, halogen, —N(R$^3$)$_2$, —C(O)R3, —OC(O)R$^3$, —CO$_2$R$^3$, —SO$_2$R$^3$, —SO$_2$N(R$^3$)$_2$, —N(R$^3$)SO$_2$R$^3$, —C(O)NR(R$^3$), —C(O)N(R$^3$)$_2$, —OC(O)NR(R$^3$), —OC(O)N(R$^3$)$_2$, —NR$^3$C(O)R$^3$, —NR$^3$C(O)N(R$^3$)$_2$, or —NR$^3$CO$_2$R$^3$.

20. The method according to claim 19, wherein R$^{z1}$ is a 5-6 membered fully unsaturated ring having 1—3 heteroatoms independently selected from nitrogen, oxygen, or sulfur, wherein said ring is optionally and independently substituted by up to three substituents selected from —R$^3$, —OR$^3$, —SR$^3$, —CN, —NO$_2$, oxo, halogen, —N(R$^3$)$_2$, —C(O)R$^3$, —OC(O)R$^3$, —CO$_2$R$^3$, —SO$_2$R$^3$, —SO$_2$N(R$^3$)$_2$, —N(R$^3$)SO$_2$R$^3$, —C(O)NR(R$^3$), —C(O)N(R$^3$)$_2$, —OC(O)NR(R$^3$), —OC(O)N(R$^3$)$_2$, —NR$^3$C(O)R$^3$, —NR$^3$C(O)N(R$^3$)$_2$, or —NR$^3$CO$_2$R$^3$.

21. The method according to claim 20, wherein R$^{z1}$ is an optionally substituted ring selected from pyrazole or any one of the following 5-6 membered rings:

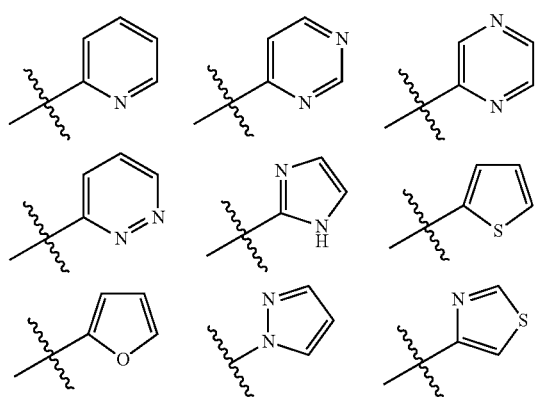

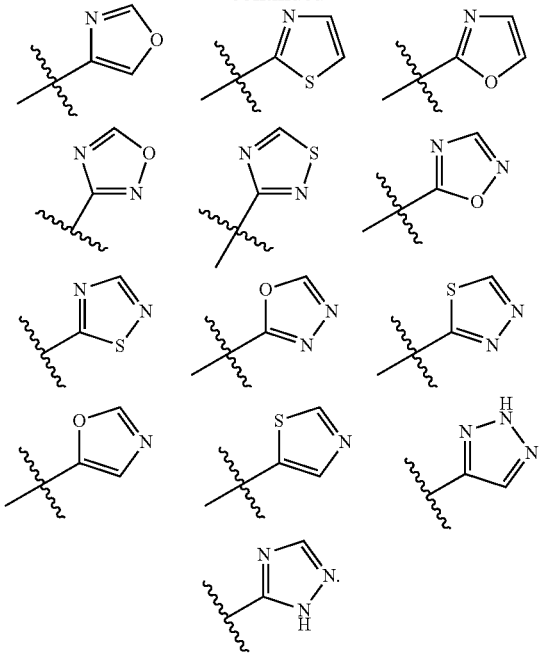

22. The method according to claim 21, wherein R$^{z1}$ is a pyrazole ring having up to two substituents independently selected from —N(R$^3$)$_2$, —OR$^3$, or a C$_1$—C$_4$ aliphatic group.

23. The method according to claim 22, wherein R$^{z1}$ is a pyrazole optionally substituted with one substituent selected from methyl, ethyl, propyl, isopropyl, t-butyl, cyclopropyl, or phenyl.

24. The method according to claim 1, wherein R$^{z2}$ is an optionally substituted ring selected from a 5-6 membered monocyclic or an 8-10 membered bicyclic saturated, partially unsaturated, or fully unsaturated ring having 0-4 heteroatoms independently selected from nitrogen, oxygen or sulfur, wherein said ring is optionally substituted by up to three substituents independently selected from halogen, —CN, —NO$_2$, —C(O)R$^3$, —CO$_2$R$^3$, —C(O)NR(R$^3$), —NR$^3$C(O)R$^3$, —N(R$^3$)$_2$, —N(R$^3$)SO$_2$R$^3$, —NR$^3$C(O)N(R$^3$)$_2$, or —NR$^3$CO$_2$R$^3$.

25. The method according to claim 24, wherein:
R$^{z2}$ is selected from phenyl, imidazolyl, pyrazolyl, pyridyl, pyridazinyl, pyrazinyl, naphthyl, tetrahydronaphthyl, benzimidazolyl, benzthiazolyl, quinolinyl, quinazolinyl, benzodioxinyl, isobenzofuran, indanyl, indolyl, indolinyl, indazolyl, or isoquinolinyl, wherein:
R$^{z2}$ is optionally substituted with up to three substituents independently selected from —Cl, —Br, —F, —CN, —CF$_3$, —COOH, —CONHMe, —CONHEt, —NH$_2$, —NHAc, —NHSO$_2$Me, —NHSO$_2$Et, —NHSO$_2$(n-propyl), —NHSO$_2$(isopropyl), —NHCOEt, —NHCOCH$_2$NHCH$_3$, —NHCOCH$_2$N(CO$_2$t-Bu)CH$_3$, —NHCOCH$_2$N(CH$_3$)$_2$, —NHCOCH$_2$CH$_2$N(CH$_3$)$_2$, —NHCOCH$_2$CH$_2$CH$_2$N(CH$_3$)$_2$, —NHCO(cyclopropyl), —NHCO(isopropyl), —NHCO(isobutyl), —NHCOCH$_2$(morpholin-4-yl), —NHCOCH$_2$CH$_2$(morpholin-4-yl), —NHCOCH$_2$CH$_2$CH$_2$(morpholin-4-yl), —NHCO$_2$(t-butyl), —NH(cyclohexyl), —NHMe, —NMe$_2$, —OH, —OMe, methyl, ethyl, cyclopropyl, isopropyl, or t-butyl.

26. The method according to claim 25, wherein $R^{z2}$ has one substituent selected from —$NR^3C(O)R^3$, wherein:

each $R^3$ is independently selected from R or Ar, and wherein:

R is hydrogen or an optionally substituted $C_{1-4}$ aliphatic group.

27. The method according to claim 1, wherein said solvent is a $C_{1-5}$ straight or branched alkyl alcohol, ether, or a polar or non-polar aprotic solvent.

28. The method according to claim 1, wherein said suitable base is selected from a trialkyl amine, sodium carbonate, potassium carbonate, sodium hydride, potassium hydride, sodium hydroxide, or potassium hydroxide.

* * * * *